US012329022B2

United States Patent
Kim et al.

(10) Patent No.: US 12,329,022 B2
(45) Date of Patent: Jun. 10, 2025

(54) SENSOR-EMBEDDED DISPLAY PANEL AND ELECTRONIC DEVICE

(71) Applicant: Samsung Electronics Co., Ltd., Suwon-si (KR)

(72) Inventors: Hyeongju Kim, Changwon-si (KR); Jisoo Shin, Suwon-si (KR); Sung Young Yun, Suwon-si (KR); Kyung Bae Park, Hwaseong-si (KR); Jeong Il Park, Seongnam-si (KR); Taejin Choi, Suwon-si (KR); Chul Joon Heo, Busan (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 482 days.

(21) Appl. No.: 17/726,027

(22) Filed: Apr. 21, 2022

(65) Prior Publication Data
US 2022/0367570 A1  Nov. 17, 2022

(30) Foreign Application Priority Data

Apr. 23, 2021 (KR) .................. 10-2021-0053299
Apr. 19, 2022 (KR) .................. 10-2022-0048097

(51) Int. Cl.
*H10K 65/00* (2023.01)
*C07D 421/04* (2006.01)
(Continued)

(52) U.S. Cl.
CPC ........... *H10K 65/00* (2023.02); *C07D 421/04* (2013.01); *C07D 421/14* (2013.01);
(Continued)

(58) Field of Classification Search
CPC ........... H10K 30/20–211; H10K 65/00; H10K 71/164–166
See application file for complete search history.

(56) References Cited

U.S. PATENT DOCUMENTS 8,525,577 B2   9/2013   Yofu et al.
9,379,343 B2   6/2016   Leem et al.
(Continued)

FOREIGN PATENT DOCUMENTS

CN    103682150 A    3/2014
EP      3637472 A1   4/2020
(Continued)

OTHER PUBLICATIONS

Partial European Search Report dated Dec. 2, 2022 for corresponding European Application No. 22168931.8.

*Primary Examiner* — Daniel P Shook
(74) *Attorney, Agent, or Firm* — Harness, Dickey & Pierce, P.L.C.

(57) ABSTRACT

A sensor-embedded display panel includes a substrate, a light emitting element on the substrate and including a light emitting layer, and a light absorption sensor on the substrate and including a light absorbing layer arranged in parallel with the light emitting layer along an in-plane direction of the substrate. The light absorbing layer is configured to absorb light of a red wavelength spectrum, a green wavelength spectrum, a blue wavelength spectrum, or any combination thereof. The light emitting layer includes a first organic material and the light absorbing layer includes a second organic material. A difference between respective sublimation temperatures of the first and second organic materials is less than or equal to about 150° C., wherein each sublimation temperature is a temperature at which a weight reduction of 10% relative to the initial weight occurs during thermogravimetric analysis under an ambient pressure of about 10 Pa or less.

29 Claims, 5 Drawing Sheets

(51) Int. Cl.
*C07D 421/14* (2006.01)
*C07D 471/04* (2006.01)
*C07D 471/06* (2006.01)
*C07D 471/14* (2006.01)
*C07D 487/04* (2006.01)
*C07D 493/06* (2006.01)
*C07D 517/04* (2006.01)
*C07D 517/22* (2006.01)
*C07F 5/02* (2006.01)
*C07F 7/08* (2006.01)
*C07F 7/30* (2006.01)
*H10K 30/30* (2023.01)
*H10K 30/81* (2023.01)
*H10K 59/35* (2023.01)

(52) U.S. Cl.
CPC ......... *C07D 471/04* (2013.01); *C07D 471/06* (2013.01); *C07D 471/14* (2013.01); *C07D 487/04* (2013.01); *C07D 493/06* (2013.01); *C07D 517/04* (2013.01); *C07D 517/22* (2013.01); *C07F 5/027* (2013.01); *C07F 7/0816* (2013.01); *C07F 7/30* (2013.01); *H10K 30/30* (2023.02); *H10K 30/81* (2023.02); *H10K 59/35* (2023.02)

(56) References Cited

U.S. PATENT DOCUMENTS

| | | | |
|---|---|---|---|
| 9,502,473 | B2 | 11/2016 | Lee et al. |
| 9,679,182 | B2 | 6/2017 | Bae et al. |
| 9,823,771 | B2 | 11/2017 | Bae et al. |
| 9,864,448 | B2 | 1/2018 | Bae et al. |
| 9,891,746 | B2 | 2/2018 | Bae et al. |
| 9,996,179 | B2 | 6/2018 | Bae et al. |
| 10,263,042 | B2 | 4/2019 | Sakurai et al. |
| 10,416,718 | B2 | 9/2019 | Cui |
| 10,464,935 | B2 | 11/2019 | Rosselli et al. |
| 10,790,454 | B2 | 9/2020 | Rosselli et al. |
| 2004/0116493 | A1 | 6/2004 | Sugimori et al. |
| 2017/0351364 | A1 | 12/2017 | Kim et al. |
| 2019/0123285 | A1 | 4/2019 | Shin et al. |
| 2020/0111851 | A1* | 4/2020 | Park ................... H10K 59/12 |
| 2020/0212138 | A1 | 7/2020 | Lee et al. |
| 2021/0005827 | A1 | 1/2021 | Rosselli et al. |
| 2021/0296409 | A1 | 9/2021 | Yamazaki et al. |

FOREIGN PATENT DOCUMENTS

| | | |
|---|---|---|
| JP | 2935998 B2 | 8/1999 |
| KR | 10-2011-0101435 A | 9/2011 |
| KR | 2016-0029697 A | 3/2016 |
| KR | 10-2017-0028787 | 3/2017 |
| KR | 10-2330698 B1 | 11/2021 |
| WO | WO-2002/040479 A1 | 5/2002 |
| WO | WO-02/065752 A1 | 8/2002 |
| WO | WO-2008/042859 A2 | 4/2008 |
| WO | WO-2008/042859 A3 | 8/2008 |
| WO | WO-2020/021399 A1 | 1/2020 |

* cited by examiner

SENSOR-EMBEDDED DISPLAY PANEL AND ELECTRONIC DEVICE

CROSS-REFERENCE TO RELATED APPLICATIONS

This application claims priority to and the benefit of, under 35 U.S.C. § 119, Korean Patent Applications Nos. 10-2021-0053299 and 10-2022-0048097 filed in the Korean Intellectual Property Office on Apr. 23, 2021 and Apr. 19, 2022, respectively, the entire contents of each of which are incorporated herein by reference.

BACKGROUND

1. Field

Sensor-embedded display panels and electronic devices are described.

2. Description of the Related Art

Recently, there is an increasing demand for a display device implementing biometric recognition technology that authenticates the person by extracting specific human biometric information or behavioral characteristic information with an automated device, centering on finance, health care, mobile devices, and the like.

SUMMARY

Some example embodiments provide a display device (e.g., a display panel) including a sensor capable of biometric recognition.

Such a sensor capable of biometric recognition may be disposed under the display panel or may be manufactured as a separate module and then mounted outside the display panel. However, when the sensor is disposed under the display panel, the object should be recognized through the display panel, various films and/or parts, etc., so performance may be degraded. When the sensor is separately manufactured and mounted as a separate module, there are limitations in terms of design and usability.

Some example embodiments provide a sensor-embedded display panel including a sensor that is integrated with the display panel to improve performance.

Some example embodiments provide an electronic device including the sensor-embedded display panel.

According to some example embodiments, a sensor-embedded display panel may include a substrate, a light emitting element on the substrate and including a light emitting layer, and a light absorption sensor on the substrate and including a light absorbing layer arranged in parallel with the light emitting layer along an in-plane direction of the substrate such that the light absorbing layer and the light emitting layer at least partially overlap in the in-plane direction. The light absorbing layer may be configured to absorb light of a red wavelength spectrum, a green wavelength spectrum, a blue wavelength spectrum, an infrared wavelength spectrum, or any combination thereof. The light emitting layer may include a first organic material and the light absorbing layer may include a second organic material, and a difference between the sublimation temperatures of the first organic material and the second organic material may be less than or equal to about 150° C., wherein each sublimation temperature is a temperature at which a weight reduction of 10% relative to an initial weight occurs during thermogravimetric analysis under an ambient pressure of about 10 Pa or less.

The light emitting element may include first, second, and third light emitting elements configured to emit light of different wavelength spectra, and the light absorption sensor may be configured to absorb light that is emitted from at least one of the first, second, or third light emitting elements and is reflected by the recognition target and to convert the reflected light into an electrical signal.

The sublimation temperature of the second organic material may be about 0° C. to about 390° C.

The sublimation temperature of the second organic material may be about 100° C. to about 390° C.

An energy bandgap of the second organic material may be greater than or equal to about 2.5 eV.

The second organic material may be a transparent n-type semiconductor.

The light emitting element and the light absorption sensor may each include a separate portion of a common electrode configured to apply a common voltage to both the light emitting element and the light absorption sensor, and the sensor-embedded display panel may further include a first common auxiliary layer continuously formed as a single piece of material that extends between the light emitting layer and the common electrode and between the light absorption layer and the common electrode.

A difference between a lowest unoccupied molecular orbital (LUMO) energy level of the first common auxiliary layer and a LUMO energy level of the second organic material may be about 0 eV to about 1.2 eV.

The sensor-embedded display panel may further include a second common auxiliary layer continuously formed as a single piece of material that extends between the light emitting layer and the substrate and between the light absorption layer and the substrate.

The second organic material may be represented by Chemical Formula 1.

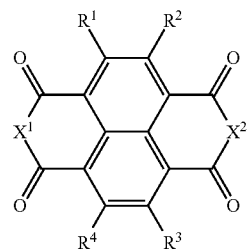

[Chemical Formula 1]

In Chemical Formula 1, $X^1$ and $X^2$ are each independently O or $NR^a$, and $R^1$ to $R^4$ and $R^a$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

The second organic material may be represented by Chemical Formula 1A or 1B.

[Chemical Formula 1A]

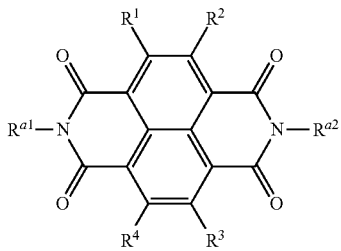

[Chemical Formula 1B]

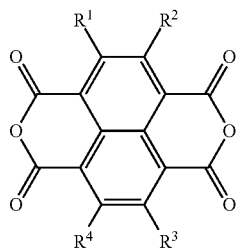

In Chemical Formulas 1A and 1B, $R^1$ to $R^4$, $R^{a1}$, and $R^{a2}$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

At least one of $R^{a1}$ or $R^{a2}$ may include an electron withdrawing group.

At least one of $R^{a1}$ or $R^{a2}$ may be a halogen; a cyano group; a halogen-substituted C1 to C30 alkyl group; a halogen-substituted C6 to C30 aryl group; a halogen-substituted C3 to C30 heterocyclic group; a cyano-substituted C1 to C30 alkyl group; a cyano-substituted C6 to C30 aryl group; a cyano-substituted C3 to C30 heterocyclic group; a substituted or unsubstituted pyridinyl group; a substituted or unsubstituted pyrimidinyl group; a substituted or unsubstituted triazinyl group; a substituted or unsubstituted pyrazinyl group; a substituted or unsubstituted quinolinyl group; a substituted or unsubstituted isoquinolinyl group; a substituted or unsubstituted quinazolinyl group; a C1 to C30 alkyl group substituted with a substituted or unsubstituted pyridinyl group; a C6 to C30 aryl group substituted with a substituted or unsubstituted pyridinyl group; a C1 to C30 alkyl group substituted with a substituted or unsubstituted pyrimidinyl group; a C6 to C30 aryl group substituted with a substituted or unsubstituted pyrimidinyl group; a C1 to C30 alkyl group substituted with a substituted or unsubstituted triazinyl group; a C6 to C30 aryl group substituted with a substituted or unsubstituted triazinyl group; a C1 to C30 alkyl group substituted with a substituted or unsubstituted pyrazinyl group; a C6 to C30 aryl group substituted with a substituted or unsubstituted pyrazinyl group; a C1 to C30 alkyl group substituted with a substituted or unsubstituted quinolinyl group; a C6 to C30 aryl group substituted with a substituted or unsubstituted quinolinyl group; a C1 to C30 alkyl group substituted with a substituted or unsubstituted isoquinolinyl group; a C6 to C30 aryl group substituted with a substituted or unsubstituted isoquinolinyl group; a C1 to C30 alkyl group substituted with a substituted or unsubstituted quinazolinyl group; a C6 to C30 aryl group substituted with a substituted or unsubstituted quinazolinyl group; or any combination thereof.

The light absorbing layer may further include a third organic material forming a pn junction with the second organic material, and a difference between respective sublimation temperatures of two materials selected from the first organic material, the second organic material, or the third organic material may be about 0° C. to about 150° C.

The third organic material may be a light absorbing material configured to selectively absorb light of any one of the red wavelength spectrum, the green wavelength spectrum, or the blue wavelength spectrum.

The third organic material may be represented by Chemical Formula 2.

[Chemical Formula 2]

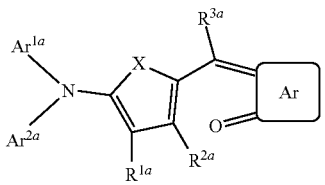

In Chemical Formula 2,

X is O, S, Se, Te, SO, $SO_2$, $CR^bR^c$, or $SiR^dR^e$,

Ar is a substituted or unsubstituted C6 to C30 arylene group, a substituted or unsubstituted C3 to C30 heterocyclic group, or a fused ring of two or more thereof, $Ar^{1a}$ and $Ar^{2a}$ are each independently a substituted or unsubstituted C6 to C30 aryl(ene) group or a substituted or unsubstituted C3 to C30 heteroaryl(ene) group, $R^{1a}$ to $R^{3a}$ and $R^b$ to $R^e$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, and $Ar^{1a}$, $Ar^{2a}$, $R^{1a}$, and $R^{2a}$ are each independently present, or two adjacent ones of $Ar^{1a}$, $Ar^{2a}$, $R^{1a}$ or $R^{2a}$ are bonded to each other to form a ring.

The third organic material may be represented by Chemical Formula 2A or 2B.

[Chemical Formula 2A]

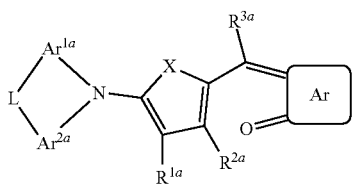

[Chemical Formula 2B]

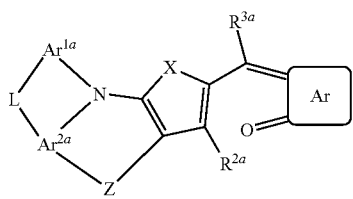

In Chemical Formulas 2A and 2B,

X is O, S, Se, Te, SO, $SO_2$, $CR^bR^c$, or $SiR^dR^e$,

Ar is a substituted or unsubstituted C6 to C30 arylene group, a substituted or unsubstituted C3 to C30 heterocyclic group, or a fused ring of two or more thereof, $Ar^{1a}$ and $Ar^{2a}$ are each independently a substituted or unsubstituted C6 to C30 arylene group or a substituted or unsubstituted C3 to C30 heteroarylene group, L and Z are each independently a single bond, O, S, Se, Te, SO, $SO_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and $R^{1a}$, $R^{2a}$, $R^{3a}$, and $R^b$ to $R^l$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof.

The light emitting element may include first, second, and third light emitting elements that are each configured to emit light of any one of the red wavelength spectrum, the green wavelength spectrum, or the blue wavelength spectrum, and the light absorbing layer may be configured to absorb light of a same wavelength spectrum as light emitted from at least one of the first, second, or third light emitting elements.

The sensor-embedded display panel may include a display area configured to display a color and a non-display area excluding the display area, and the light absorption sensor may be in the non-display area.

The light emitting element may include first, second, and third light emitting elements configured to emit light of different wavelength spectra from each other, and the display area may include a plurality of first subpixels configured to display red and including the first light emitting element, a plurality of second subpixels configured to display green and including the second light emitting element, and a plurality of third subpixels configured to display blue and including the third light emitting element, and the light absorption sensor may be between at least two of a first subpixel of the plurality of first subpixels, a second subpixel of the plurality of second subpixels, or a third subpixel of the plurality of third subpixels in the in-plane direction.

According to some example embodiments, a sensor-embedded display panel may include a display area configured to display a color and a non-display area excluding the display area and configured to not display any color, wherein the display area includes a first subpixel configured to display a first color and including a first light emitting element, a second subpixel configured to display a second color and including a second light emitting element, and a third subpixel configured to display a third color and including a third light emitting element. The non-display area may include a light absorption sensor that is between at least two of the first subpixel, the second subpixel, or the third subpixel. Each of the first, second, and third light emitting elements may include respective first, second, and third light emitting layers configured to emit light of an emission spectrum corresponding to the first, second, and third colors, respectively, the light absorption sensor may include a light absorbing layer including a p-type semiconductor and an n-type semiconductor forming a pn junction and is configured to absorb light reflected by a recognition target and convert the reflected light into an electrical signal. Respective sublimation temperatures of the organic materials included in the first, second, and third light emitting layers and the n-type semiconductor may be each less than or equal to about 390° C., respectively, wherein the sublimation temperature of each given organic material and the n-type semiconductor is a temperature at which a weight reduction of 10% relative to an initial weight of the given organic material and the n-type semiconductor occurs during thermogravimetric analysis under an ambient pressure of about 10 Pa or less, and a difference in sublimation temperatures between the organic materials included in the first, second, and third light emitting elements and the n-type semiconductors is about 0° C. to about 150° C.

The first, second, and third light emitting elements and the light absorption sensor may each include a separate portion of a common electrode configured to apply a common voltage to the first, second, and third light emitting elements and the light absorption sensor, and a separate portion of a first common auxiliary layer between the first, second, and third light emitting layers and the common electrode and between the light absorption layer and the common electrode. A LUMO energy level of the first common auxiliary layer may be between the LUMO energy level of each separate light emitting layer of the first, second, and third light emitting layers and a work function of the common electrode, and a difference between the LUMO energy level of the first common auxiliary layer and a LUMO energy level of the n-type semiconductor may be about 0 eV to about 1.2 eV.

The n-type semiconductor may be represented by Chemical Formula 1, and the p-type semiconductor may be represented by Chemical Formula 2.

The n-type semiconductor may be represented by Chemical Formula 1A or 1B.

The p-type semiconductor may be represented by Chemical Formula 2A or 2B.

According to some example embodiments, an electronic device including the sensor-embedded display panel is provided.

According to some example embodiments, a light absorption sensor includes a pair of electrodes, and a light absorbing layer between the pair of electrodes, wherein the light absorbing layer includes a p-type semiconductor configured to selectively absorb light of any one of a red wavelength spectrum, a green wavelength spectrum, a blue wavelength spectrum, or an infrared wavelength spectrum, and an n-type semiconductor that forms a pn junction with the p-type semiconductor, wherein the n-type semiconductor is represented by Chemical Formula 1A or 1B.

The p-type semiconductor may be represented by Chemical Formula 2.

The p-type semiconductor may be represented by Chemical Formula 2A or 2B.

An electronic device including the light absorption sensor is provided.

According to some example embodiments, a light absorption sensor, may include a pair of electrodes; and a light absorbing layer between the pair of electrodes. The light absorbing layer may include a first organic material and a second organic material that forms a pn junction with the first organic material. A difference between respective sublimation temperatures of the first organic material and the second organic material is about 0° C. to about 150° C., wherein each sublimation temperature of each given organic material is a temperature at which a weight reduction of 10% relative to an initial weight of the given organic material occurs during thermogravimetric analysis under an ambient pressure of about 10 Pa or less.

the first organic material may be represented by Chemical Formula 1, and the second organic material may be represented by Chemical Formula 2.

A sensor-embedded display panel may include a substrate, a light emitting element on the substrate, the light emitting element including a light emitting layer; and the light absorption sensor on the substrate, wherein the light absorbing layer of the light absorption sensor is arranged in parallel with the light emitting layer along an in-plane direction of the substrate such that the light absorbing layer and the light emitting layer at least partially overlap in the in-plane direction, wherein the light absorbing layer is configured to absorb light of a red wavelength spectrum, a green wavelength spectrum, a blue wavelength spectrum, or any combination thereof, wherein the light emitting layer includes a third organic material, and wherein a difference between respective sublimation temperatures of two materials of the first organic material, the second organic material, or the third organic material is about 0° C. to about 150° C.

An electronic device may include the light absorption sensor.

A sensor having high performance while improving design and usability may be realized by being integrated with the display panel.

DETAILED DESCRIPTION

Figure 1:
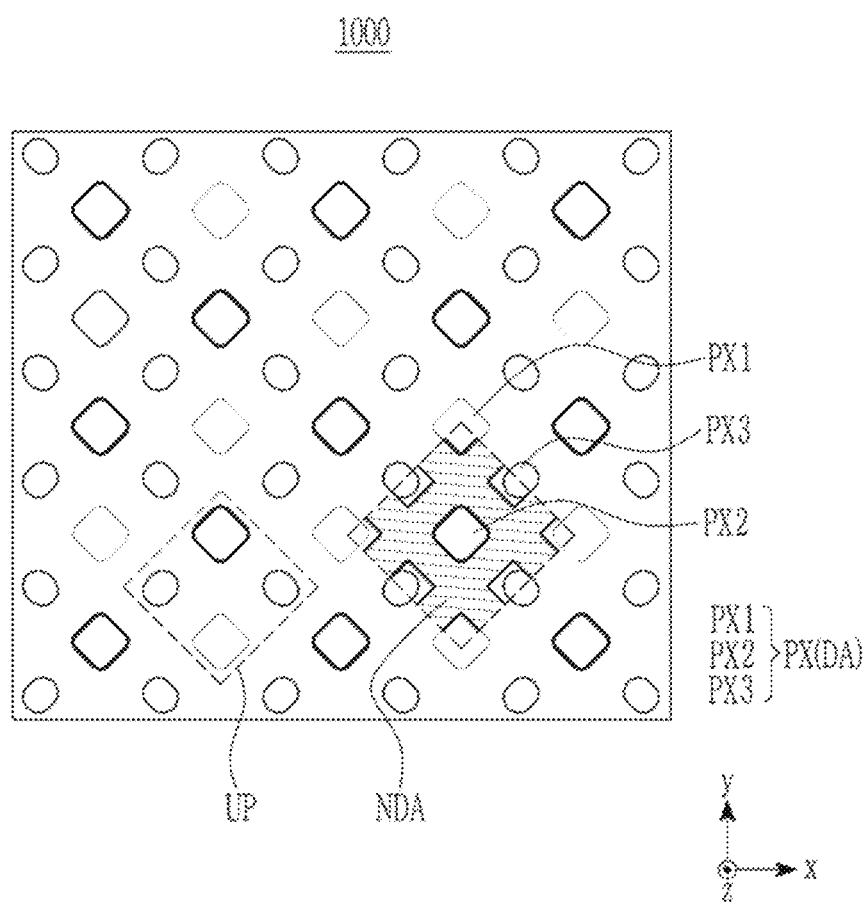
FIG. 1 is a plan view showing an example of a sensor-embedded display panel according to some example embodiments.

Hereinafter, some example embodiments are described in detail so that those skilled in the art can easily implement them. However, the actual applied structure may be implemented in various different forms and is not limited to the implementations described herein.

In the drawings, the thickness of layers, films, panels, regions, etc., are exaggerated for clarity. It will be understood that when an element such as a layer, film, region, or substrate is referred to as being "on" another element, it may be directly on the other element or intervening elements may also be present. In contrast, when an element is referred to as being "directly on" another element, there are no intervening elements present.

Parts having no relationship with the description are omitted for clarity, and the same or similar constituent elements are indicated by the same reference numeral throughout the specification.

Hereinafter, the terms "lower portion" and "upper portion" are used for better understanding and ease of description, but do not limit the position relationship.

As used herein, when a definition is not otherwise provided, "substituted" refers to a compound or a group wherein at least one of hydrogen atoms thereof is replaced by a substituent selected from a halogen, a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C30 alkyl group, a C2 to C30 alkenyl group, a C2 to C30 alkynyl group, a C6 to C30 aryl group, a C7 to C30 arylalkyl group, a C1 to C30 alkoxy group, a C1 to C20 heteroalkyl group, a C3 to C20 heterocyclic group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and any combination thereof.

As used herein, when a definition is not otherwise provided, "hetero" refers to one including 1 to 4 heteroatoms of N, O, S, Se, Te, Si, and P.

As used herein, when a definition is not otherwise provided, an energy level is a highest occupied molecular orbital (HOMO) energy level or a lowest unoccupied molecular orbital (LUMO) energy level.

As used herein, when a definition is not otherwise provided, a work function or an energy level is expressed as an absolute value from a vacuum level. In addition, when the work function or the energy level is referred to be deep, high, or large, it may have a large absolute value based on "0 eV" of the vacuum level while when the work function or the energy level is referred to be shallow, low, or small, it may have a small absolute value based on "0 eV" of the vacuum level. Also, the difference between the work function and/or the energy level may be a value obtained by subtracting a small absolute value from a large absolute value.

As used herein, when a definition is not otherwise provided, the HOMO energy level may be evaluated by an amount of photoelectrons emitted according to energy obtained by irradiating UV light on a thin film using AC-2 (Hitachi) or AC-3 (Riken Keiki Co., LTD.).

As used herein, when a definition is not otherwise provided, the LUMO energy level is obtained by measuring the energy bandgap using a UV-Vis spectrometer (Shimadzu Corporation), and then calculating the LUMO energy level from the energy bandgap and the already measured HOMO energy level.

It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., +10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

Hereinafter, a sensor-embedded display panel according to some example embodiments is described.

A sensor-embedded display panel according to some example embodiments may be a display panel capable of performing a display function and a recognition function (e.g., a biometric recognition function) and may be an in-cell type display panel in which a sensor configured to perform a recognition function (e.g., a biometric recognition function) is embedded in the display panel.

Figure 2:
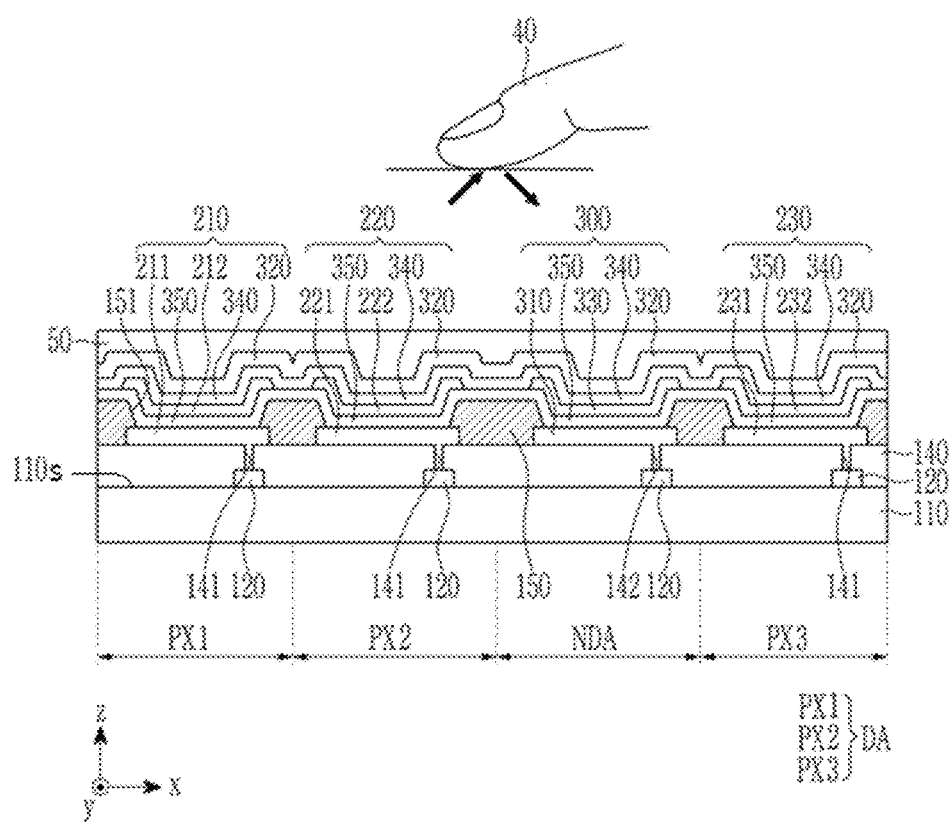
FIG. 2 is a cross-sectional view illustrating an example of a sensor-embedded display panel according to some example embodiments.

FIG. 1 is a plan view showing an example of a sensor-embedded display panel according to some example embodiments, and FIG. 2 is a cross-sectional view illustrating an example of a sensor-embedded display panel according to some example embodiments.

Referring to FIGS. 1 and 2, the sensor-embedded display panel 1000 according to some example embodiments includes a plurality of subpixels PX displaying (e.g., configured to display) different colors. The plurality of subpixels PX may display at least three primary colors, and may include, for example, the first subpixel PX1 displaying a first color, a second subpixel PX2 displaying a second color, and a third subpixel PX3 displaying a third color, the first, second, and third colors being different from each other and selected from red, green, and blue. For example, the first color, the second color, and the third color may be red, green, and blue, respectively. The first subpixel PX1 may be a red subpixel displaying red, and the second subpixel PX2 may be a green subpixel displaying green, and the third subpixel PX3 may be a blue subpixel displaying blue. However, the present inventive concepts are not limited thereto and may further include an auxiliary subpixel (not shown) such as a white subpixel. Displaying a color may refer to emitting light corresponding to the color (e.g., light in a wavelength spectrum of the color). Referring to FIG. 1, the sensor embedded display panel 1000 may include a plurality of first sub-pixels (PX1) configured to display a red color (e.g., light of a red wavelength spectrum) and including a first light emitting element (e.g., the first light emitting element 210 shown in FIG. 2), a plurality of second sub-pixels (PX2) configured to display a green color (e.g., light of a green wavelength spectrum) and including a second light emitting element (e.g., the second light emitting element 220 shown in FIG. 2), and a plurality of third sub-pixels (PX3) configured to display a blue color (e.g., light of a blue wavelength spectrum) and including a third light emitting element (e.g., the third light emitting element 230 shown in FIG. 2), where the first sub-pixels (PX1), the second sub-pixels (PX2), and the third sub-pixels (PX3) are located in and/or at least partially define the display area (DA).

The plurality of subpixels PX including the first subpixel PX1, the second subpixel PX2, and the third subpixel PX3 may constitute (e.g., may define) one unit pixel UP and may be arranged repeatedly along a row and/or column. In FIG. 1, a structure including one first subpixel PX1, two second subpixels PX2, and one third subpixel PX3 in the unit pixel UP is illustrated as an example, but the present inventive concepts are not limited thereto. At least one first subpixel PX1, at least one second subpixel PX2, and at least one third subpixel PX3 may be included in each unit pixel UP. Although the drawing shows a Pentile type arrangement as an example, the arrangement is not limited thereto and the arrangement of the subpixels PX may be varied. An area occupied by the plurality of subpixels PX and configured to display at least one color by the plurality of subpixels PX may be a display area DA for displaying an image. For example, the area (e.g., in the xy plane) of the sub-pixels (PX) may collectively define the display area (DA) that is configured to display an image thereon (e.g., configured to display one or more colors). A portion of the area (e.g., in the xy plane) of the sensor embedded display panel 1000 that excludes the display area (DA) may be a non-display area (NDA) that is configured to not display an image thereon (e.g., configured to not display any color).

Each of the first subpixel PX1, the second subpixel PX2, and the third subpixel PX3 may include a light emitting element. For example, the first subpixel PX1 may include a first light emitting element 210 configured to emit light having a wavelength spectrum of a first color, the second subpixel PX2 may include a second light emitting element 220 configured to emit light having a wavelength spectrum of a second color, and the third subpixel PX3 may include a third light emitting element 230 configured to emit light having a wavelength spectrum of a third color. However, the present inventive concepts are not limited thereto, and at least one of the first subpixel PX1, the second subpixel PX2, or the third subpixel PX3 may include a light emitting element configured to emit light of a combination of the first color, the second color, and the third color, that is, light in a white wavelength spectrum, and may display the first color, the second color, or the third color through a color filter (not shown).

The sensor-embedded display panel 1000 according to some example embodiments includes a light absorption sensor 300. The light absorption sensor 300 may be in a non-display area NDA. The non-display area NDA is an area excluding the display area DA (e.g., a portion of the total area of the sensor embedded display panel 1000 that excludes the display area (DA)), in which the first subpixel PX1, the second subpixel PX2, the third subpixel PX3, and optionally the auxiliary subpixel are not disposed. The light absorption sensor 300 may be between at least two of the first subpixel PX1 (e.g., a first sub-pixel (PX1) of the plurality of first sub-pixels (PX1)), the second subpixel PX2 (e.g., a second sub-pixel (PX2) of the plurality of second sub-pixels (PX2)), or the third subpixel PX3 (e.g., a third sub-pixel (PX3) of the plurality of third sub-pixels (PX3)) in the in-plane direction of the substrate 110 (e.g., the xy direction), and may be in parallel with the first, the second, and third light emitting elements 210, 220, and 230 in the display area DA, for example in parallel along the in-plane direction of the substrate 110 (e.g., the xy direction as shown).

The light absorption sensor 300 may be an optical type recognition sensor (e.g., a biometric sensor), and may be configured to absorb light emitted from at least one of the first, second, or third light emitting elements 210, 220, and 230 in the display area DA and then reflected by a recognition target 40 such as a living body, a tool, or an object (e.g., may be configured to absorb light of a red wavelength spectrum, a green wavelength spectrum, a blue wavelength spectrum, or any combination thereof), and then convert the reflected light into an electrical signal. Here, the living body may be a finger, a fingerprint, a palm, an iris, a face, and/or a wrist, but is not limited thereto. The light absorption sensor 300 may be, for example, a fingerprint sensor, an illumination sensor, an iris sensor, a depth sensor, a blood vessel distribution sensor, and/or a heart rate sensor, but is not limited thereto.

The light absorption sensor 300 may be at the same plane as the first, second, and third light emitting elements 210, 220, and 230 on the substrate 110, and may be embedded in the display panel 1000. Restated, the light absorption sensor 300 may be arranged in parallel with the first, second, and third light emitting elements 210, 220, and 230 on the substrate 110 along an in-plane direction of the substrate 110. As described herein, the in-plane direction of the substrate 110 may be a direction (e.g., the xy direction as shown) that extends in parallel with at least a portion of the substrate 110, including an upper surface 110S of the substrate 110.

Referring to FIG. 2, the sensor-embedded display panel 1000 may include a substrate 110; a thin film transistor 120 formed on the substrate 110; an insulating layer 140 formed on the thin film transistor 120; a pixel definition layer 150 formed on the insulating layer 140; and the first, second, or third light emitting elements 210, 220, and 230 and the light absorption sensor 300 in a space partitioned by the pixel definition layer 150.

The substrate 110 may be a light-transmitting substrate, for example, a glass substrate or a polymer substrate. The polymer substrate may include, for example, polycarbonate, polymethyl methacrylate, polyethylene terephthalate, polyethylene naphthalate, polyimide, polyamide, polyamideimide, polyethersulfone, polyorganosiloxane, styrene-ethylene-butylene-styrene copolymer, polyurethane, polyacryl, polyolefin, or any combination thereof, but is not limited thereto.

The plurality of thin film transistors 120 are formed on the substrate 110. One or two or more thin film transistors 120 may be included in each subpixel PX, and may include, for example, at least one switching thin film transistor and/or at least one driving thin film transistor. The substrate 110 on which the thin film transistor 120 is formed may be referred to as a thin film transistor substrate or a thin film transistor backplane.

The insulating layer 140 may cover the substrate 110 and the thin film transistor 120, and may be formed on the whole surface of the substrate 110. The insulating layer 140 may be a planarization layer or a passivation layer, and may include an organic insulating material, an inorganic insulating material, an organic-inorganic insulating material, or any combination thereof. The insulating layer 140 may have a plurality of contact holes 141 for electrically connecting the first, second, and third light emitting elements 210, 220, and 230 and the thin film transistor 120, and a plurality of contact holes 142 for electrically connecting the light absorption sensor 300 and the thin film transistor 120. The insulation layer 140 may include an organic, inorganic, or organic-inorganic insulating material, in some example embodiments, an inorganic insulating material such as silicon oxide, silicon nitride, silicon oxynitride, aluminum oxide, aluminum nitride, or aluminum oxynitride; an organic insulating material such as polyimide, polyamide, polyamideimide, or polyacrylate; or an organic-inorganic insulating material such as polyorganosiloxane or polyorganosilazane.

A pixel definition layer 150 may also be formed on the whole surface (e.g., entire upper surface 110S) of the substrate 110, and may be between adjacent subpixels PX (e.g., in the xy direction as shown in FIG. 2) to partition each subpixel PX. The pixel definition layer 150 may have and/or define a plurality of openings 151 in each subpixel PX, and any one of the first, second, and third light emitting elements 210, 220, and 230 and the light absorption sensor 300 may be disposed in the opening 151. The pixel definition layer 150 may be an insulation layer that may include an organic, inorganic, or organic-inorganic insulating material, in some example embodiments, an inorganic insulating material such as silicon oxide, silicon nitride, silicon oxynitride, aluminum oxide, aluminum nitride, or aluminum oxynitride; an organic insulating material such as polyimide, polyamide, polyamideimide, or polyacrylate; or an organic-inorganic insulating material such as polyorganosiloxane or polyorganosilazane.

The first, second, and third light emitting elements 210, 220, and 230 are formed on the substrate 110 (or the thin film transistor substrate) and are repeatedly arranged along an in-plane direction (e.g., xy direction) of the substrate 110. As described above, the first, second, and third light emitting elements 210, 220, and 230 may be included in the first subpixel PX1, the second subpixel PX2, and the third subpixel PX3, respectively. The first, second, and third light emitting elements 210, 220, and 230 may be electrically connected to separate thin film transistors 120 to be independently driven.

The first, second, and third light emitting elements 210, 220, and 230 may be each independently configured to emit one light of a red wavelength spectrum, a green wavelength spectrum, a blue wavelength spectrum, and any combination thereof. For example, the first light emitting element 210 may be configured to emit light of a red wavelength spectrum, the second light emitting element 220 may be configured to emit light of a green wavelength spectrum, and the third light emitting element 230 may be configured to emit light of a blue wavelength spectrum. Herein, the red wavelength spectrum, the green wavelength spectrum, and the blue wavelength spectrum may each have a maximum emission wavelength (λmax) of greater than about 600 nm and less than about 750 nm, about 500 nm to about 600 nm, and greater than or equal to about 400 nm and less than about 500 nm.

The first, second, and third light emitting elements 210, 220, and 230 may be, for example, light emitting diodes, for example, organic light emitting diodes OLEDs including organic materials.

The light absorption sensor 300 may be formed on the substrate 110 (or the thin film transistor substrate), and may be randomly or regularly arranged along an in-plane direction (e.g., xy direction) of the substrate 110. As described above, the light absorption sensor 300 may be in the non-display area NDA, and may be connected to a separate thin film transistor 120 to be independently driven. The light absorption sensor 300 may be configured to absorb light of the same wavelength spectrum as light emitted from at least one of the first, second, or third light emitting elements 210, 220, and 230 and convert it into an electrical signal. For example, the light absorption sensor 300 may be configured to absorb light of the red wavelength spectrum, the green wavelength spectrum, the blue wavelength spectrum, or any combination thereof and convert it into an electrical signal. The light absorption sensor 300 may be, for example, a photoelectric diode, for example, an organic photoelectric diode including an organic material.

Each of the first, second, and third light emitting elements 210, 220, and 230 and the light absorption sensor 300 may include pixel electrodes 211, 221, 231, and 310; a common electrode 320 facing the pixel electrodes 211, 221, 231, and 310 to which a common voltage is applied; light emitting layers 212, 222, and 232 or the light absorbing layer 330, the first common auxiliary layer 340, and the second common auxiliary layer 350 which are between the pixel electrodes 211, 221, 231, and 310 and the common electrode 320.

The first, second, and third light emitting elements 210, 220, and 230 and the light absorption sensor 300 may be arranged in parallel along an in-plane direction (e.g., xy direction) of the substrate 110, and may share the common electrode 320, the first common auxiliary layer 340, and the second common auxiliary layer 350 formed on the whole surface.

The common electrode 320 may be continuously formed as a single piece of material that extends on the light emitting layers 212, 222, and 232 and the light absorbing layer 330, and may be substantially formed on the whole surface of the substrate 110. The common electrode 320 may apply a common voltage to the first, second, and third light emitting elements 210, 220, and 230 and the light absorption sensor 300. As shown, the first, second, and third light emitting elements 210, 220, and 230 and the light absorption sensor 300 may include separate portions of a single common electrode 320 that is a single piece of material that extends on each of the respective light emitting layers 212, 222, and 232 and the light absorbing layer 330 and between the first, second, and third light emitting elements 210, 220, and 230 and the light absorption sensor 300.

The first common auxiliary layer 340 may be between the light emitting layers 212, 222, and 232 and the light absorbing layer 330 and the common electrode 320, and may be continuously formed as a single piece of material that extends on the light emitting layers 212, 222, and 232 and the light absorbing layer 330, and under the common electrode 320. As shown, the first, second, and third light emitting elements 210, 220, and 230 and the light absorption sensor 300 may include separate portions of a single first common auxiliary layer 340 that is a single piece of material that extends on each of the respective light emitting layers 212, 222, and 232 and the light absorbing layer 330 and between the first, second, and third light emitting elements 210, 220, and 230 and the light absorption sensor 300.

The first common auxiliary layer 340 may be a charge auxiliary layer (e.g., an electron auxiliary layer) that facilitates injection and/or transport of charge carriers (e.g., electrons) from the common electrode 320 to the light emitting layers 212, 222, and 232. For example, the LUMO energy level of the first common auxiliary layer 340 may be between the LUMO energy level of the light emitting layers 212, 222, and 232 and the work function of the common electrode 320. The LUMO energy level of the first common auxiliary layer 340 and the LUMO energy levels of the light emitting layers 212, 222, and 232 may become sequentially shallower (e.g., sequentially smaller in relation to a vacuum level (e.g., 0 eV)). On the other hand, the LUMO energy level of the first common auxiliary layer 340 may be shallower than the LUMO energy level of the light absorbing layer 330 and the work function of the common electrode 320, respectively.

The first common auxiliary layer 340 may include an organic material, an inorganic material, an organic-inorganic material, or any combination thereof satisfying the LUMO energy level, for example, metal halides such as LiF, NaCl, CsF, RbCl, and RbI; lanthanide metals such as Yb; metal oxides such as $Li_2O$ and BaO; Liq (lithium quinolate), Alq3 (tris(8-hydroxyquinolinato)aluminum), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-ylphenyl)-9,10-dinaphthylanthracene, TPBi (1,3,5-tri(1-phenyl-1H-benzo[d]imidazol-2-yl)phenyl), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tertbutylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,O8)-(1,1'-biphenyl-4-olato)aluminum)), Bebq2 (berylliumbis(benzoquinolin-10-olate), AND (9,10-di(naphthalene-2-yl)anthracene), BmPyPhB (1,3-bis[3,5-di(pyridin-3-yl)phenyl]benzene), or any combination thereof, but is not limited thereto. The first common auxiliary layer 340 may have one or two or more layers.

The second common auxiliary layer 350 may be between the light emitting layers 212, 222, and 232 and the light absorbing layer 330 and the substrate 110, and among them, the second common auxiliary layer 350 may be between the light emitting layers 212, 222, and 232 and the light absorbing layer 330, and the pixel electrodes 211, 221, 231, and 310. The second common auxiliary layer 350 may be continuously formed as a single piece of material that extends under the light emitting layers 212, 222, and 232 and the light absorbing layer 330, and on the pixel electrodes 211, 221, 231, and 310. As shown, the first, second, and third light emitting elements 210, 220, and 230 and the light absorption sensor 300 may include separate portions of a single second common auxiliary layer 350 that is a single piece of material that extends under each of the respective light emitting layers 212, 222, and 232 and the light absorbing layer 330 and between the first, second, and third light emitting elements 210, 220, and 230 and the light absorption sensor 300.

The second common auxiliary layer 350 is a charge auxiliary layer (e.g., hole auxiliary layer) that facilitates injection and/or transport of charge carriers (e.g., holes) from the pixel electrodes 211, 221, and 231 to the light emitting layers 212, 222, and 232. For example, the HOMO energy level of the second common auxiliary layer 350 may be between the HOMO energy levels of the light emitting layers 212, 222, and 232 and the work functions of the pixel electrodes 211, 221, and 231. The work functions of the pixel electrodes 211, 221, and 231, the HOMO energy level of the second common auxiliary layer 350, and the HOMO energy levels of the light emitting layers 212, 222, and 232 may become sequentially deeper (e.g., sequentially larger in relation to 0 eV of a vacuum level).

The second common auxiliary layer 350 may include an organic material, an inorganic material, an organic-inorganic material, or any combination thereof satisfying the HOMO energy level, and may include, for example, a phthalocyanine compounds such as copper phthalocyanine; DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino] triphenylamine), TDATA (4,4'4"-tris(N,N-diphenylamino)triphenylamine), 4,4',4"-tris {N-(2-naphthyl)-N-phenylamino}-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/camphor sulfonic acid), PANI/PSS (polyaniline/poly(4-styrenesulfonate)), NPB (N,N'-di(naphthalene-I-yl)-N,N'-diphenylbenzidine), polyetherketone including triphenylamine (TPAPEK), 4-isopropyl-4'-methyldiphenyliodonium[tetrakis(pentafluorophenyl) borate], HAT-CN (dipyrazino[2,3-f: 2',3'-h]quinoxaline-2,3,6,7,10,11-hexacarbonitrile), N-phenylcarbazole, a carbazole derivative such as polyvinylcarbazole, a fluorine-based derivative, a triphenylamine-based derivative such as TPD (N,N'-bis(3-methylphenyl)-N,N'-diphenyl-[1, 1-biphenyl]-4,4'-diamine) and TCTA (4,4',4"-tris(N-carbazolyl)triphenylamine), NPB (N,N'-di(naphthalene-I-yl)-N, N'-diphenyl-benzidine), TAPC (4,4'-cyclohexylidene bis[N, N-bis(4-methylphenyl)benzenamine]), HMTPD (4,4'-bis[N, N'-(3-tolyl)amino]-3,3'-dimethylbiphenyl), mCP (1,3-bis(N-carbazolyl)benzene), or any combination thereof, but is not limited thereto. The second common auxiliary layer 350 may have one or two or more layers.

Each of the first, second, and third light emitting elements 210, 220, and 230 and the light absorption sensor 300 includes pixel electrodes 211, 221, 231, and 310 facing the common electrode 320. One of the pixel electrodes 211, 221, 231, and 310 or the common electrode 320 is an anode, and the other is a cathode. For example, the pixel electrodes 211, 221, 231, and 310 may be an anode, and the common electrode 320 may be a cathode. The pixel electrodes 211, 221, 231, and 310 are separated for each subpixel PX, and may be electrically connected to a separate thin film transistor 120 to be independently driven.

The pixel electrodes 211, 221, 231, and 310 and the common electrode 320 may each be a light-transmitting electrode or a reflective electrode, and for example, at least one of the pixel electrodes 211, 221, 231, and 310 or the common electrode 320 may be a light-transmitting electrode.

The light-transmitting electrode may be a transparent electrode or a transflective electrode. The transparent electrode may have a transmittance of greater than or equal to about 85%, greater than or equal to about 90%, or greater than or equal to about 95%, and the transflective electrode may have a transmittance of greater than or equal to about 30% and less than about 85%, about 40% to about 80%, or about 40% to about 75%. The transparent electrode and the transflective electrode may include, for example, at least one of an oxide conductor, a carbon conductor, or a metal thin film. The oxide conductor may include, for example, one or more selected from indium tin oxide (ITO), indium zinc oxide (IZO), zinc tin oxide (ZTO), aluminum tin oxide (ATO), and aluminum zinc oxide (AZO), the carbon conductor may include one or more selected from graphene and a carbon nano-body, and the metal thin film may include aluminum (Al), magnesium (Mg), silver (Ag), gold (Au), magnesium-silver (Mg—Ag), magnesium-aluminum (Mg—Al), an alloy thereof, or any combination thereof.

The reflective electrode may include a reflective layer having a transmittance of less than or equal to about 5% and/or a reflectance of greater than or equal to about 80%, and the reflective layer may include an optically opaque material. The optically opaque material may include a metal, a metal nitride, or any combination thereof, such as silver (Ag), copper (Cu), aluminum (Al), gold (Au), titanium (Ti), chromium (Cr), nickel (Ni), an alloy thereof, a nitride thereof (e.g., TiN), or any combination thereof, but is not limited thereto. The reflective electrode may be made of a reflective layer or may have a laminated structure of a reflective layer/transmissive layer or a transmissive layer/reflective layer/transmissive layer, and the reflective layer may have one or two or more layers.

For example, when the pixel electrodes 211, 221, 231, and 310 are light-transmitting electrodes and the common electrode 320 is a reflective electrode, the sensor-embedded display panel 1000 may be a bottom emission type display panel configured to emit light toward the substrate 110. For example, when the pixel electrodes 211, 221, 231, and 310 are reflective electrodes and the common electrode 320 is a light-transmitting electrode, the sensor-embedded display panel 1000 may be a top emission type display panel configured to emit light toward the opposite side of the substrate 110. For example, when the pixel electrodes 211, 221, 231, and 310 and the common electrode 320 are light-transmitting electrodes, the sensor-embedded display panel 1000 may be a both side emission type display panel configured to emit light toward both the substrate 110 and the opposite side of the substrate 110.

For example, the pixel electrodes 211, 221, 231, and 310 may be reflective electrodes and the common electrode 320 may be a transflective electrode. In this case, the sensor-embedded display panel 1000 may form a microcavity structure. In the microcavity structure, the light may be repeatedly reflected between the reflective electrode and the transflective electrode spaced apart by a particular (or, alternatively, predetermined) optical length (e.g., the distance between the transflective electrode and the reflective electrode) to enhance light of a particular (or, alternatively, predetermined) wavelength spectrum and to improve optical properties.

For example, among the light emitted from the light emitting layers 212, 222, and 232 of the first, second, and third light emitting elements 210, 220, and 230, light having a particular (or, alternatively, predetermined) wavelength spectrum may be modified by being repeatedly reflected between the transflective electrode and the reflective electrode. The light of the wavelength spectrum corresponding to the resonance wavelength of the microcavity among the modified light may be enhanced to exhibit amplified emission characteristics in a narrow wavelength spectrum. Accordingly, the sensor-embedded display panel 1000 may express a color with high color purity.

For example, light of a particular (or, alternatively, predetermined) wavelength spectrum among the light incident on the light absorption sensor 300 may be modified by being repeatedly reflected between the transflective electrode and the reflective electrode. The light of the wavelength spectrum corresponding to the resonance wavelength of the microcavity among the modified light may be enhanced to exhibit amplified photoelectric conversion characteristics in a narrow wavelength spectrum. Accordingly, the light absorption sensor 300 may exhibit high photoelectric conversion characteristics in a narrow wavelength spectrum.

Each of the first, second, and third light emitting elements 210, 220, and 230 includes the light emitting layers 212, 222, and 232 between the pixel electrodes 211, 221, and 231 and the common electrode 320. The light emitting layer 212 included in the first light emitting element 210, the light emitting layer 222 included in the second light emitting element 220, and the light emitting layer 232 included in the third light emitting element 230 may be configured to emit a spectrum of light of the same or different wavelength spectra, and for example light in a red wavelength spectrum, a green wavelength spectrum, a blue wavelength spectrum, or any combination thereof.

For example, when the first light emitting element 210, the second light emitting element 220, and the third light emitting element 230 are a red light emitting element, a green light emitting element, and a blue light emitting element, respectively, the light emitting layer 212 included in the first light emitting element 210 may be a red light emitting layer configured to emit light of a red wavelength spectrum, and the light emitting layer 222 included in the second light emitting element 220 may be a green light emitting layer configured to emit light of a green wavelength spectrum, and the light emitting layer 232 included in the third light emitting element 230 may be a blue light emitting layer configured to emit light of a blue wavelength spectrum. Herein, the red wavelength spectrum, the green wavelength spectrum, and the blue wavelength spectrum may have a maximum emission wavelength in greater than about 600 nm and less than about 750 nm, about 500 nm to about 600 nm, and greater than or equal to about 380 nm (e.g., greater than or equal to about 400 nm) and less than about 500 nm, respectively.

For example, when at least one of the first light emitting element 210, the second light emitting element 220, or the third light emitting element 230 is a white light emitting element, the light emitting layer of the white light emitting element may be configured to emit light of a full visible wavelength spectrum. For example, the white light emitting element may be configured to emit light in a wavelength spectrum of greater than or equal to about 380 nm and less than about 750 nm, about 400 nm to about 700 nm, or about 420 nm to about 700 nm.

The light emitting layers 212, 222, and 232 may include at least one host material and a fluorescent or phosphorescent dopant, and at least one of the at least one host material and the fluorescent or phosphorescent dopant may be an organic material. The organic material may include, for example, a low molecular weight organic material, for example a depositable organic material.

The light absorption sensor 300 may include a light absorbing layer 330 between the pixel electrode 310 and the common electrode 320. The light absorbing layer 330 may be in parallel with the light emitting layers 212, 222, and 232 of the first, second and third light emitting elements 210, 220, 230 along an in-plane direction (e.g., xy direction) of the substrate 110. In some embodiments, the light absorbing layer 330 and the light emitting layers 212, 222, and 232 may be on the same plane. For example, as shown in at least FIG. 2, the light absorbing layer 330 of the light absorption sensor 300 and the light emitting layers 212, 222, and 232 of the first, second, and third light emitting elements 210, 220, and 230 may at least partially overlap with each other (e.g., partially or completely overlap each other) in the in-plane direction (e.g., xy direction) of the substrate 110, which may be understood to be a horizontal direction that extends in parallel to an in-plane direction of the substrate 110 as shown in FIG. 2 and/or a horizontal direction that extends in parallel to an upper surface 110S of the substrate 110 as shown in FIG. 2, and the light absorbing layer 330 and the light emitting layers 212, 222, and 232 may be at least partially positioned on the same plane (e.g., an xy plane extending in the xy direction that intersects each of the light absorbing layer 330 and the light emitting layers 212, 222, and 232).

The light absorbing layer 330 may be a photoelectric conversion layer configured to absorb light of a particular (or, alternatively, predetermined) wavelength spectrum and convert light into an electrical signal. The light absorbing layer 330 may be configured to absorb light generated by reflection of light emitted from at least one of the aforementioned first, second, or third light emitting elements 210, 220, and 230, by the recognition target 40 and may convert the reflected light into an electrical signal. The light absorbing layer 330 may be configured to absorb light of, for example, a red wavelength spectrum, a green wavelength spectrum, a blue wavelength spectrum, an infrared wavelength spectrum, or any combination thereof.

For example, the light absorbing layer 330 may be configured to selectively absorb light of a red wavelength spectrum having a maximum absorption wavelength greater than about 600 nm and less than about 750 nm. The light absorbing layer 330 may be configured to absorb light obtained by reflection of the light emitted from the red light emitting element among the first, second, and third light emitting elements 210, 220, and 230, by the recognition target 40.

For example, the light absorbing layer 330 may be configured to selectively absorb light of a green wavelength spectrum having a maximum absorption wavelength of about 500 nm to about 600 nm. The light absorbing layer 330 may be configured to absorb light obtained by reflection of the light emitted from the green light emitting element among the first, second, and third light emitting elements 210, 220, and 230, by the recognition target 40.

For example, the light absorbing layer 330 may be configured to selectively absorb light of a blue wavelength spectrum having a maximum absorption wavelength of greater than or equal to about 380 nm and less than about 500 nm, and the first, second, and third light emitting elements 210, 220, and 230. The light absorbing layer 330 may be configured to absorb light obtained by reflection of the light emitted from the blue light emitting element, by the recognition target 40.

For example, the light absorbing layer 330 may be configured to absorb light of a red wavelength spectrum, a green wavelength spectrum, and a blue wavelength spectrum, that is, light of a full visible wavelength spectrum of greater than or equal to about 380 nm and less than about 750 nm. The light absorbing layer 330 may be configured to absorb light obtained by reflection of a combination of the light emitted from the first, second, and third light emitting elements 210, 220, and 230, by the recognition target 40.

The light absorbing layer 330 may include a p-type semiconductor and/or an n-type semiconductor for photoelectric conversion of the absorbed light. The p-type semiconductor and the n-type semiconductor may form a pn junction, generate excitons by receiving light from the outside, and then separate the generated excitons into holes and electrons. Each of the p-type semiconductor and the n-type semiconductor may be one or two or more, and at least one of the p-type semiconductor or the n-type semiconductor may be a light absorbing material configured to absorb light of at least a portion of a wavelength spectrum of visible light. For example, any one of the p-type semiconductor and the n-type semiconductor may be a light absorbing material configured to absorb light of at least a portion of the visible wavelength spectrum, and the other of the p-type semiconductor and the n-type semiconductor may be a transparent material that does not substantially absorb light of a visible wavelength spectrum. The transparent material may have a wide energy bandgap so as not to substantially absorb light in the visible wavelength spectrum, for example, may have an energy bandgap of greater than or equal to about 2.5 eV. The energy bandgap of the transparent material may be, for example, about 2.5 eV to about 6.0 eV within the above range.

For example, the p-type semiconductor may be a light absorbing material configured to absorb light of at least a portion of a wavelength spectrum of visible light, and the n-type semiconductor may be a transparent material. For example, the p-type semiconductor may be a light absorbing material configured to absorb light in the full visible wavelength spectrum, and the n-type semiconductor may be a transparent material. For example, the p-type semiconductor may be a light absorbing material configured to selectively absorb light in any one or two of a red wavelength spectrum, a green wavelength spectrum, or a blue wavelength spectrum, and the n-type semiconductor may be a transparent material.

The light absorbing layer 330 may include an organic material, and at least one of the p-type semiconductor or the n-type semiconductor may be an organic material. For example, at least one of the p-type semiconductor or the n-type semiconductor may include a low molecular weight organic material, for example, a depositable organic material. For example, the p-type semiconductor and the n-type semiconductor may each be a low molecular weight organic material, for example, each may be a depositable organic material.

As described above, the light absorbing layer 330 may be in parallel with the light emitting layers 212, 222, and 232 along the in-plane direction (e.g., xy direction) of the substrate 110, and the light absorbing layer 330 may be in the same plane as the light emitting layers 212, 222, and 232. For example, the organic material included in the light emitting layers 212, 222, and 232 (hereinafter referred to as a "first organic material") and the organic material included in the light absorbing layer 330 (hereinafter referred to as a "second organic material") may each be a low molecular weight organic material and may be a depositable organic material.

The first organic material may be one of at least one host material or a fluorescent or phosphorescent dopant included in the light emitting layers 212, 222, and 232, and the second organic material may be one of a p-type semiconductor or an n-type semiconductor. For example, the first organic material may be one of at least one host material or a fluorescent or phosphorescent dopant included in the light emitting layers 212, 222, and 232, and the second organic material may be an n-type semiconductor. For example, the first organic material may be one of at least one host material or a fluorescent or phosphorescent dopant included in the light emitting layers 212, 222, and 232, and the second organic material may be a transparent n-type semiconductor material having, for example, an energy bandgap of greater than or equal to about 2.5 eV.

For example, each of the first organic material and the second organic material may be an organic material that may be vacuum-deposited, for example, a sublimable organic material that may be vacuum-deposited by sublimation. The sublimable organic materials may be an organic material that loses weight with increasing temperature and lose weight by at least about 50% of their initial weight without substantial decomposition or polymerization, which may be confirmed by thermogravimetric analysis (TGA).

For example, the first organic material and the second organic material may be an organic material that may be vacuum-deposited. For this purpose, when the first organic material and the second organic material may be subjected to thermogravimetric analysis at a pressure (e.g., under an ambient pressure) of, for example, about 10 Pa or less (e.g., about 0.01 PA to about 10 Pa), for example, a temperature (hereinafter referred to as "sublimation temperature") at which weight reduction of 10% relative to the initial weight of a given organic material occurs in the given organic material may be within a particular (or, alternatively, predetermined) range under a particular ambient pressure.

For example, a difference between the respective sublimation temperatures of the first organic material and the second organic material may be less than or equal to about 150° C., within the above range, for example less than or equal to about 130° C., less than or equal to about 120° C., less than or equal to about 110° C., less than or equal to about 100° C., less than or equal to about 90° C., less than or equal to about 80° C., less than or equal to about 70° C., less than or equal to about 60° C., less than or equal to about 50° C., less than or equal to about 40° C., less than or equal to about 30° C., less than or equal to about 20° C., less than or equal to about 15° C. or less than or equal to about 10° C., within the above range, about 0° C. to about 150° C., about 0° C. to about 130° C., about 0° C. to about 120° C., about 0° C. to about 110° C., about 0° C. to about 100° C., about 0° C. to about 90° C., about 0° C. to about 80° C., about 0° C. to about 70° C., about 0° C. to about 60° C., about 0° C. to about 50° C., about 0° C. to about 40° C., about 0° C. to about 30° C., about 0° C. to about 20° C., about 0° C. to about 15° C., about 0° C. to about 10° C., about 2° C. to about 150° C., about 2° C. to about 130° C., about 2° C. to about 120° C., about 2° C. to about 110° C., about 2° C. to about 100° C., about 2° C. to about 90° C., about 2° C. to about 80° C., about 2° C. to about 70° C., about 2° C. to about 60° C., about 2° C. to about 50° C., about 2° C. to about 40° C., about 2° C. to about 30° C., about 2° C. to about 20° C., about 2° C. to about 15° C., or about 2° C. to about 10° C.

For example, the respective sublimation temperatures of the first organic material and the second organic material may be less than or equal to about 390° C., within the above range, less than or equal to about 370° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., or less than or equal to about 250° C., about 100° C. to about 390° C., about 100° C. to about 370° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 390° C., about 150° C. to about 370° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C., respectively.

The light absorbing layer 330 may further include a third organic material different from the second organic material. For example, when the second organic material is an n-type semiconductor, the third organic material may be a p-type semiconductor and may form a pn junction with the second organic material. The third organic material may also be, for example, a low molecular weight organic material and may be, for example, a depositable organic material.

For example, the first organic material, the second organic material, and the third organic material may each be an organic material that may be vacuum-deposited, for example, a sublimable organic material that may be vacuum-deposited by sublimation.

For example, the first organic material, the second organic material, and the third organic material may be organic materials that may be vacuum-deposited in the same chamber. For example, the second organic material and the third organic material may be co-deposited or sequentially deposited. Accordingly, the difference between the respective sublimation temperatures of any two materials of the first organic material, the second organic material, or the third organic material may be less than or equal to about 150° C., within the above range, for example less than or equal to about 130° C., less than or equal to about 120° C., less than or equal to about 110° C., less than or equal to about 100° C., less than or equal to about 90° C., less than or equal to about 80° C., less than or equal to about 70° C., less than or equal to about 60° C., less than or equal to about 50° C., less than or equal to about 40° C., less than or equal to about 30° C., less than or equal to about 20° C., less than or equal to about 15° C., or less than or equal to about 10° C., within the above range, about 0° C. to about 150° C., about 0° C. to about 130° C., about 0° C. to about 120° C., about 0° C. to about 110° C., about 0° C. to about 100° C., about 0° C. to about 90° C., about 0° C. to about 80° C., about 0° C. to about 70° C., about 0° C. to about 60° C., about 0° C. to about 50° C., about 0° C. to about 40° C., about 0° C. to about 30° C., about 0° C. to about 20° C., about 0° C. to about 15° C., about 0° C. to about 10° C., about 2° C. to about 150° C., about 2° C. to about 130° C., about 2° C. to about 120° C., about 2° C. to about 110° C., about 2° C. to about 100° C., about 2° C. to about 90° C., about 2° C. to about 80° C., about 2° C. to about 70° C., about 2° C. to about 60° C., about 2° C. to about 50° C., about 2° C. to about 40° C., about 2° C. to about 30° C., about 2° C. to about 20° C., about 2° C. to about 15° C., or about 2° C. to about 10° C.

For example, the respective sublimation temperatures of the first organic material, the second organic material, and the third organic material may be less than or equal to about 390° C., within the above range, less than or equal to about 370° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., or less than or equal to about 250° C., about 100° C. to about 390° C., about 100° C. to about 370° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 390° C., about 150° C. to about 370° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C. or about 150° C. to about 250° C., respectively.

For example, the first organic material may be a known material that may be included in the light emitting layers 212, 222, and 232, for example, perylene; rubrene; 4-(di-cyanomethylene)-2-methyl-6-[p-(dimethylamino) styryl]-4H-pyran; coumarin or a derivative thereof; carbazole or a derivative thereof; TPBi (2,2',2"-(1,3,5-benzenetriyl)-tris(1-phenyl-1-H-benzimidazole); TBADN (2-t-butyl-9,10-di(naphth-2)-yl) anthracene); AND (9,10-di(naphthalene-2-yl) anthracene); CBP (4,4'-bis(N-carbazolyl)-1,1'-biphenyl); TCTA (4,4',4"-tris(carbazol-9-yl)-triphenylamine); TPBi (1,3,5-tris(N-phenylbenzimidazole-2-yl)benzene); TBADN (3-tert-butyl-9,10-di(naphth-2-yl) anthracene); DSA (distyrylarylene); CDBP (4,4"-dimethyl-biphenyl); MADN (2-methyl-9,10-bis(naphthalen-2-yl) anthracene); TCP (1,3,5-tris(carbazol-9-yl)benzene); Alq3 (tris(8-hydroxyquinolino) lithium); an organometallic compound containing Pt, Os, Ti, Zr, Hf, Eu, Tb, Tm, Rh, Ru, Re, Be, Mg, Al, Ca, Mn, Co, Cu, Zn, Ga, Ge, Pd, Ag, and/or Au, a derivative thereof, or any combination thereof, but is not limited thereto. The known material that may be included in the light emitting layers 212, 222, and 232 may have a sublimation temperature of less than or equal to about 390° C. (e.g., about 0° C. to about 390° C.) under an ambient pressure of, for example, about 0.01 Pa to about 10 Pa, which may satisfy the aforementioned sublimation temperature range.

For example, the second organic material may be a transparent n-type semiconductor having an energy bandgap of greater than or equal to about 2.5 eV as described above, and the third organic material may be a p-type semiconductor configured to absorb light of at least a portion of a visible light wavelength spectrum (e.g., light of any one of a red wavelength spectrum, a green wavelength spectrum, or a blue wavelength spectrum).

For example, the second organic material may be a transparent n-type semiconductor having an energy bandgap of greater than or equal to about 2.5 eV as described above, and the third organic material may be a p-type semiconductor configured to selectively absorb light of any one or two of a red wavelength spectrum, a green wavelength spectrum, or a blue wavelength spectrum. Additionally, the second organic material may have an energy level capable of forming effective electrical matching with the first common auxiliary layer 340 as an n-type semiconductor of the light absorbing layer 330. For example, the difference between the LUMO energy level of the first common auxiliary layer 340 and the LUMO energy level of the second organic material may be less than or equal to about 1.2 eV, within the above range, less than or equal to about 1.1 eV, less than or equal to about 1.0 eV, less than or equal to about 0.8 eV, less than or equal to about 0.7 eV, or less than or equal to about 0.5 eV, about 0 eV to about 1.2 eV, about 0 eV to about 1.1 eV, about 0 eV to about 1.0 eV, about 0 eV to about 0.8 eV, about 0 eV to about 0.7 eV, about 0 eV to about 0.5 eV, about 0.01 eV to about 1.2 eV, about 0.01 eV to about 1.1 eV, about 0.01 eV to about 1.0 eV, about 0.01 eV to about 0.8 eV, about 0.01 eV to about 0.7 eV, or about 0.01 eV to about 0.5 eV. Accordingly, charge carriers (e.g., electrons) generated in the light absorbing layer 330 may pass through the first common auxiliary layer 340 and may be effectively moved and/or extracted to the common electrode 320.

The second organic material may be selected from compounds satisfying the aforementioned deposition characteristics and electrical characteristics. For example, the second organic material may include a planar core having an imide group or an anhydride group, and may be, for example, represented by Chemical Formula 1.

[Chemical Formula 1]

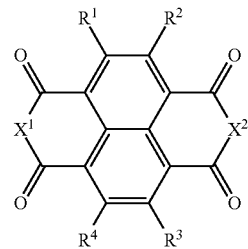

In Chemical Formula 1,

X$^1$ and X$^2$ may each independently be O or NR$^a$, and

R$^1$ to R$^4$, and R$^a$ may each independently be hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

For example, the second organic material represented by Chemical Formula 1 may be represented by Chemical Formula 1A or 1B.

[Chemical Formula 1A]

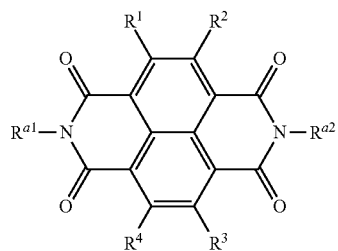

[Chemical Formula 1B]

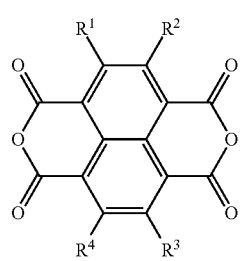

In Chemical Formulas 1A and 1B,

R$^1$ to R$^4$, R$^{a1}$, and R$^{a2}$ may each independently be hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

For example, at least one of R$^{a1}$ or R$^{a2}$ may include an electron withdrawing group, and for example, R$^{a1}$ and R$^{a2}$ may each include an electron withdrawing group.

For example, at least one of R$^{a1}$ or R$^{a2}$ may be a halogen; a cyano group; a halogen-substituted C1 to C30 alkyl group; a halogen-substituted C6 to C30 aryl group; a halogen-substituted C3 to C30 heterocyclic group; a cyano-substituted C1 to C30 alkyl group; a cyano-substituted C6 to C30 aryl group; a cyano-substituted C3 to C30 heterocyclic group; a substituted or unsubstituted pyridinyl group; a substituted or unsubstituted pyrimidinyl group; a substituted or unsubstituted triazinyl group; a substituted or unsubstituted pyrazinyl group; a substituted or unsubstituted quinolinyl group; a substituted or unsubstituted isoquinolinyl group; a substituted or unsubstituted quinazolinyl group; a C1 to C30 alkyl group substituted with a substituted or unsubstituted pyridinyl group; a C6 to C30 aryl group substituted with a substituted or unsubstituted pyridinyl group; a C1 to C30 alkyl group substituted with a substituted or unsubstituted pyrimidinyl group; a C6 to C30 aryl group substituted with a substituted or unsubstituted pyrimidinyl group; a C1 to C30 alkyl group substituted with a substituted or unsubstituted triazinyl group; a C6 to C30 aryl group substituted with a substituted or unsubstituted triazinyl group; a C1 to C30 alkyl group substituted with a substituted or unsubstituted pyrazinyl group; a C6 to C30 aryl group substituted with a substituted or unsubstituted pyrazinyl group; a C1 to C30 alkyl group substituted with a substituted or unsubstituted quinolinyl group; a C6 to C30 aryl group substituted with a substituted or unsubstituted quinolinyl group; a C1 to C30 alkyl group substituted with a substituted or unsubstituted isoquinolinyl group; a C6 to C30 aryl group substituted with a substituted or unsubstituted isoquinolinyl group; a C1 to C30 alkyl group substituted with a substituted or unsubstituted quinazolinyl group; a C6 to C30 aryl group substituted with a substituted or unsubstituted quinazolinyl group; or any combination thereof.

For example, R$^{a1}$ and R$^{a2}$ may each include a halogen; a cyano group; a halogen-substituted C1 to C30 alkyl group; a halogen-substituted C6 to C30 aryl group; a halogen-substituted C3 to C30 heterocyclic group; a cyano-substituted C1 to C30 alkyl group; a cyano-substituted C6 to C30 aryl group; a cyano-substituted C3 to C30 heterocyclic group; a substituted or unsubstituted pyridinyl group; a substituted or unsubstituted pyrimidinyl group; a substituted or unsubstituted triazinyl group; a substituted or unsubstituted pyrazinyl group; a substituted or unsubstituted quinolinyl group; a substituted or unsubstituted isoquinolinyl group; a substituted or unsubstituted quinazolinyl group; a C1 to C30 alkyl group substituted with a substituted or unsubstituted pyridinyl group; a C6 to C30 aryl group substituted with a substituted or unsubstituted pyridinyl group; a C1 to C30 alkyl group substituted with a substituted or unsubstituted pyrimidinyl group; a C6 to C30 aryl group substituted with a substituted or unsubstituted pyrimidinyl group; a C1 to C30 alkyl group substituted with a substituted or unsubstituted triazinyl group; a C6 to C30 aryl group substituted with a substituted or unsubstituted triazinyl group; a C1 to C30 alkyl group substituted with a substituted or unsubstituted pyrazinyl group; a C6 to C30 aryl group substituted with a substituted or unsubstituted pyrazinyl group; a C1 to C30 alkyl group substituted with a substituted or unsubstituted quinolinyl group; a C6 to C30 aryl group substituted with a substituted or unsubstituted quinolinyl group; a C1 to C30 alkyl group substituted with a substituted or unsubstituted isoquinolinyl group; a C6 to C30 aryl group substituted with a substituted or unsubstituted isoquinolinyl group; a C1 to C30 alkyl group substituted with a substituted or unsubstituted quinazolinyl group; a C6 to C30 aryl group substituted with a substituted or unsubstituted quinazolinyl group; or any combination thereof.

For example, $R^{a1}$ and $R^{a2}$ may be the same as or different from each other, for example, may be the same.

The second organic material may be, for example, selected from compounds listed in Group 1 below, but is not limited thereto.

[Group 1]

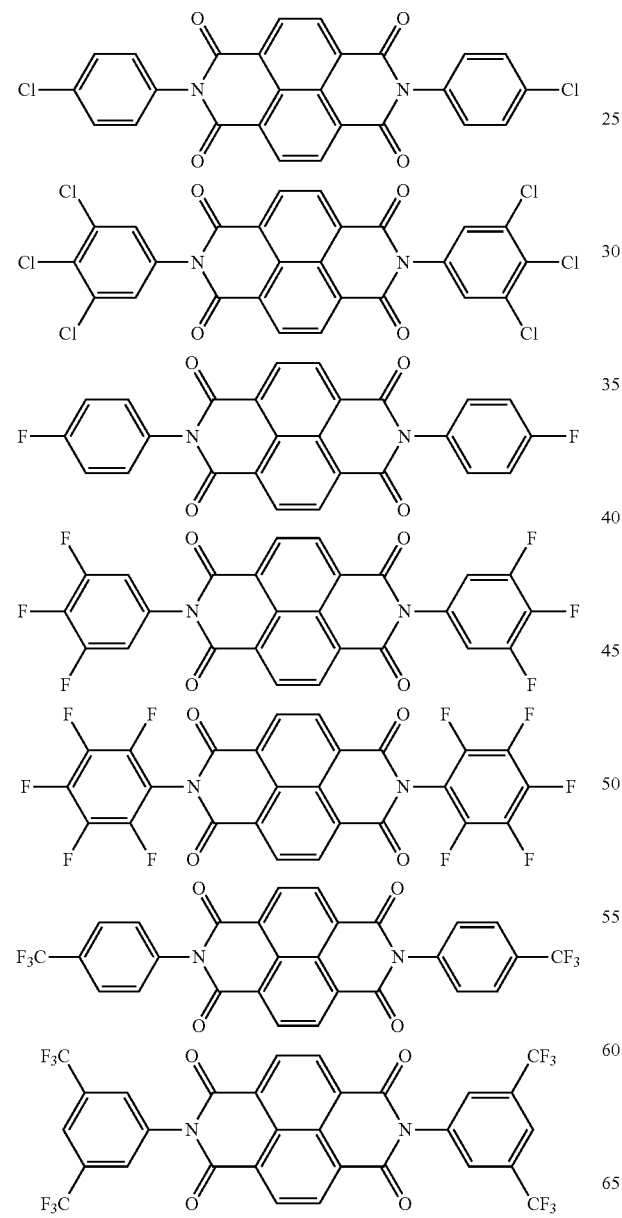

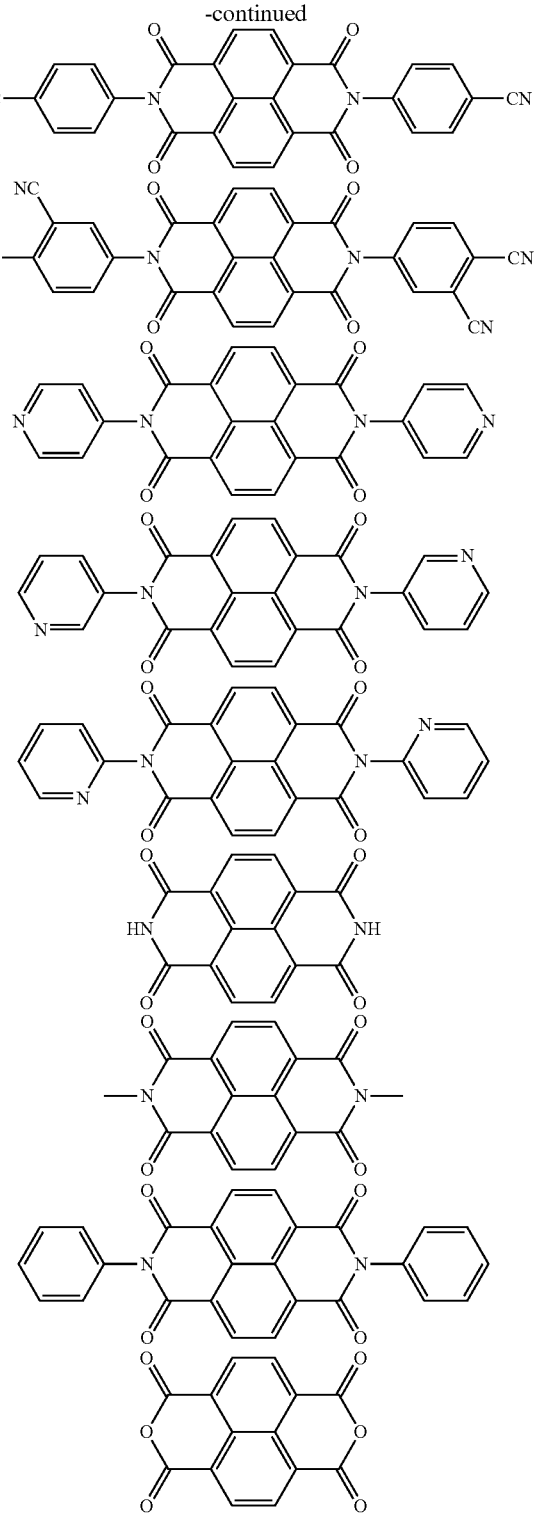

The third organic material may be selected from a compound configured to absorb at least a portion of the visible light wavelength spectrum and satisfying the aforementioned deposition characteristics.

For example, the third organic material may be selected from a compound configured to selectively absorb light of a green wavelength spectrum and satisfying the aforementioned deposition characteristics. Additionally, the third organic material may form a pn junction with the aforementioned second organic material. For example, the HOMO energy level of the third organic material may be, for example, about 5.0 eV to about 6.0 eV, about 5.1 eV to about 5.9 eV, about 5.2 eV to about 5.8 eV, or about 5.3 eV to about 5.8 eV, but is not limited thereto.

The third organic material may be, for example, a compound including an electron donating moiety and an electron accepting moiety, and may be represented by, for example, Chemical Formula A.

EDM-LM-EAM  [Chemical Formula A]

In Chemical Formula A,
EDM may be an electron donating moiety,
EAM may be an electron accepting moiety, and
LM may be a pi conjugated linking moiety of the electron donating moiety and the electron accepting moiety.

For example, the third organic material may be represented by Chemical Formula 2.

[Chemical Formula 2]

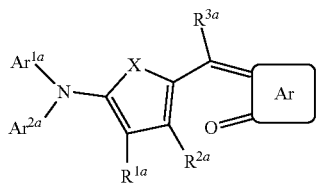

In Chemical Formula 2,
X may be O, S, Se, Te, SO, $SO_2$, $CR^bR^c$, or $SiR^dR^e$,
Ar may be a substituted or unsubstituted C6 to C30 arylene group, a substituted or unsubstituted C3 to C30 heterocyclic group, or a fused ring of two or more thereof,
$Ar^{1a}$ and $Ar^{2a}$ may each independently be a substituted or unsubstituted C6 to C30 aryl(ene) group or a substituted or unsubstituted C3 to C30 heteroaryl(ene) group,
$R^{1a}$ to $R^{3a}$ and $R^b$ to $R^e$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, and
$Ar^{1a}$, $Ar^{2a}$, $R^{1a}$, and $R^{2a}$ are each independently present, or two adjacent ones of $Ar^{1a}$, $Ar^{2a}$, $R^{1a}$, or $R^{2a}$ may be bonded to each other to form a ring. Two adjacent ones of $Ar^{1a}$, $Ar^{2a}$, $R^{1a}$, or $R^{2a}$ may be bonded to each other directly or via a linking group to form a ring. The linking group may be, for example, O, S, Se, Te, SO, $SO_2$, $CR^fR^g$, $SiR^hR^k$, $GeR^jR^k$, $NR^l$, or any combination thereof, wherein $R^f$ to $R^l$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof.

For example, $Ar^{1a}$ and $Ar^{2a}$ may each independently be a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, or a substituted or unsubstituted pyridopyridazinyl group.

For example, $Ar^{1a}$ and $Ar^{2a}$ may be bonded to each other to form a ring.

For example, $Ar^{2a}$ and $R^{1a}$ may be bonded to each other to form a ring.

Specifically, the third organic compound may be represented by Chemical Formula 2A or 2B.

[Chemical Formula 2A]

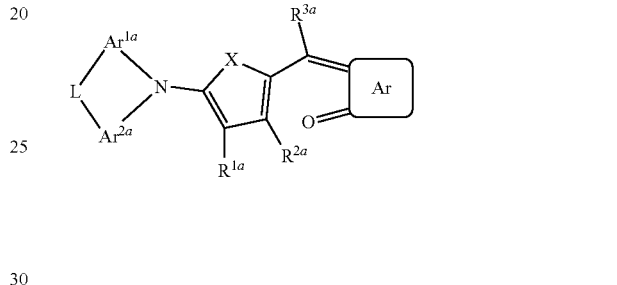

[Chemical Formula 2B]

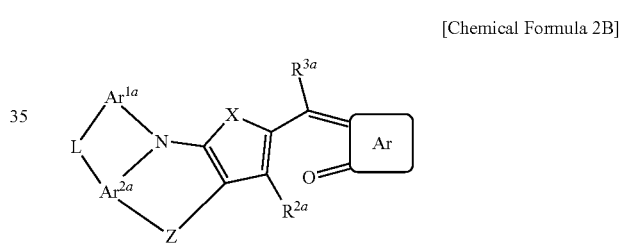

In Chemical Formulas 2A and 2B,
X may be O, S, Se, Te, SO, $SO_2$, $CR^bR^c$, or $SiR^dR^e$,
Ar may be a substituted or unsubstituted C6 to C30 arylene group, a substituted or unsubstituted C3 to C30 heterocyclic group, or a fused ring of two or more thereof,
$Ar^{1a}$ and $Ar^{2a}$ may each independently be a substituted or unsubstituted C6 to C30 arylene group or a substituted or unsubstituted C3 to C30 heteroarylene group,
L and Z may each independently be a single bond, O, S, Se, Te, SO, $SO_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and
$R^{1a}$, $R^{2a}$, $R^{3a}$, and $R^b$ to $R^l$ may each independently be hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof.

For example, the third organic compound may be selected from compounds of Groups 2A, 2B, or 2C, but is not limited thereto.

[Group 2A]
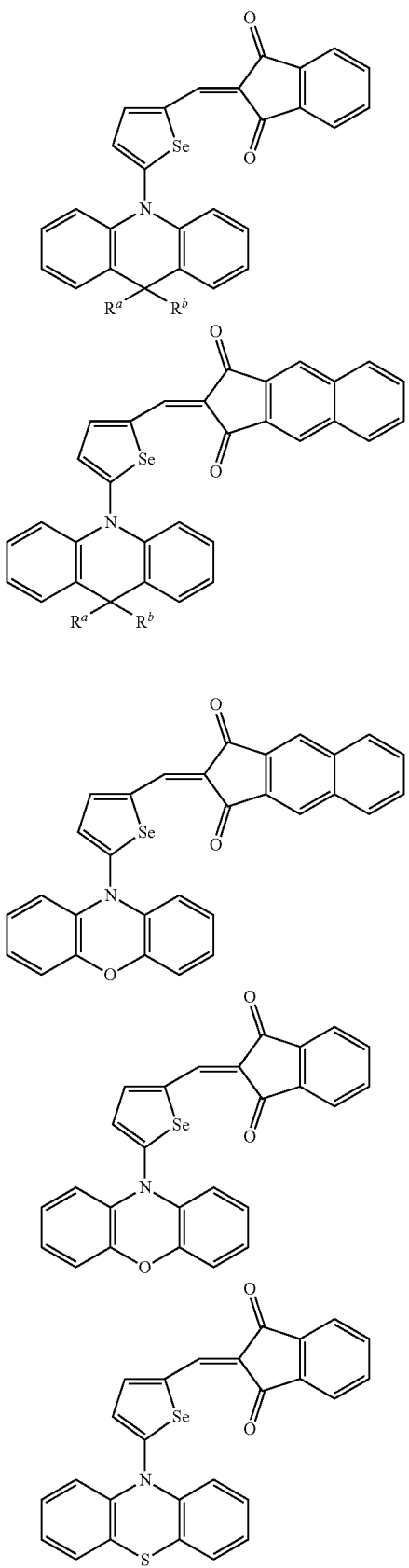
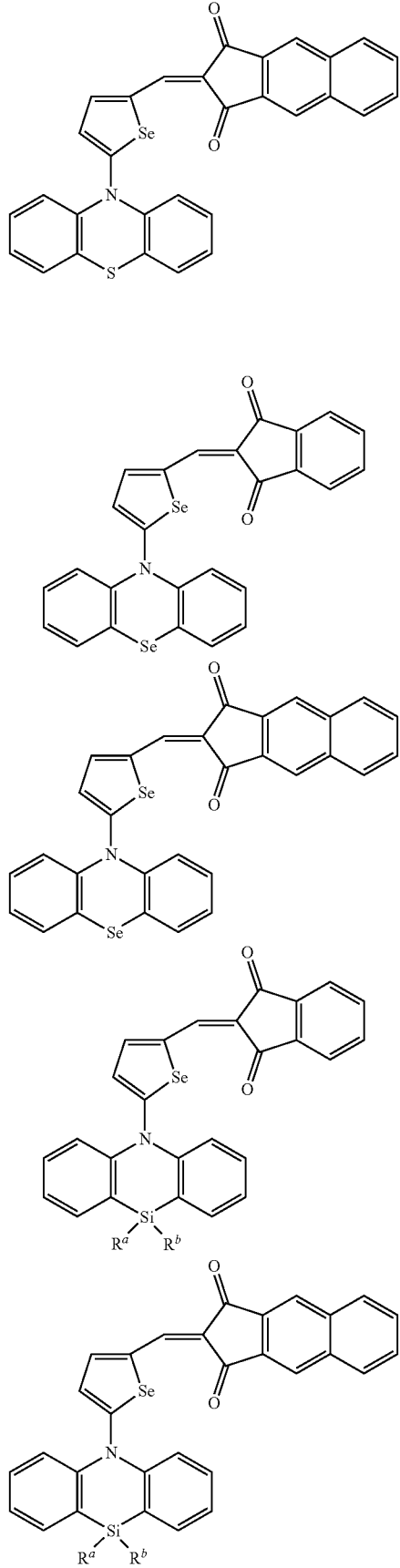

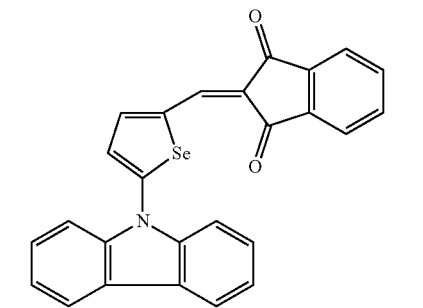
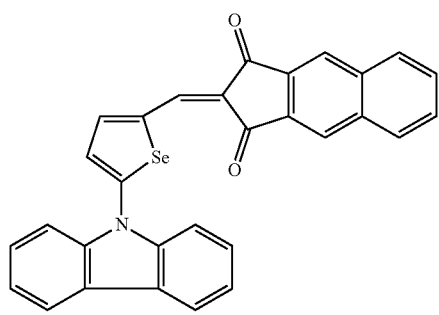
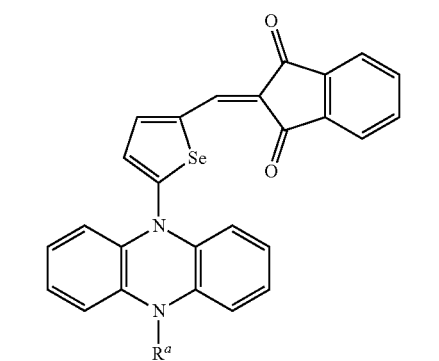
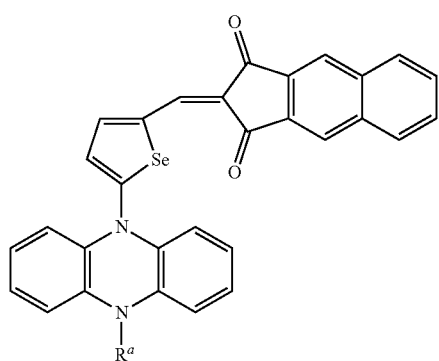
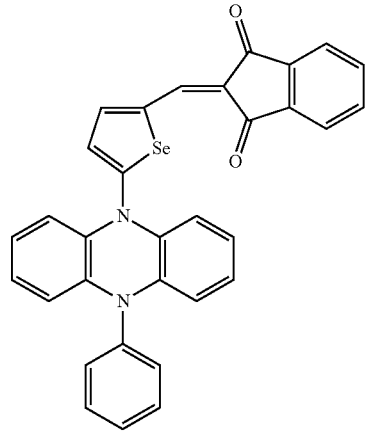
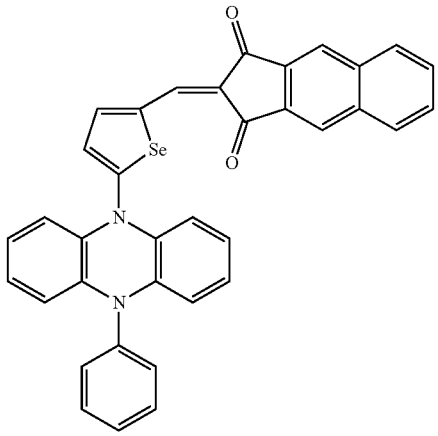
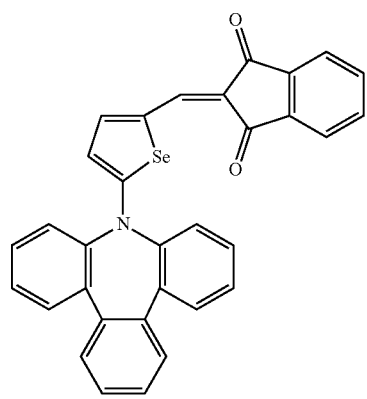
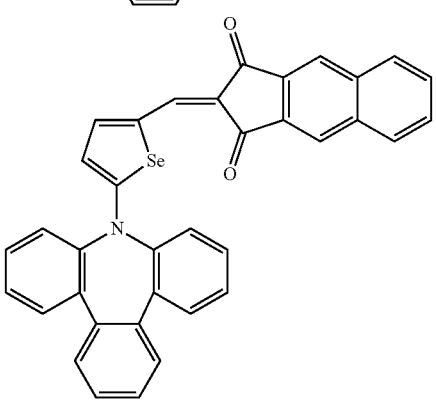

-continued
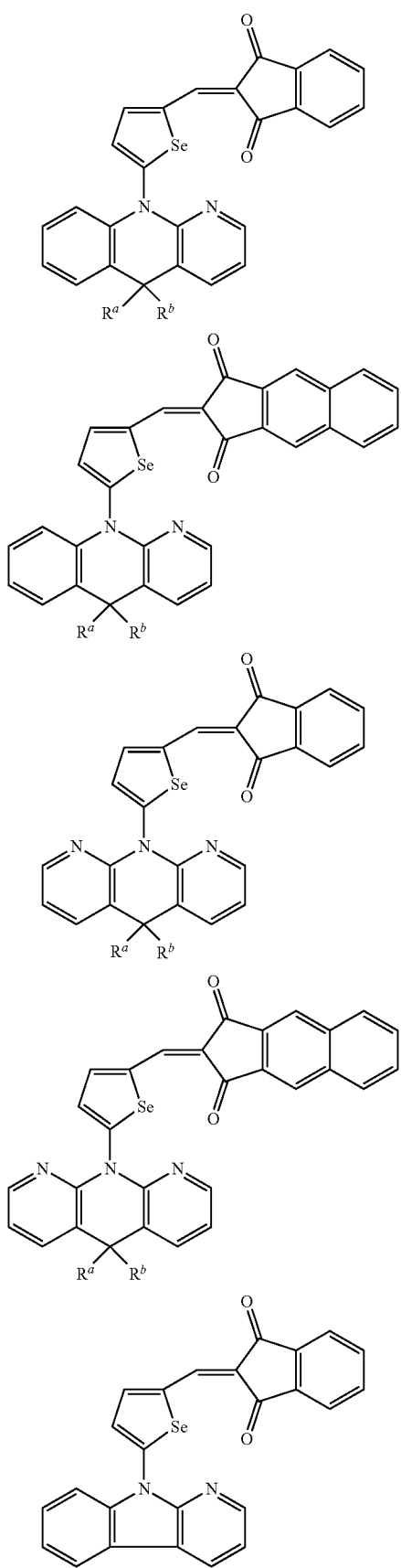
-continued
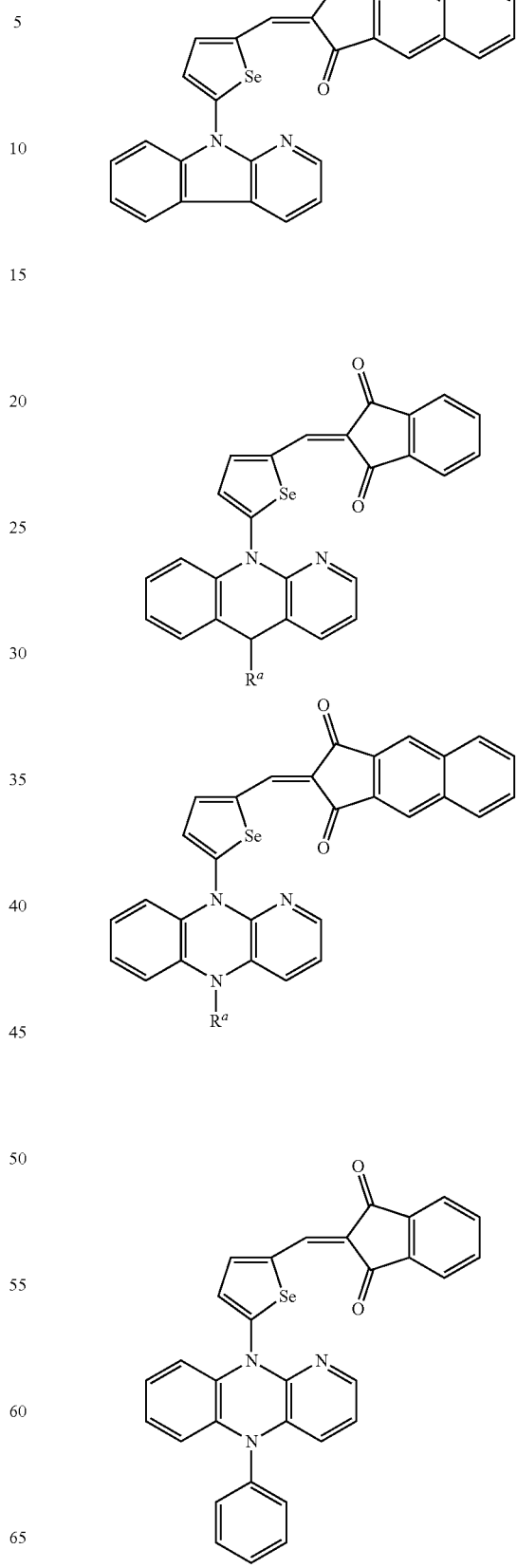

-continued
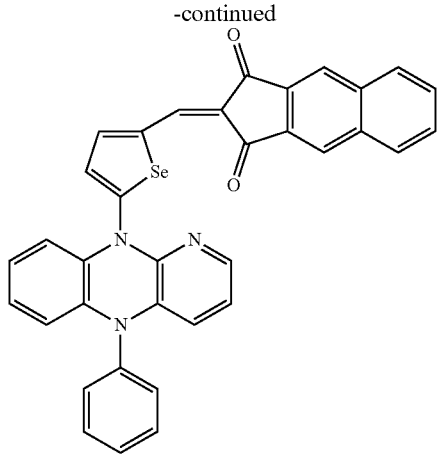
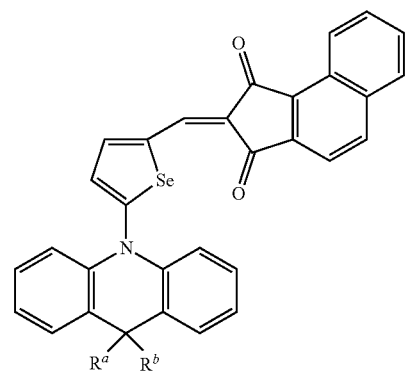
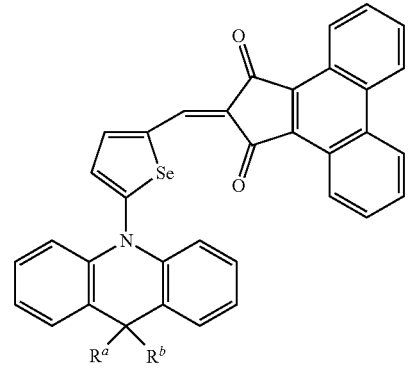
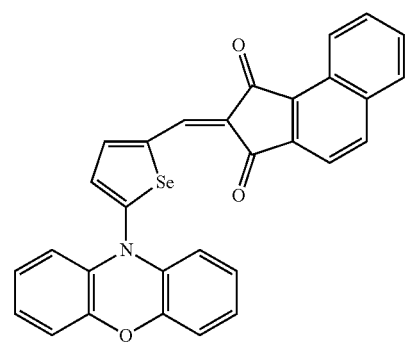
-continued
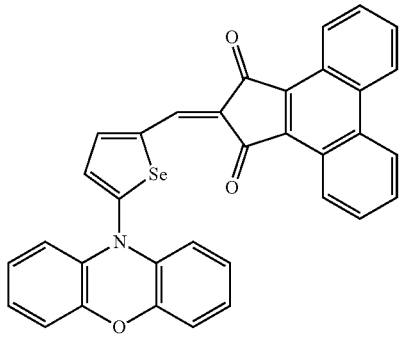
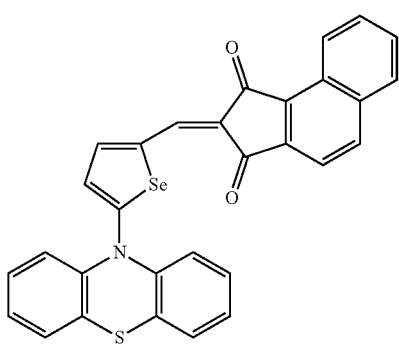
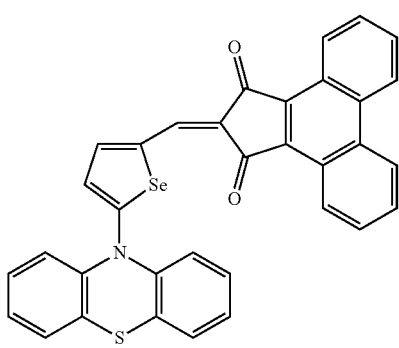
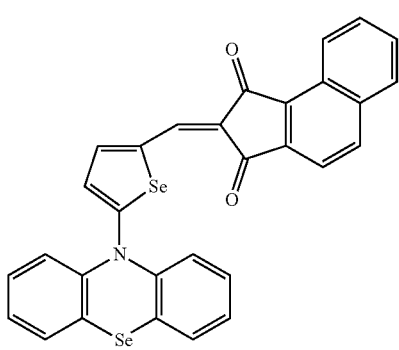
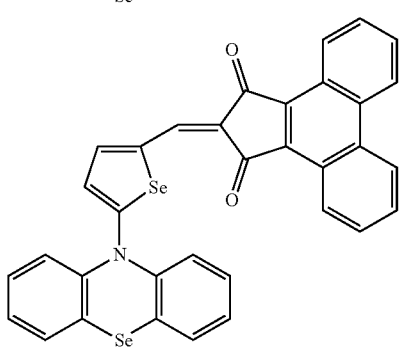

-continued
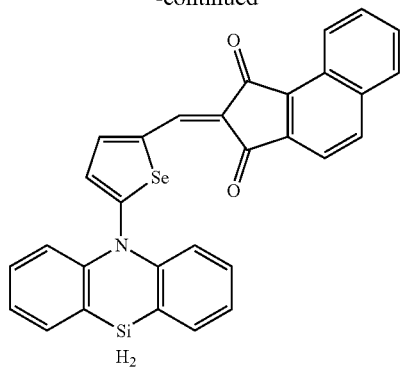
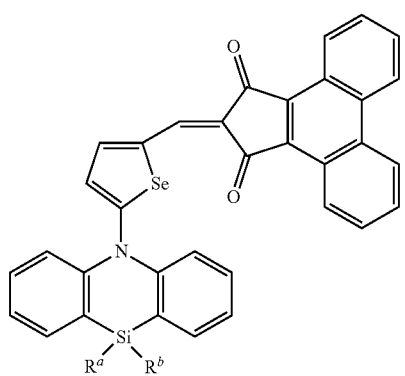
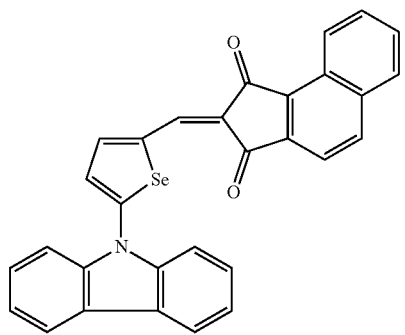
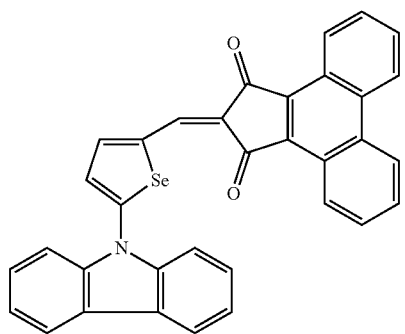
⊚ indicates text missing or illegible when filed
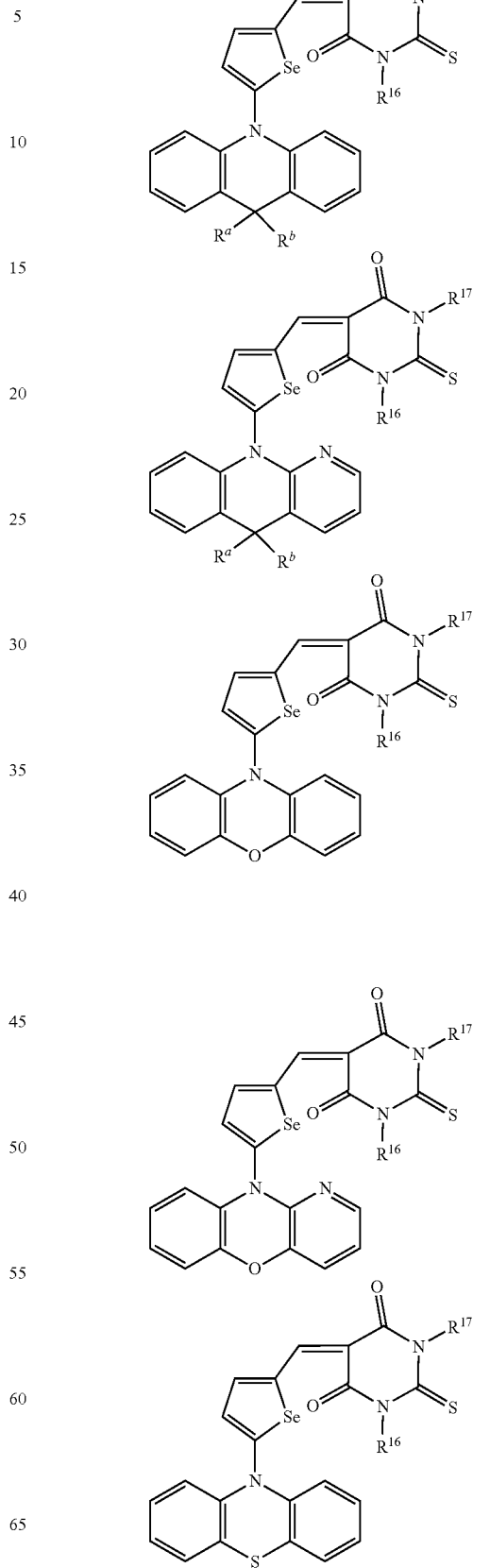

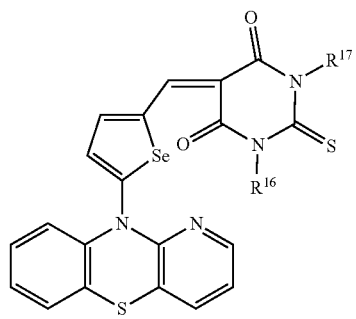
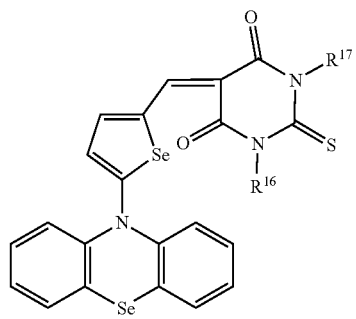
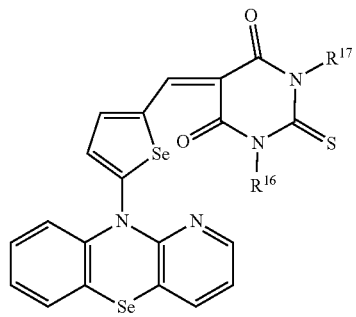
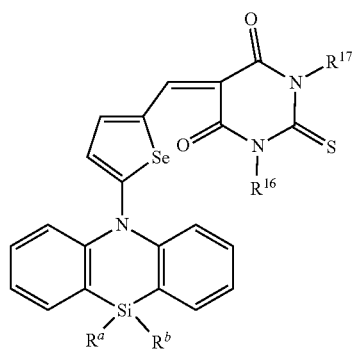
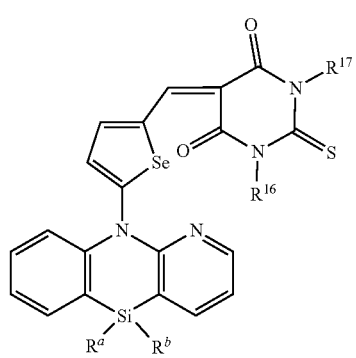
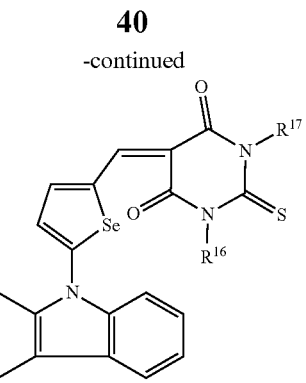
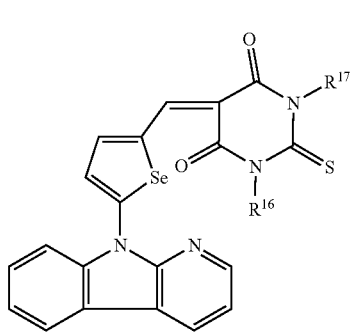
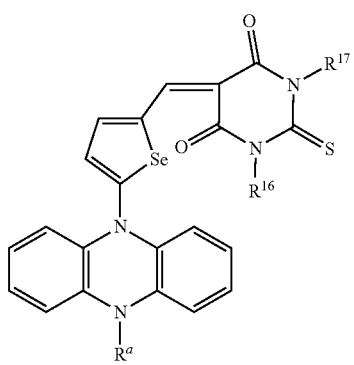
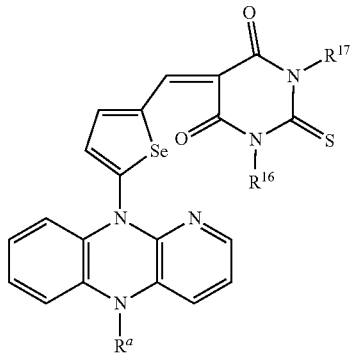

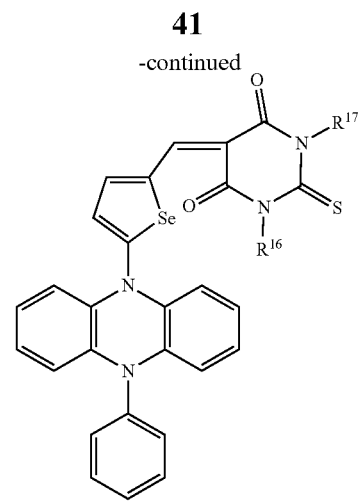
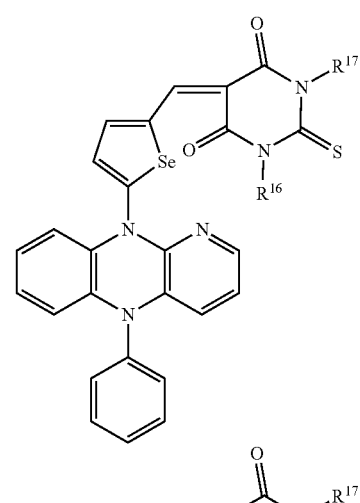
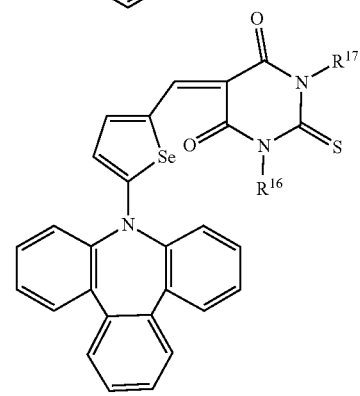
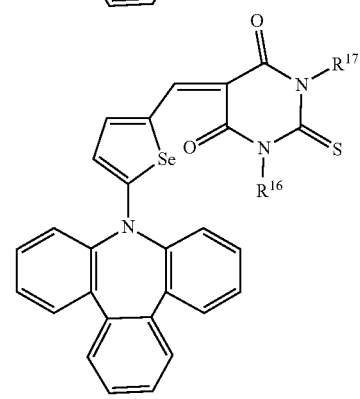
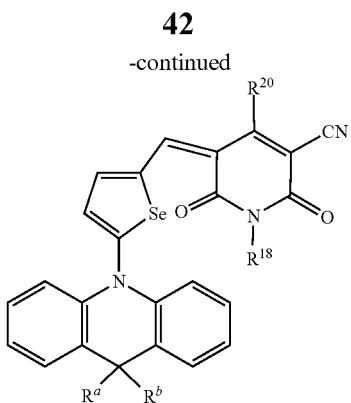
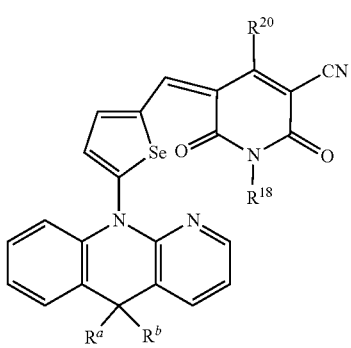
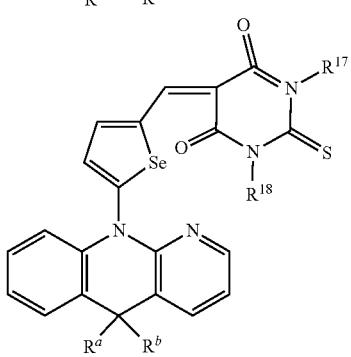
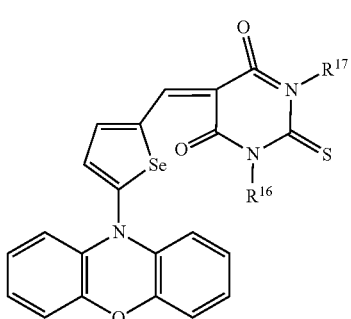
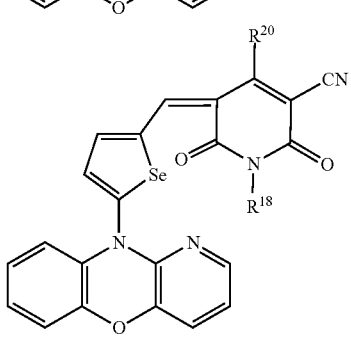

-continued
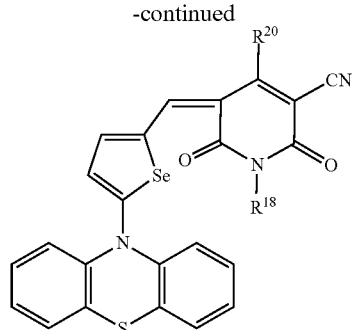
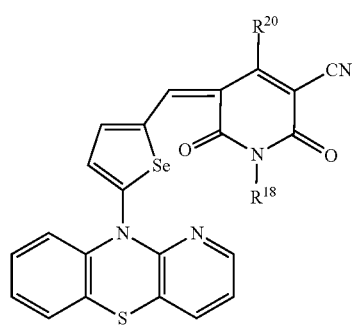
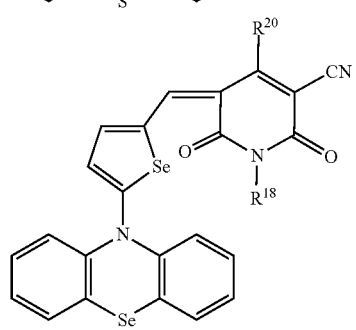
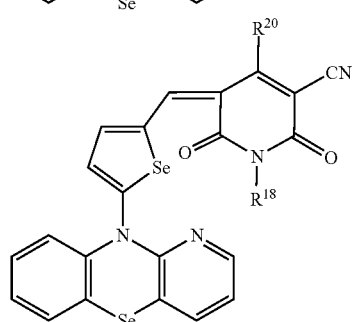
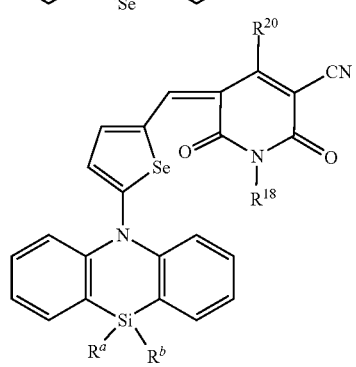
-continued
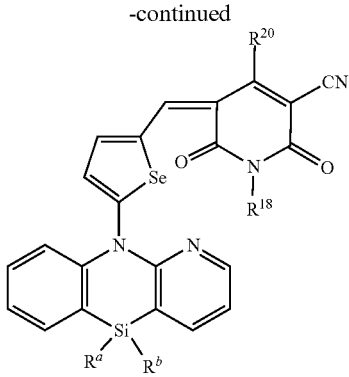
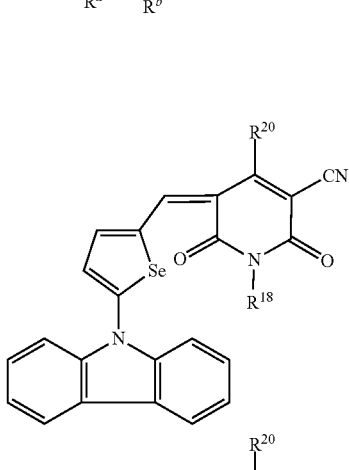
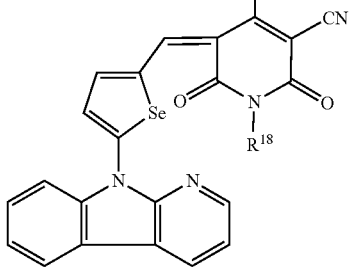
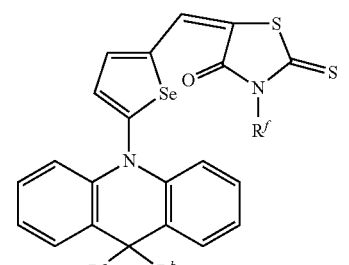
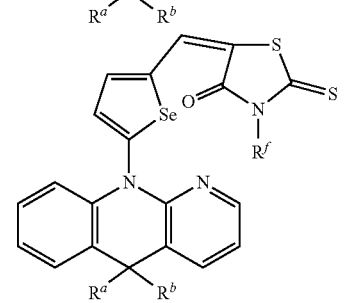

-continued

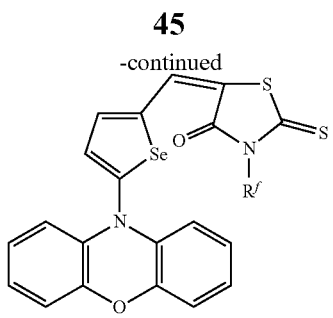
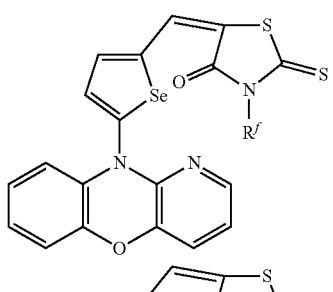
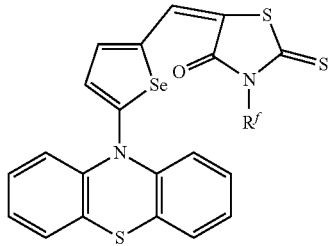
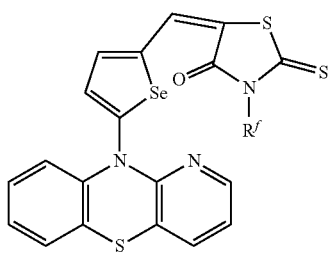
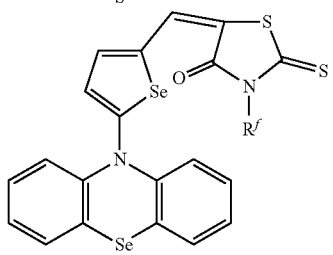
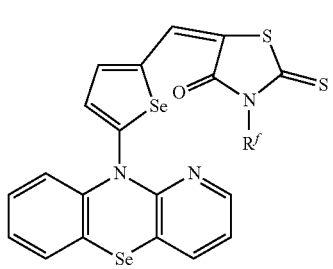

-continued

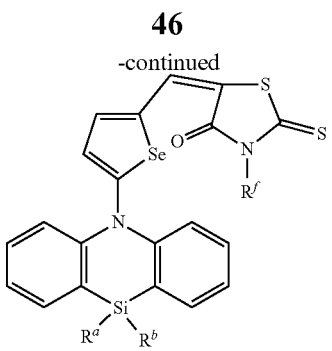
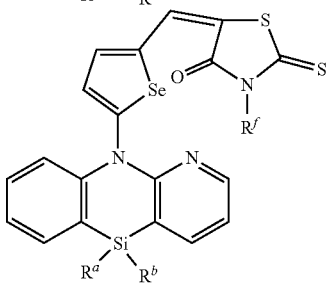
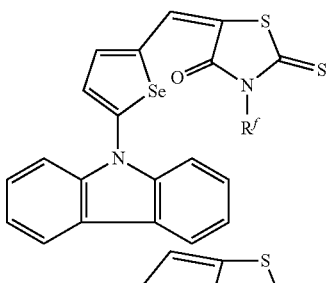
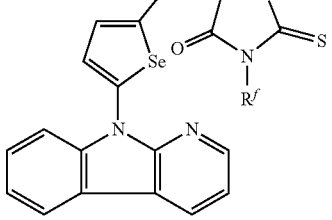

In Group 2A, at least one hydrogen of each aromatic ring or heteroaromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and combinations thereof, and $R^a$, $R^b$, $R^f$, $R^{16}$, $R^{17}$, $R^{18}$, and $R^{20}$ may each independently be hydrogen or a substituted or unsubstituted C1 to C6 alkyl group.

[Group 2B]

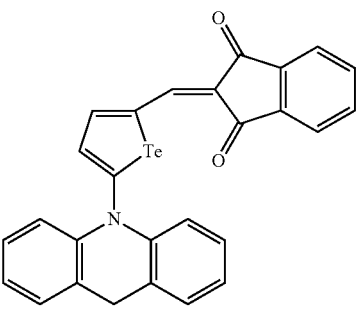

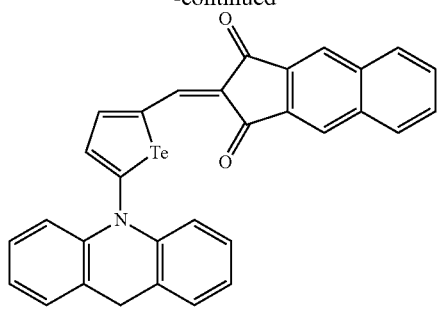
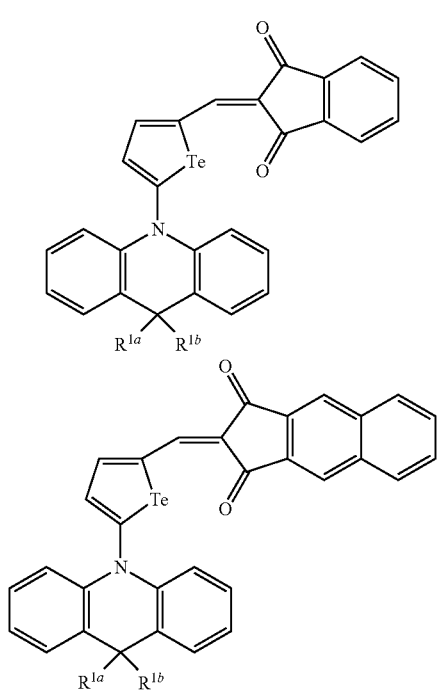
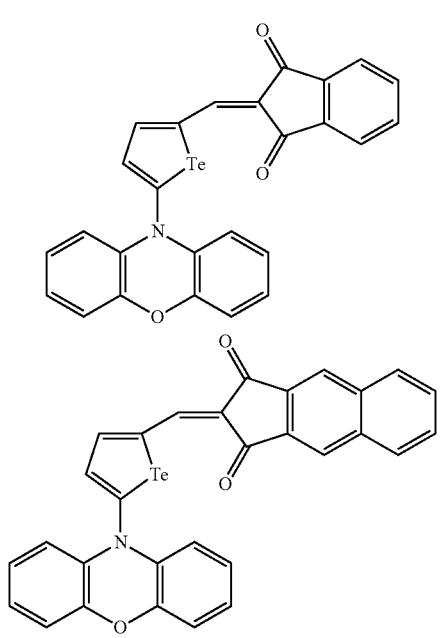
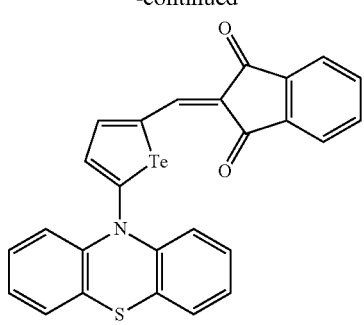
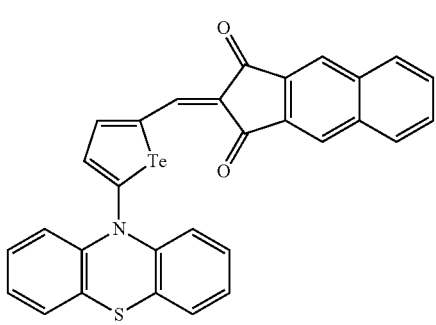
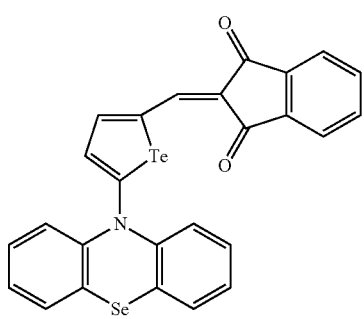
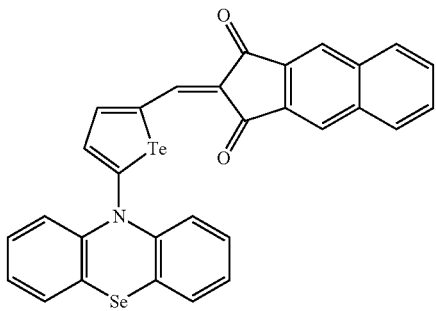
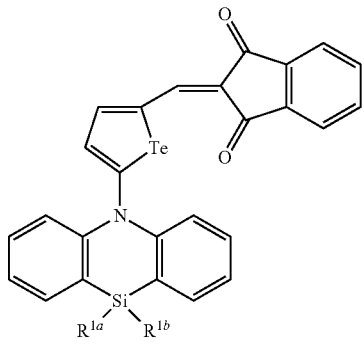

49
-continued
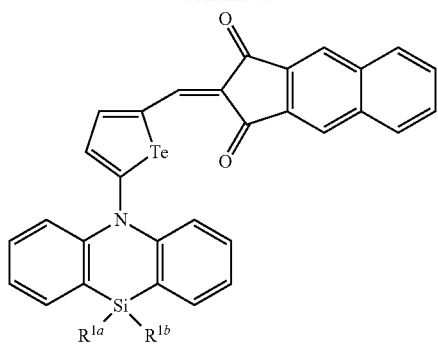
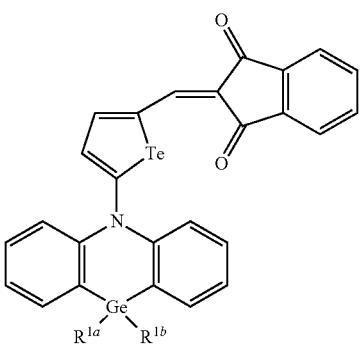
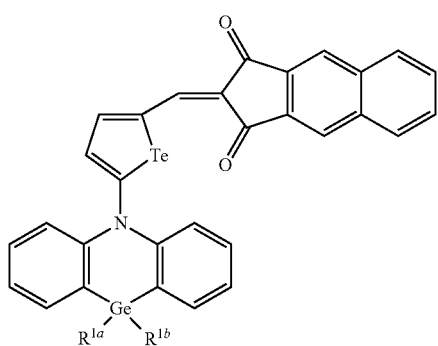
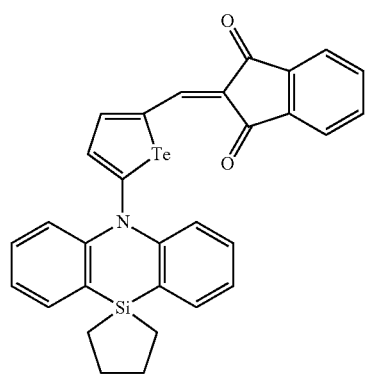
50
-continued
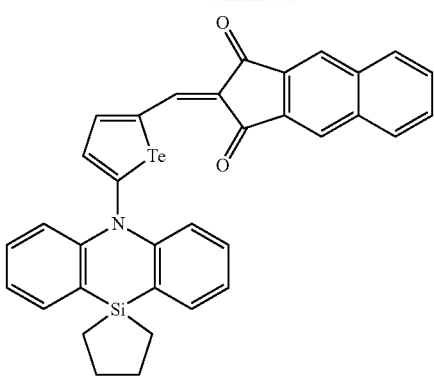
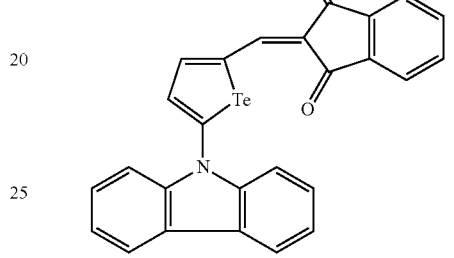
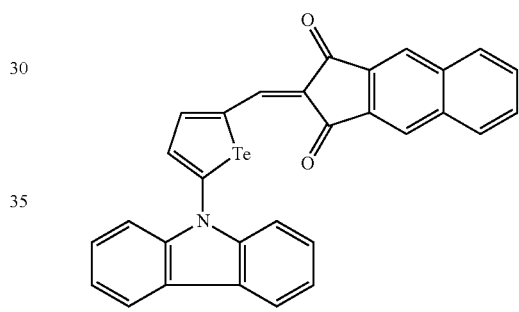
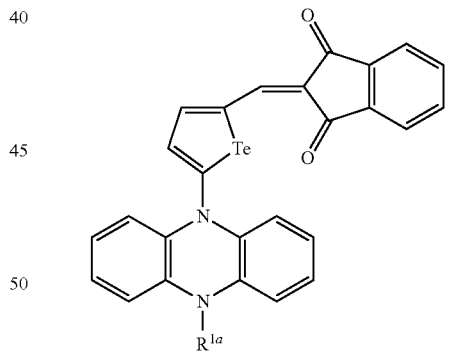
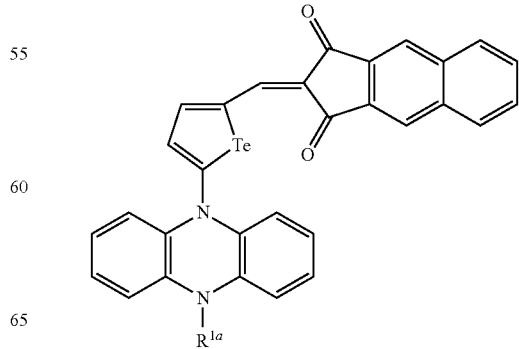

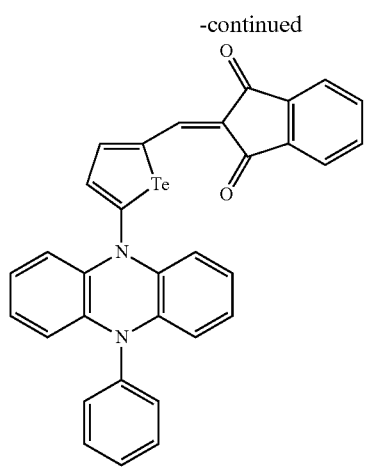
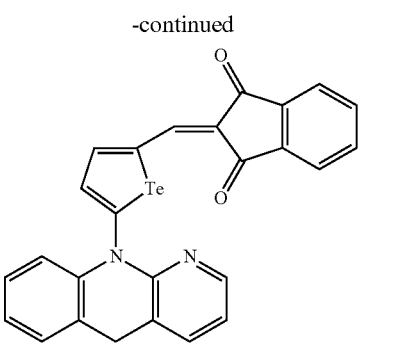
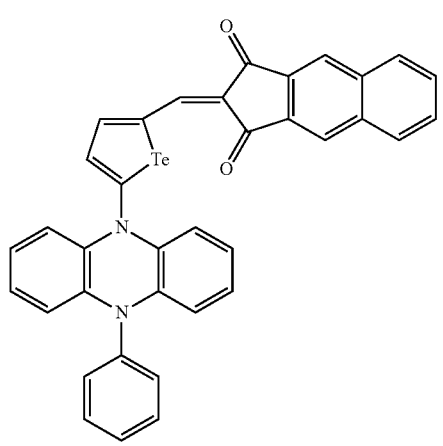
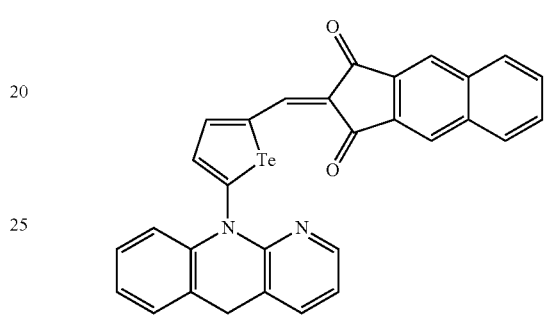
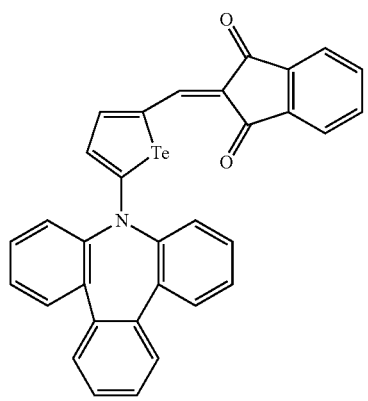
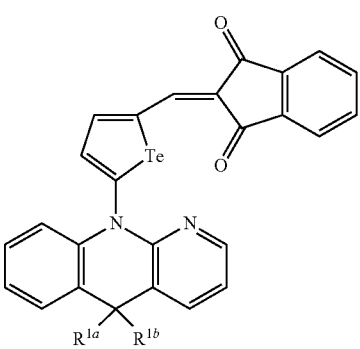
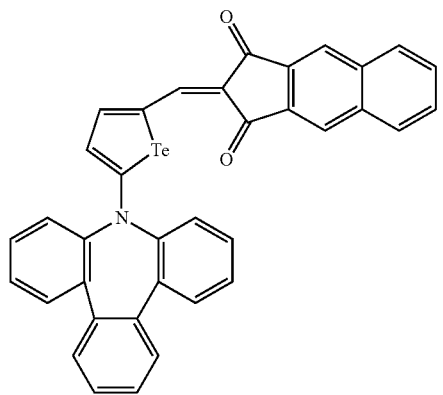
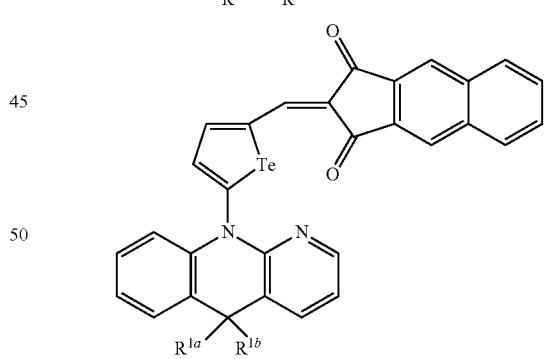
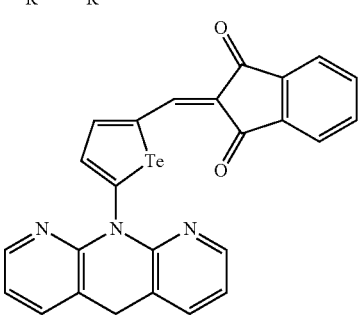

-continued

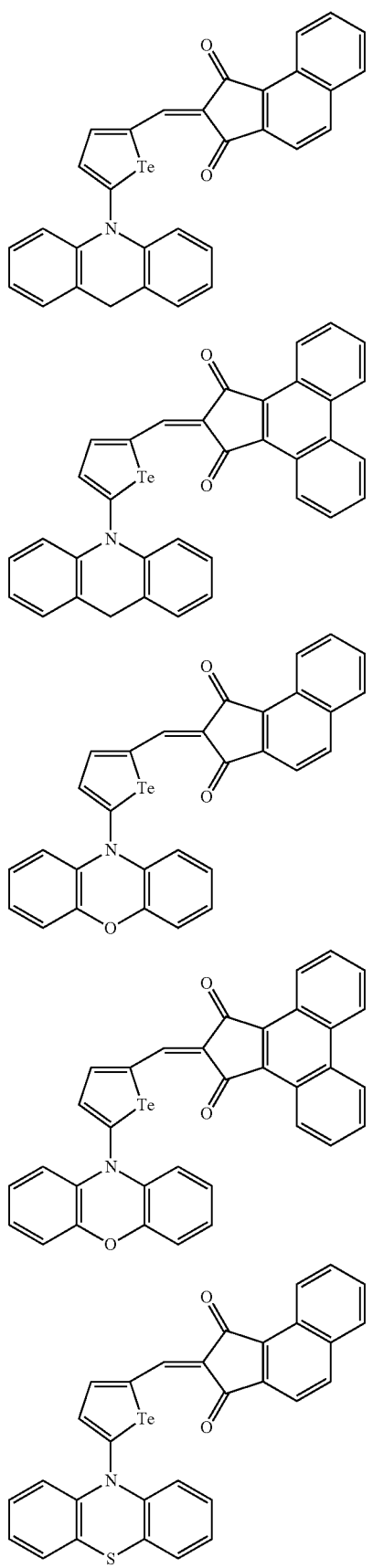
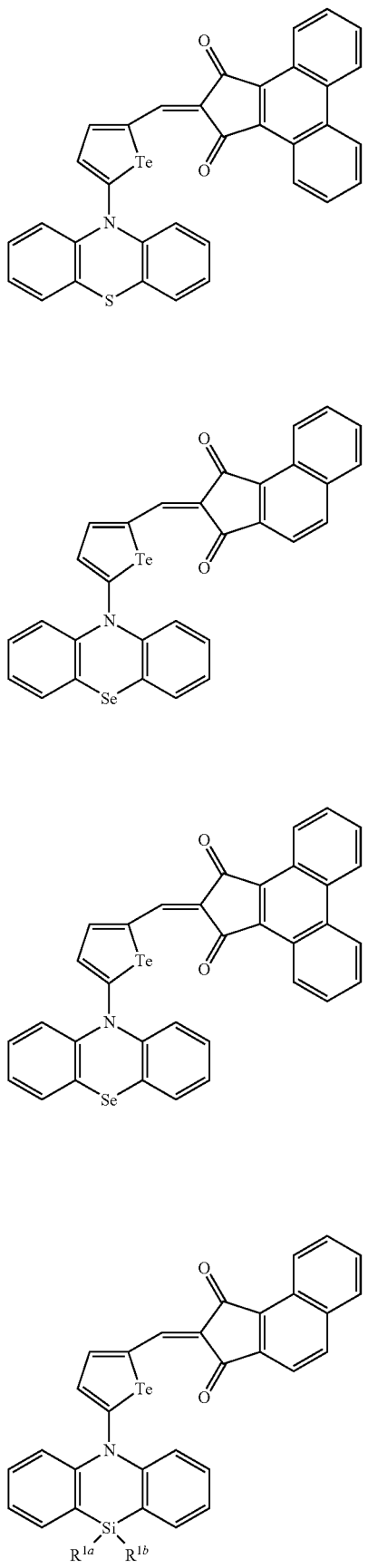

-continued
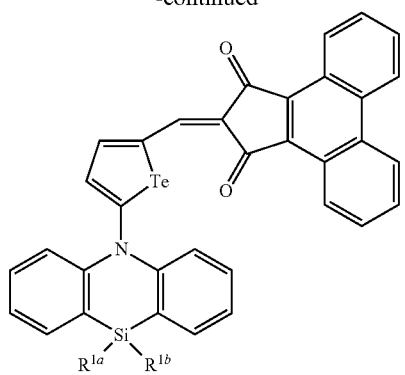
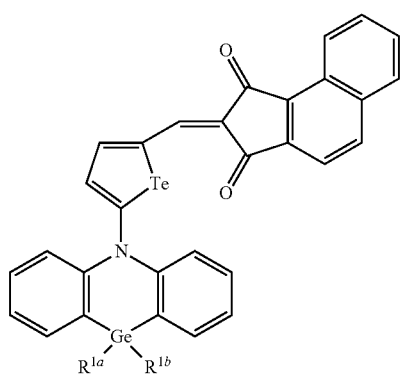
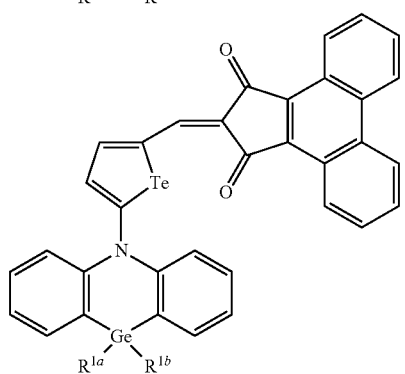
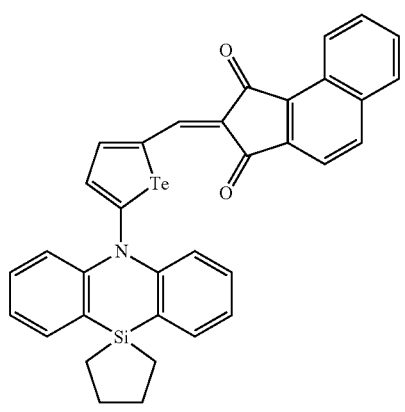
-continued
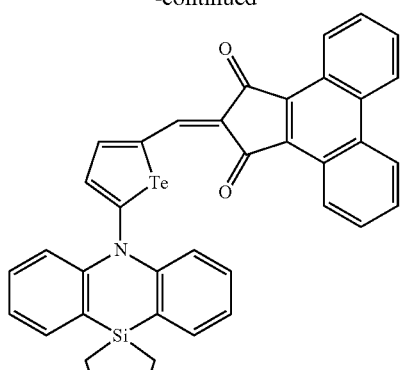
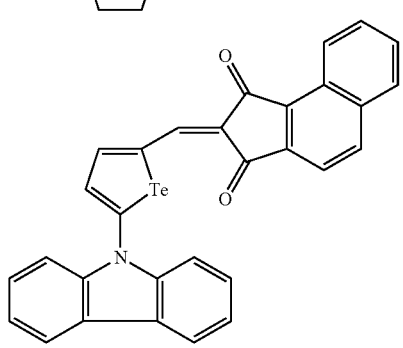
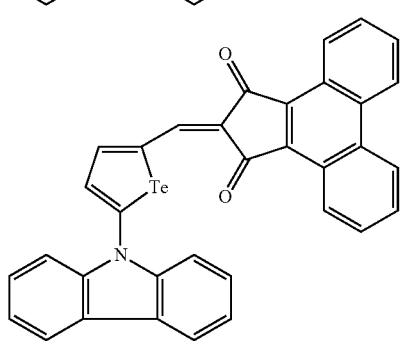
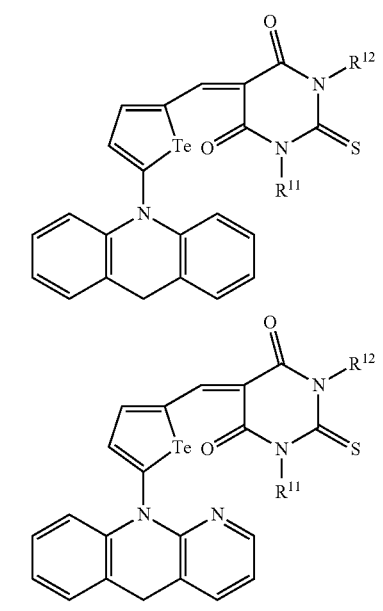

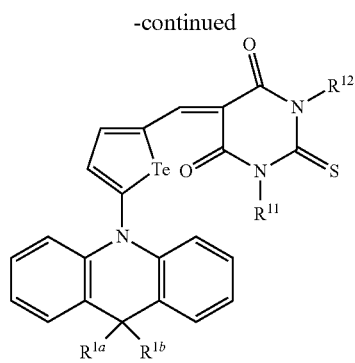
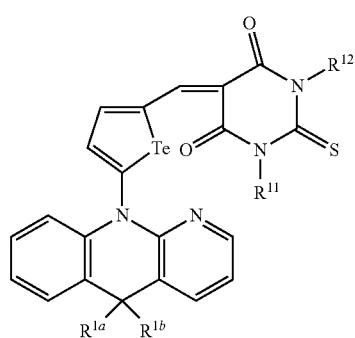
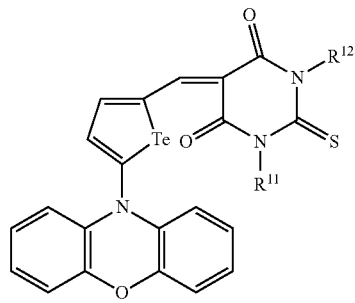
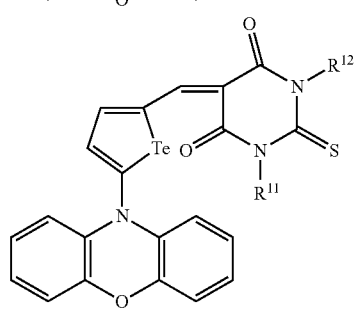
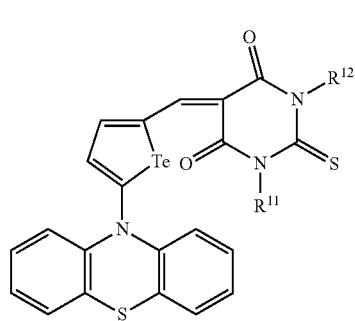
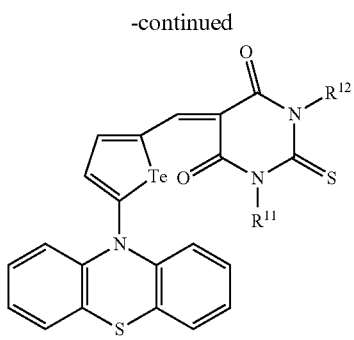

61
-continued
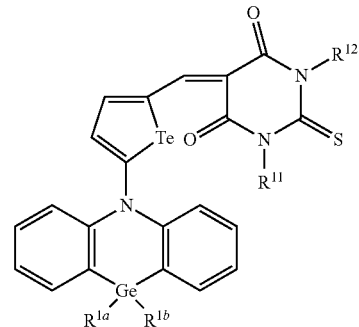
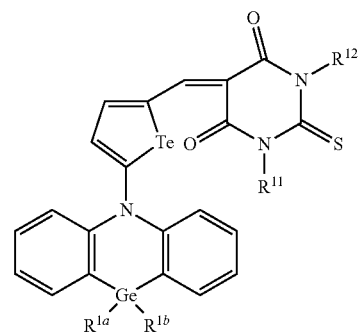
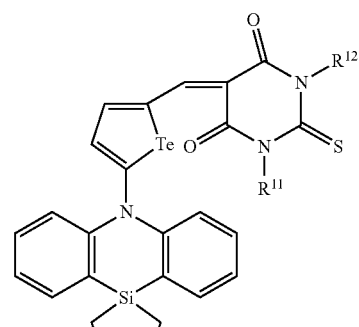
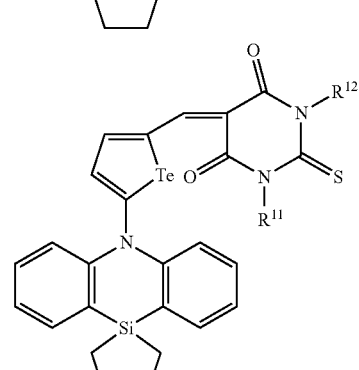
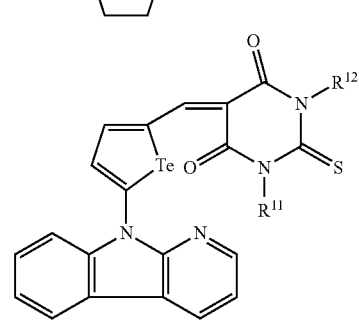
62
-continued
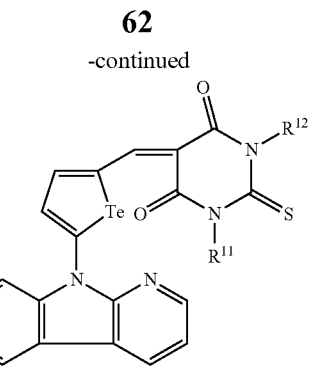
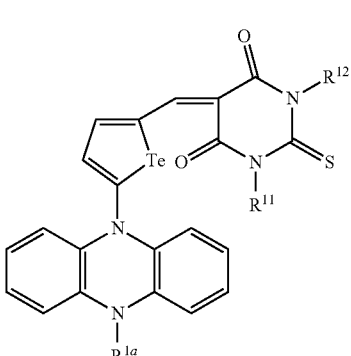
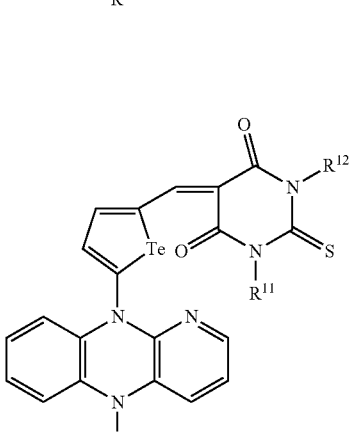
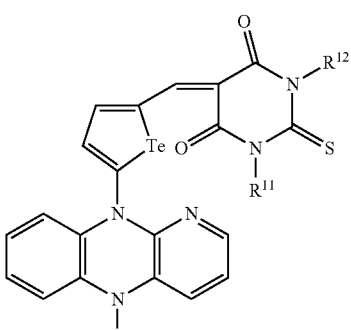
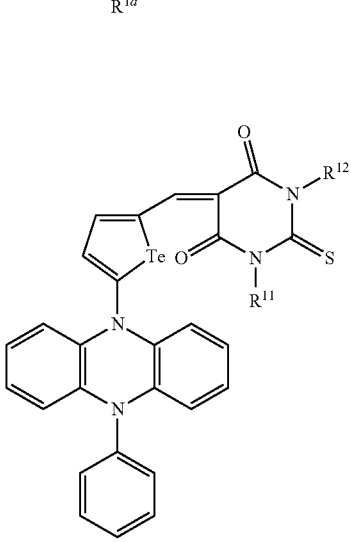

-continued
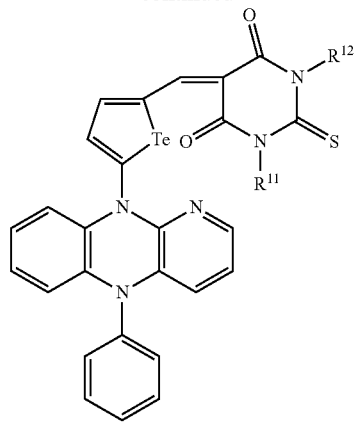
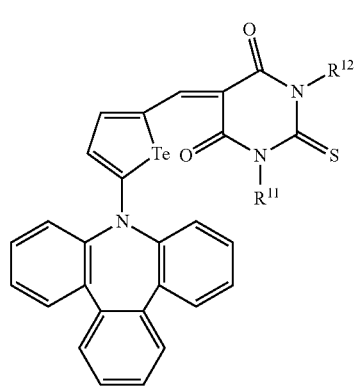
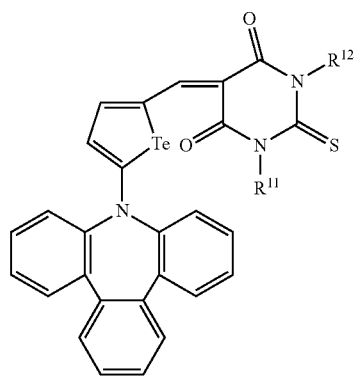
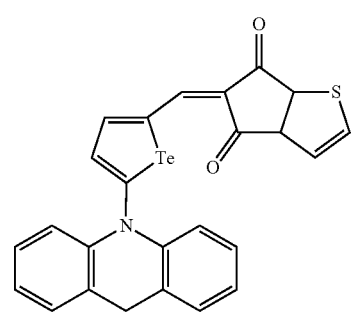
-continued
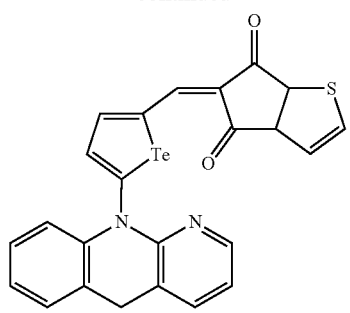
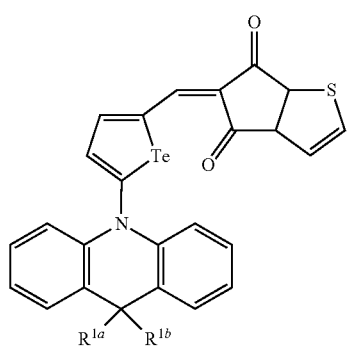
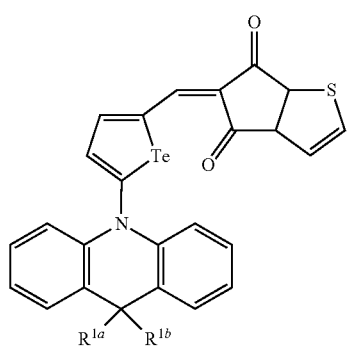
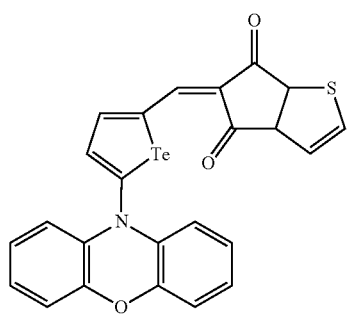
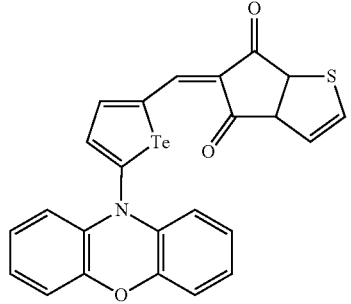

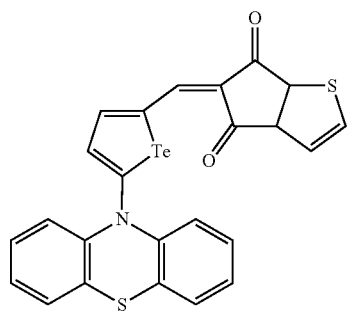
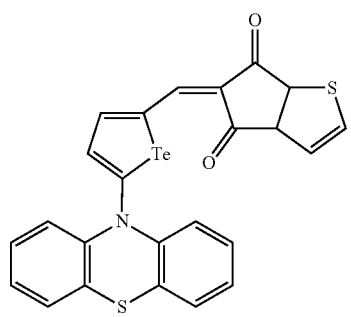
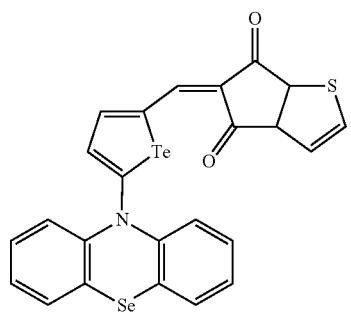
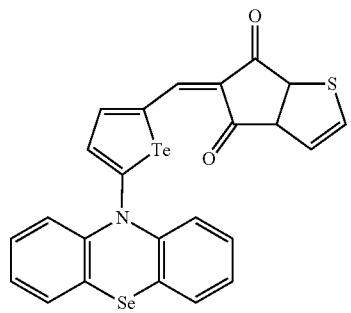
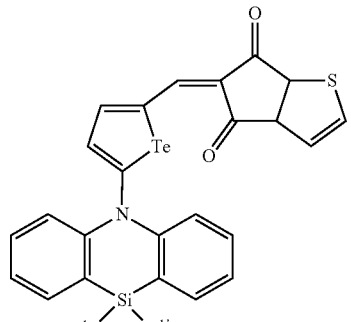
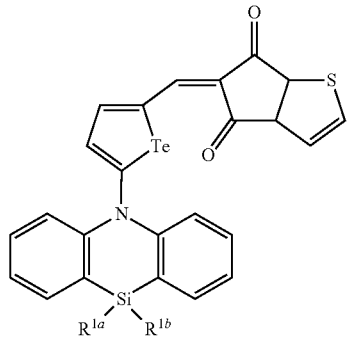
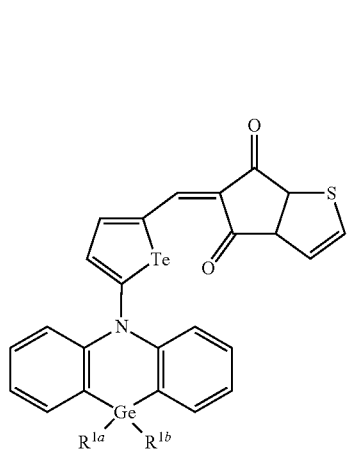
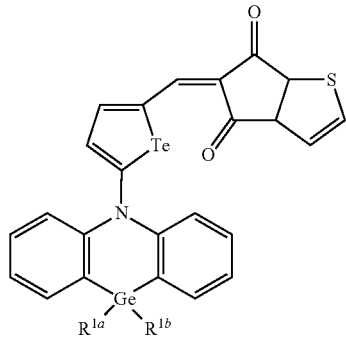
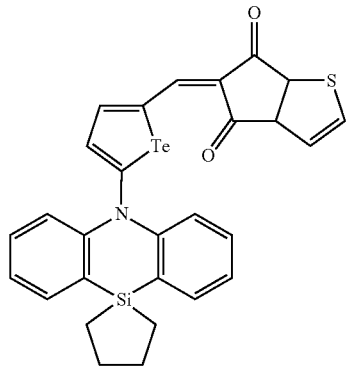

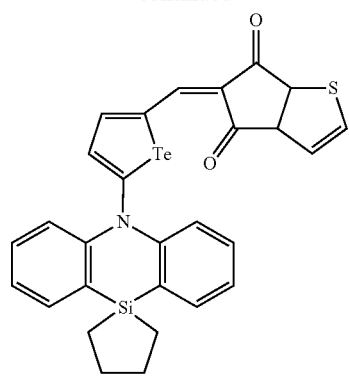
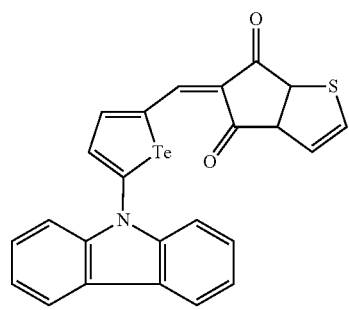
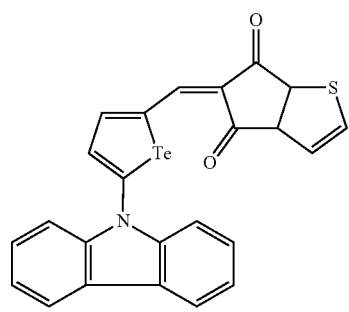
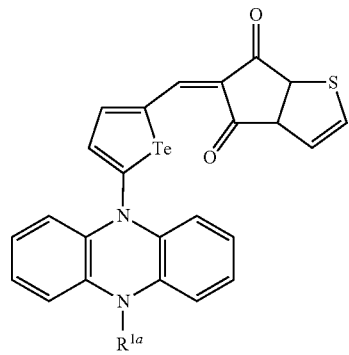
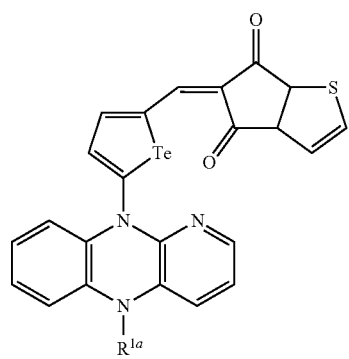
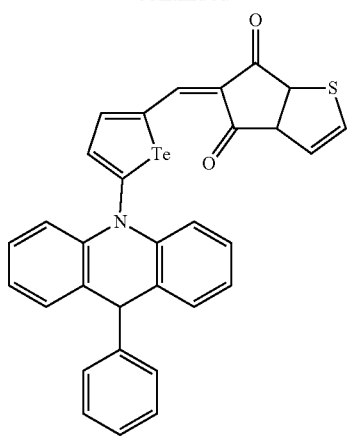
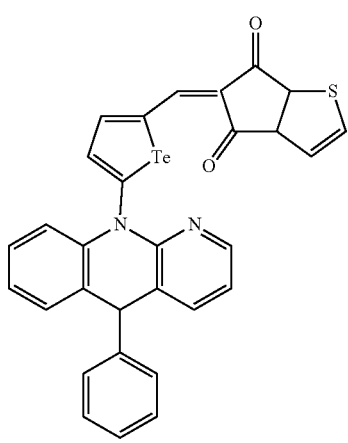
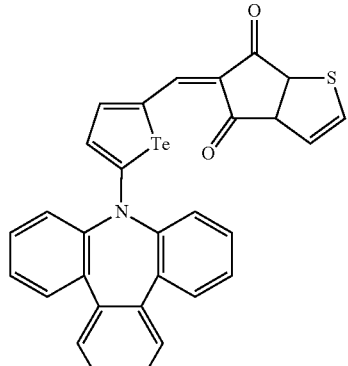
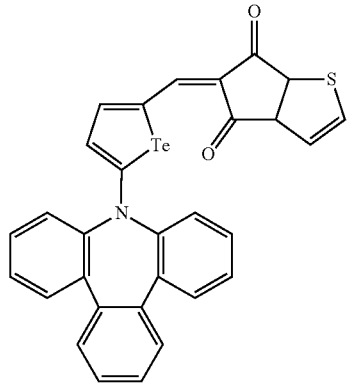

69
-continued
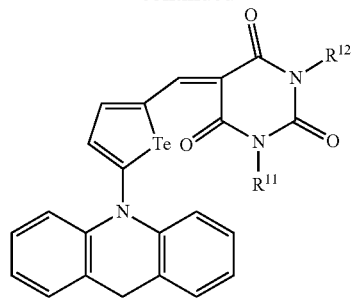
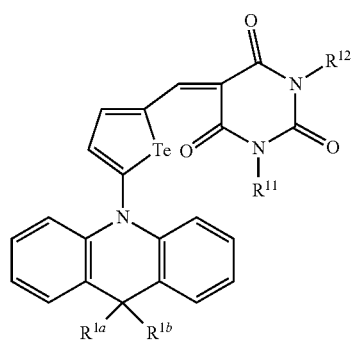
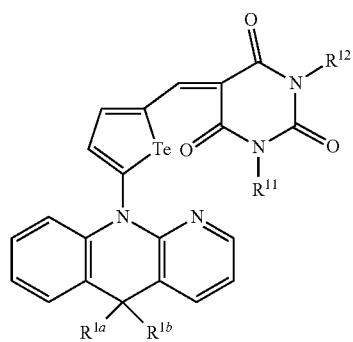
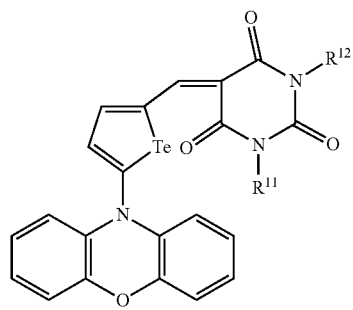
70
-continued
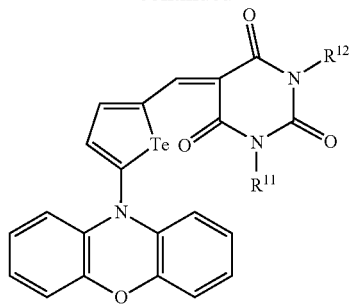
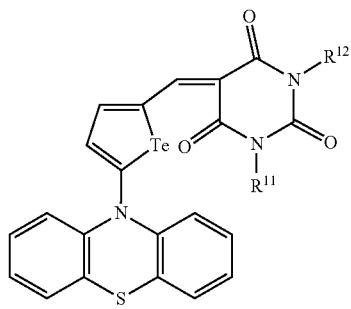
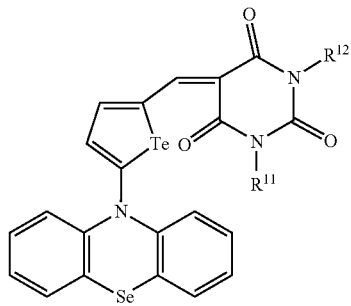
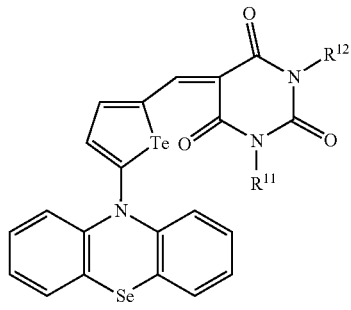

-continued
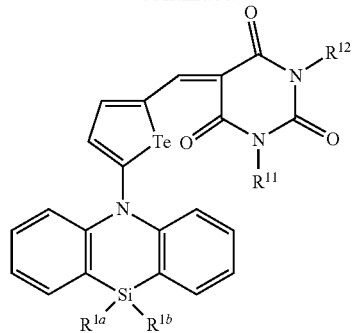
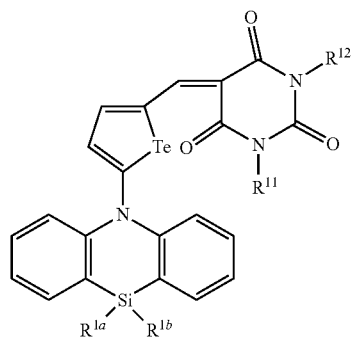
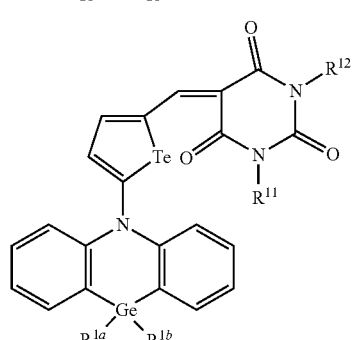
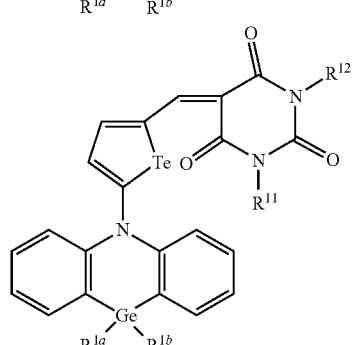
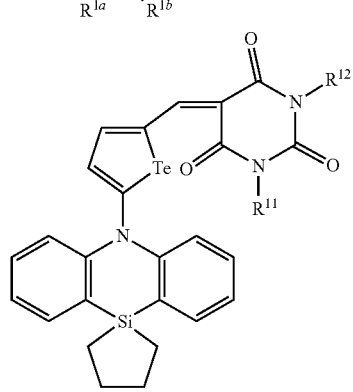
-continued
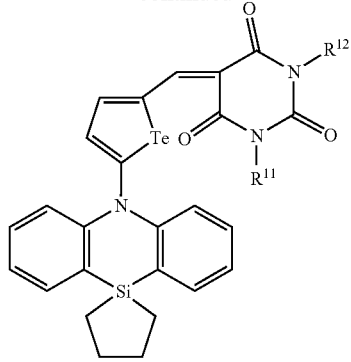
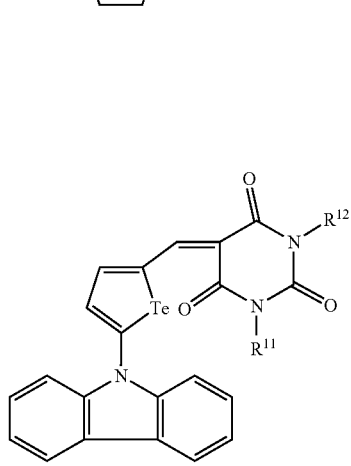
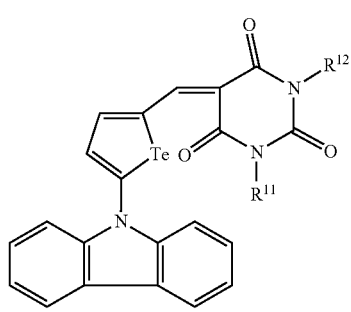
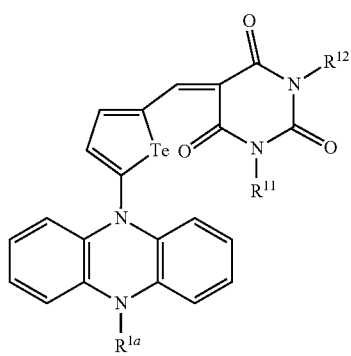
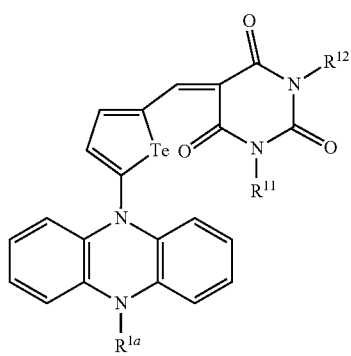

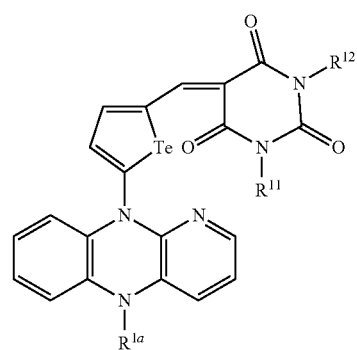
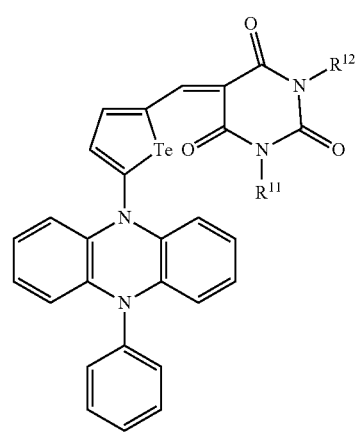
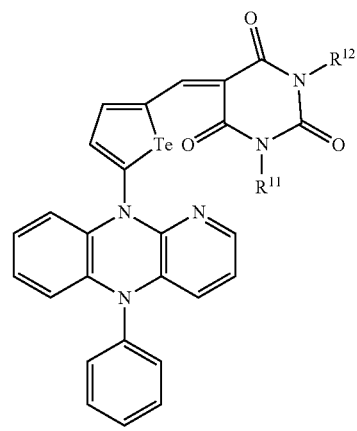
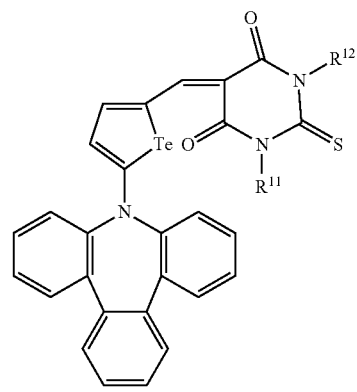
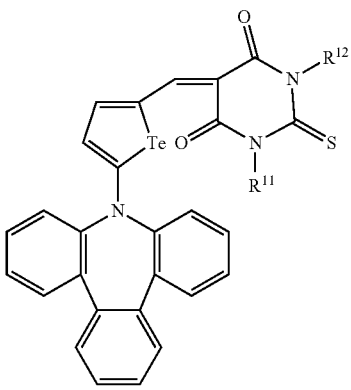
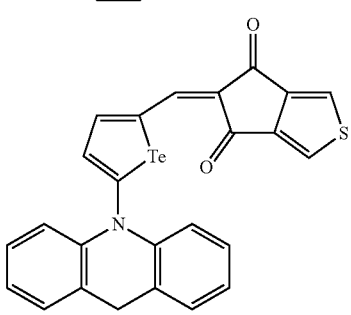
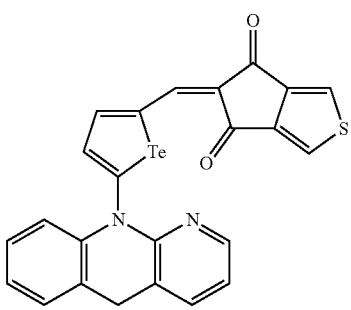
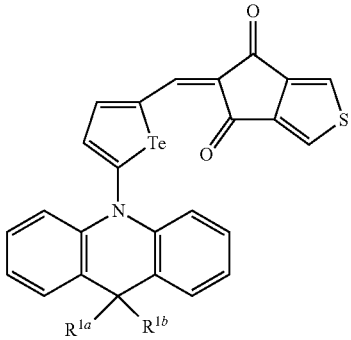
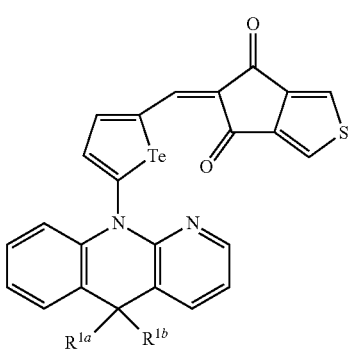

75
-continued
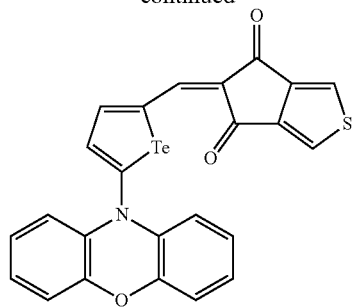
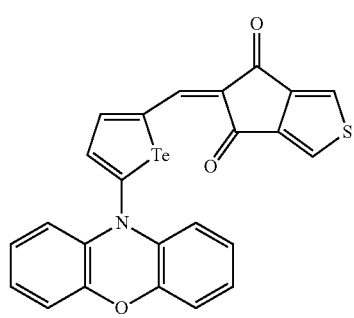
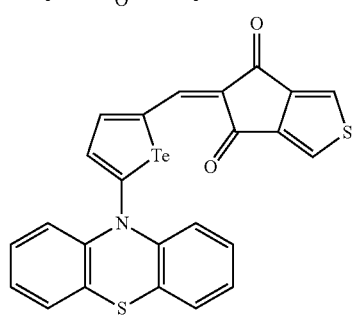
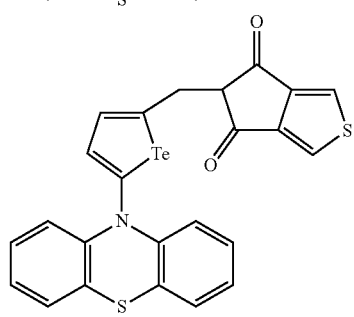
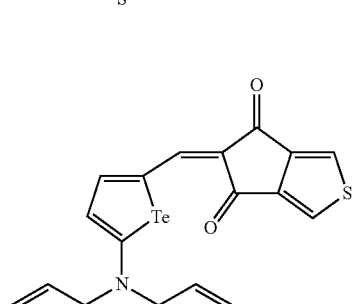
76
-continued
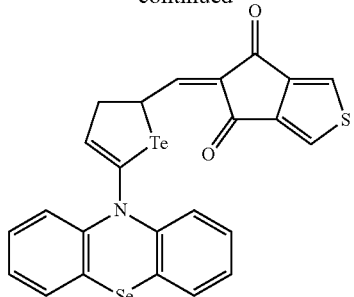
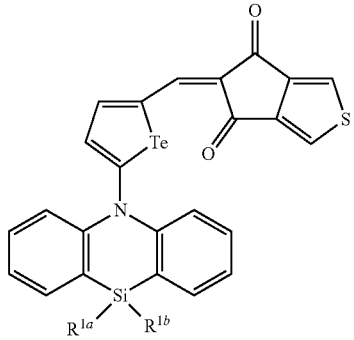
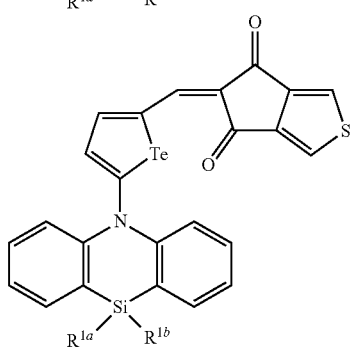
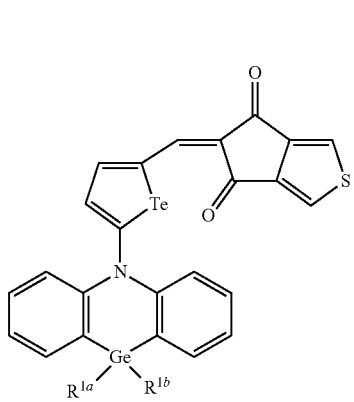
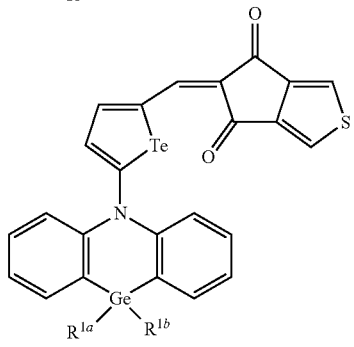

77
-continued
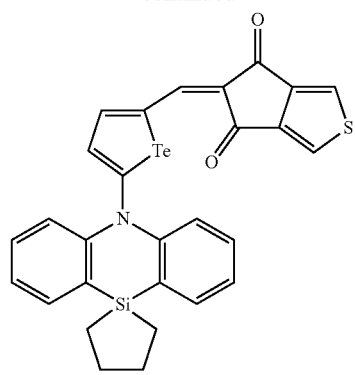
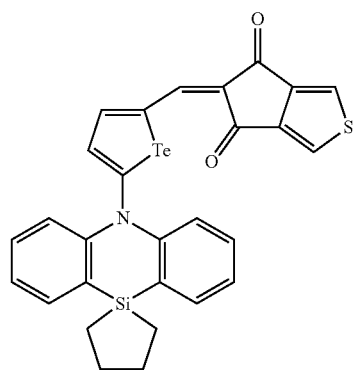
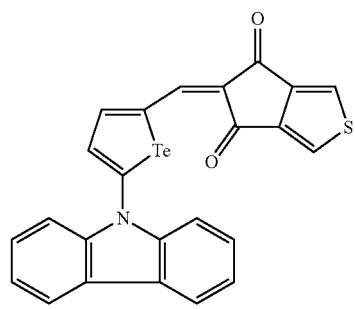
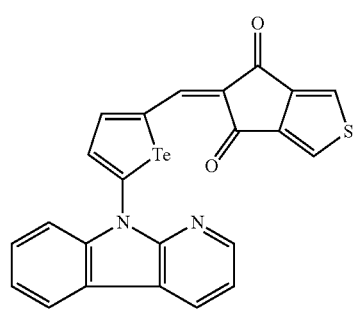
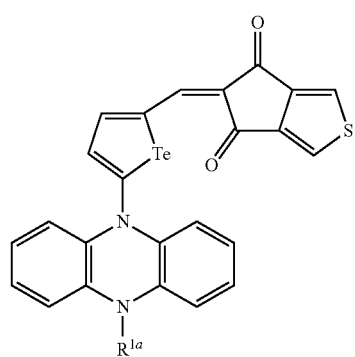
78
-continued
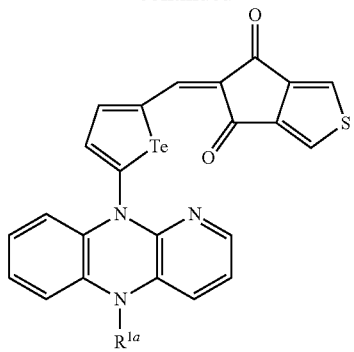
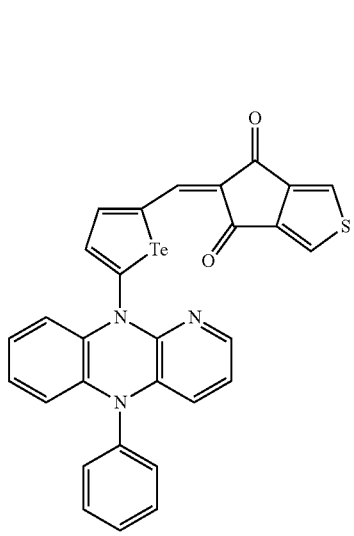
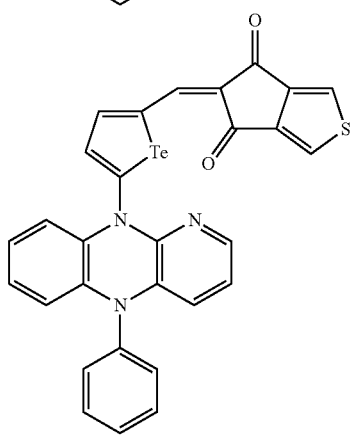
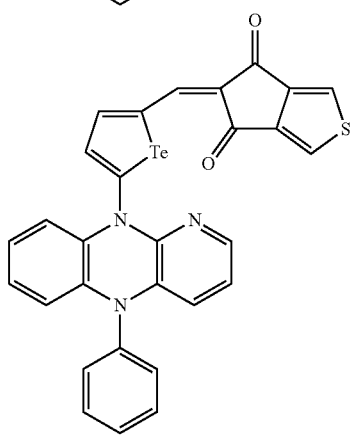
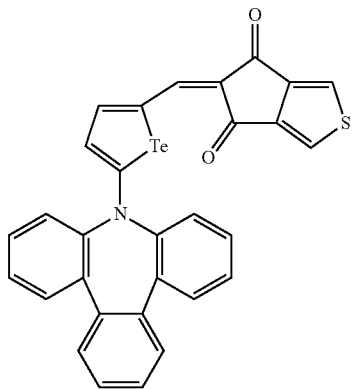

-continued

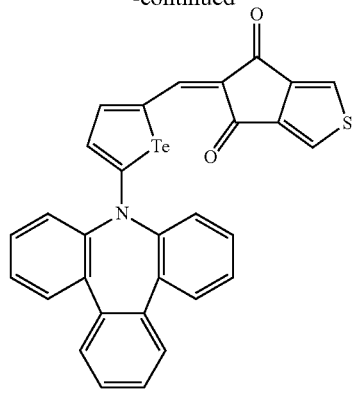

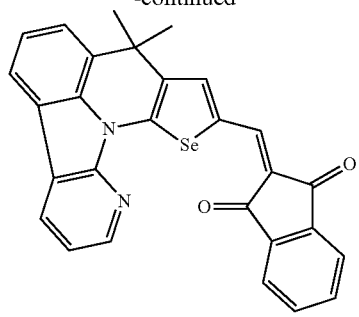

In Group 2B, at least one hydrogen of each aromatic ring or heteroaromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen (F, Cl, Br, or I), a cyano group (—CN), a cyano-containing group, and any combination thereof, and $R^{1a}$, $R^{1b}$, $R^{11}$, and $R^{12}$ may each independently be hydrogen or a C1 to C6 alkyl group.

[Group 2C]

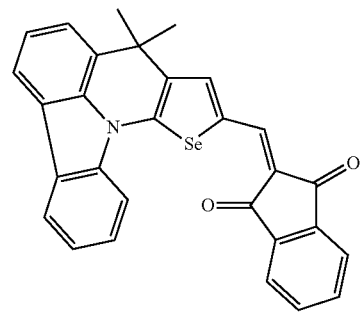

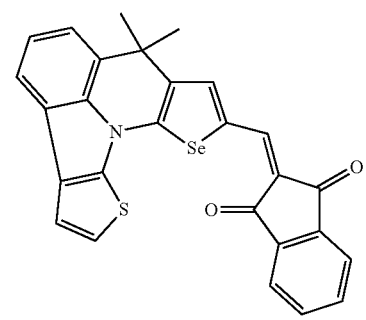

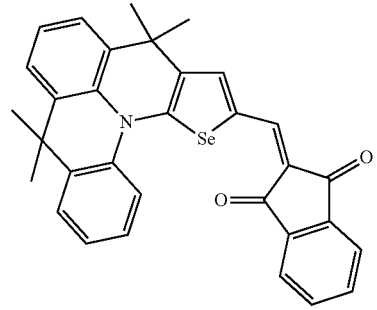

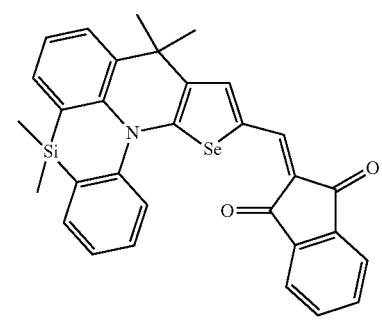

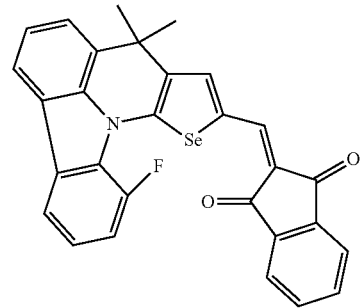

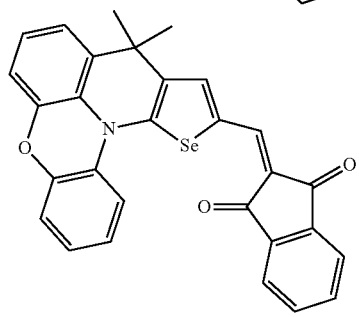

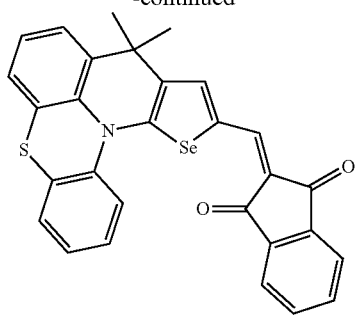
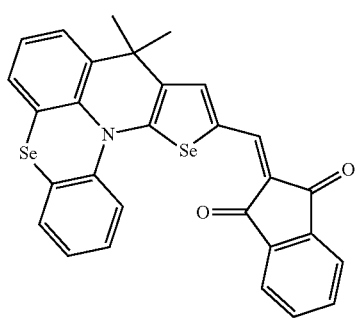
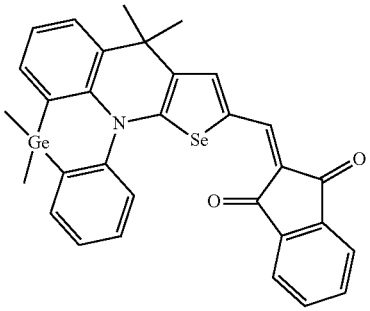
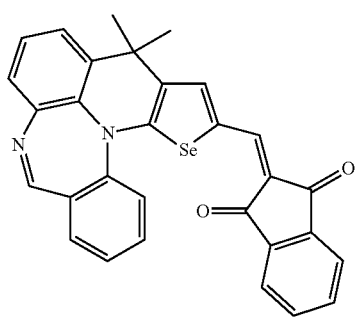
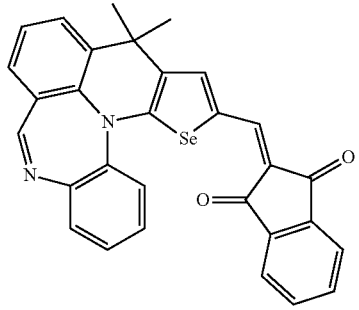
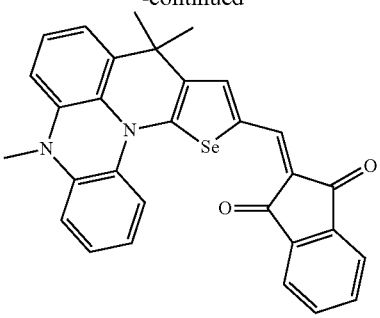
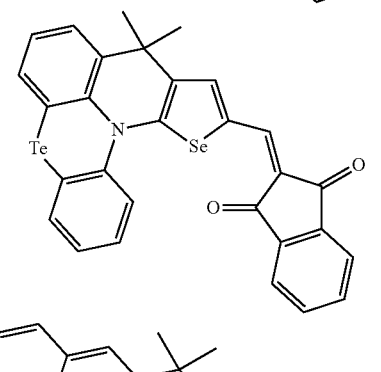
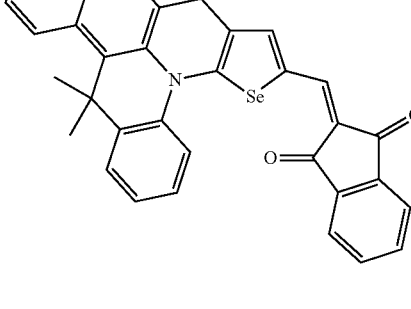
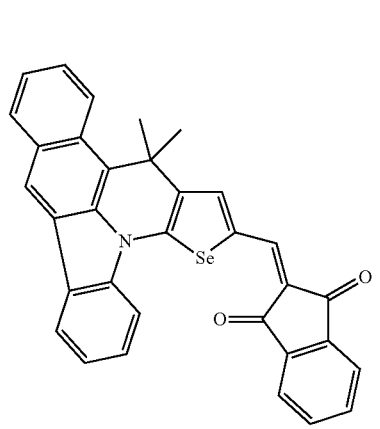
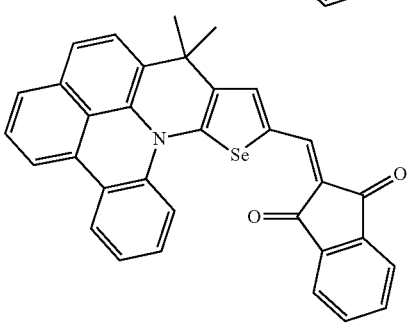

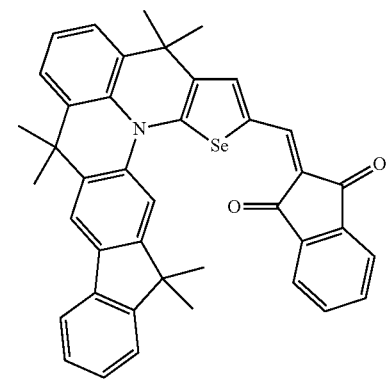
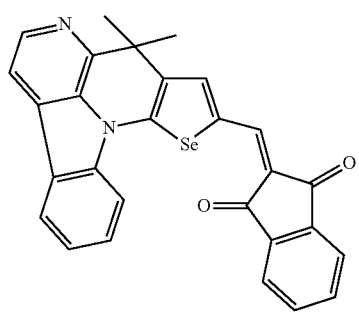
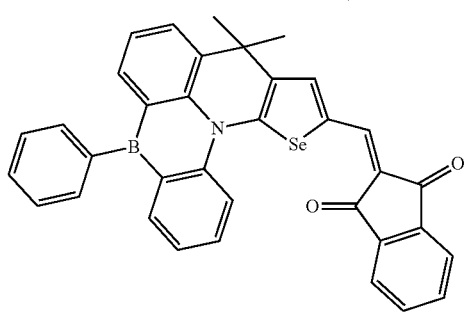
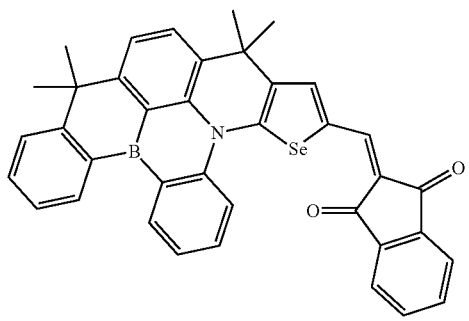
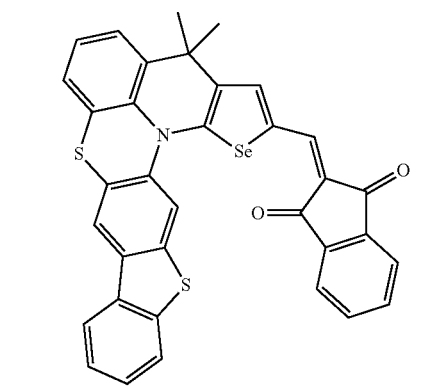
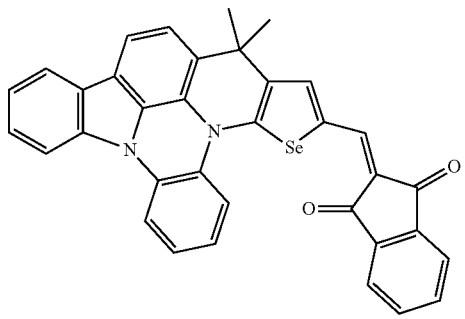
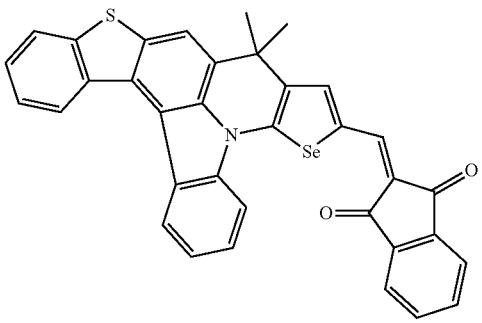
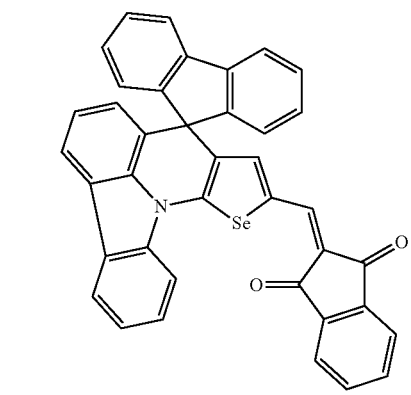
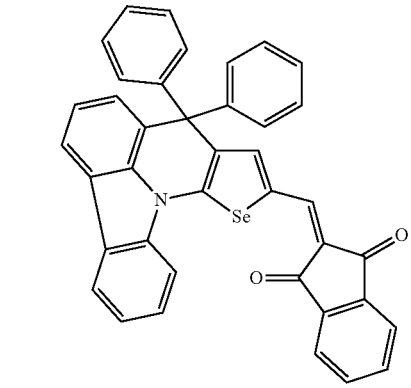

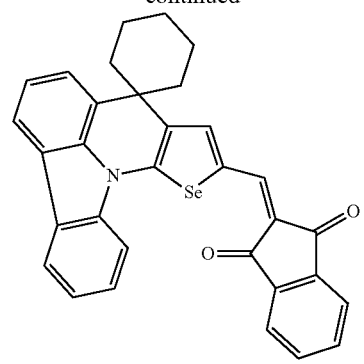
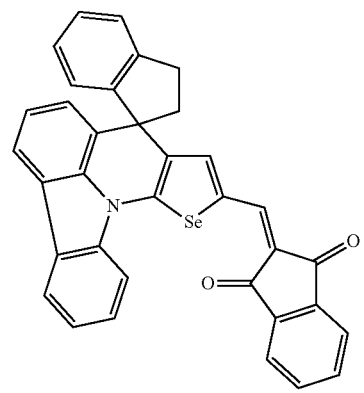
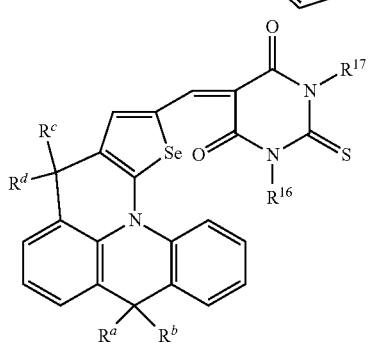
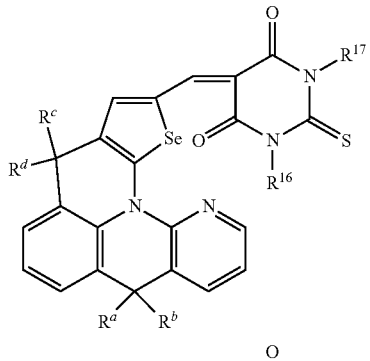
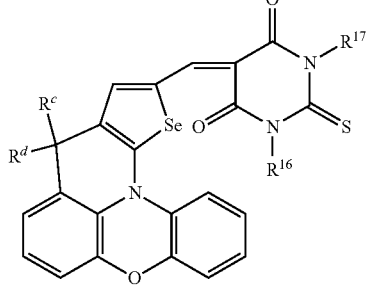
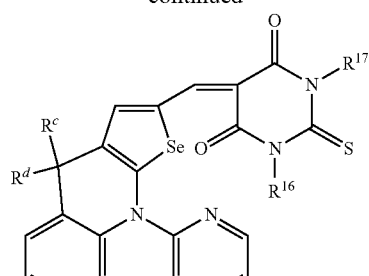
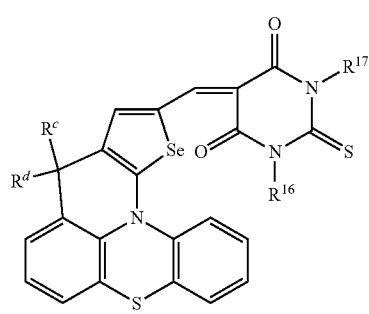
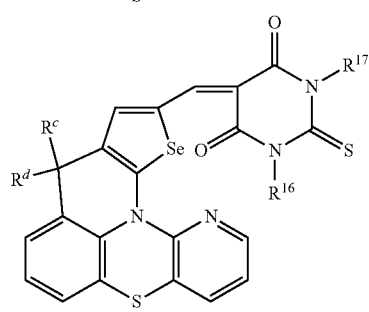
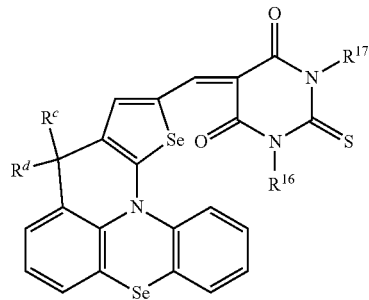
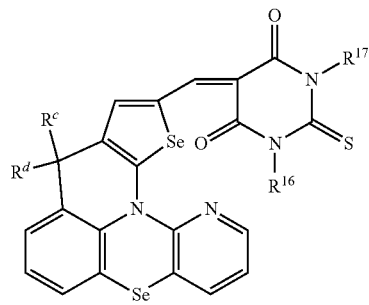

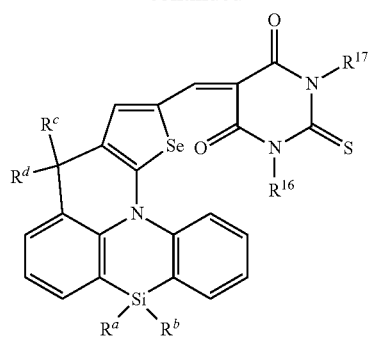
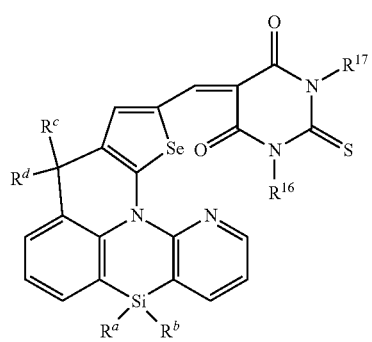
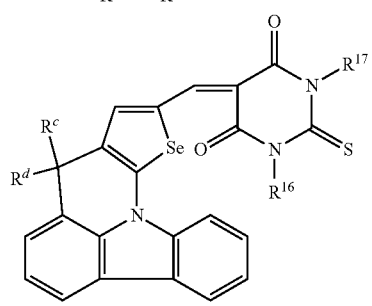
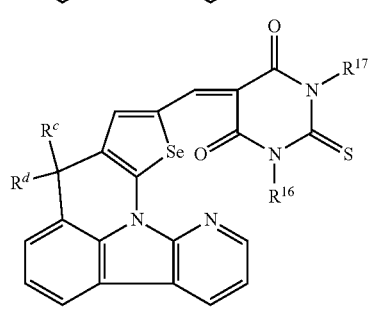
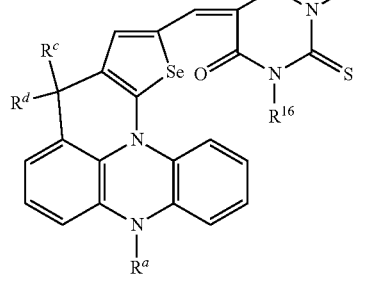
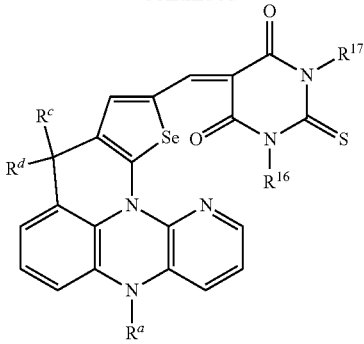
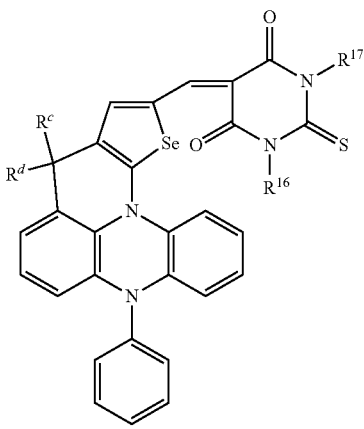
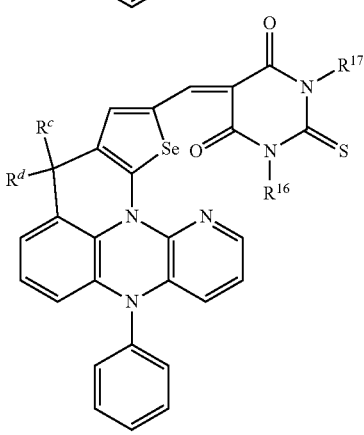
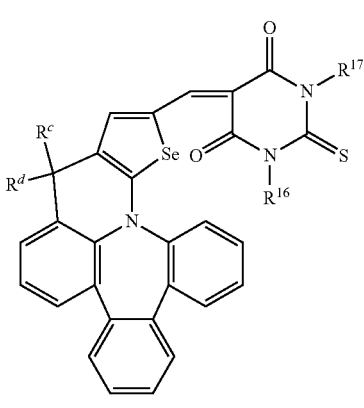

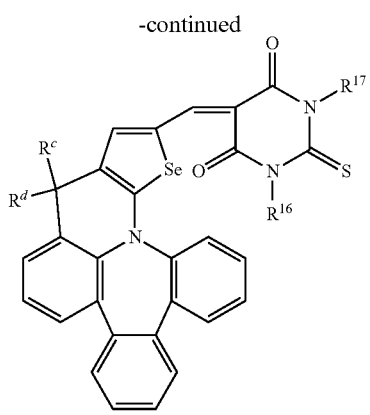

In Group 2C, at least one hydrogen of each aromatic ring or heteroaromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted a C4 to C30 heteroaryl group, a halogen (F, Cl, Br, or I), a cyano group (—CN), a cyano-containing group, and combinations thereof, and $R^a$, $R^b$, $R^c$, $R^d$, $R^{16}$, and $R^{17}$ may each independently be hydrogen or a C1 to C6 alkyl group.

The light absorbing layer 330 may be an intrinsic layer (I layer) in which a second organic material and a third organic material are blended in a bulk heterojunction form. In this case, the p-type semiconductor and the n-type semiconductor may be blended in a volume ratio (thickness ratio) of about 1:9 to about 9:1, and within the above range, for example, in a volume ratio (thickness ratio) of about 2:8 to about 8:2, about 3:7 to about 7:3, about 4:6 to about 6:4, or about 5:5.

The light absorbing layer 330 may include a p-layer and/or an n-layer instead of the intrinsic layer (I-layer) or further include a p-layer and/or an n-layer disposed on the upper portion and/or the lower portion of the intrinsic layer (I-layer). The p layer may include, for example, the aforementioned third organic material and the n layer may include, for example, the aforementioned second organic material. The light absorbing layer 330 may be, for example, an I-layer, a p-layer/n-layer, a p-layer/I-layer, an I-layer/n-layer, or a p-layer/I-layer/n-layer, but is not limited thereto.

The light emitting layers 212, 222, 232 and the light absorbing layer 330 may each independently have a thickness of about 5 nm to about 300 nm, and for example about 10 nm to about 250 nm, about 20 nm to about 200 nm, or about 30 nm to about 180 nm within the above range. The difference between the thicknesses of the light emitting layers 212, 222, 232 and the light absorbing layer 330 may be less than or equal to about 20 nm, within the above range, less than or equal to about 15 nm, less than or equal to about 10 nm, or less than or equal to about 5 nm. The light emitting layers 212, 222, and 232 and the light absorbing layer 330 may have substantially the same thickness.

An encapsulation layer 50 may be formed on the first, second, and third light emitting elements 210, 220, and 230 and the light absorption sensor 300. The encapsulation layer 50 may include, for example, a glass plate, a metal thin film, an organic film, an inorganic film, an organic-inorganic film, or any combination thereof. The organic film may include, for example, an acrylic resin, a (meth)acrylic resin, polyisoprene, a vinyl resin, an epoxy resin, a urethane resin, a cellulose, perylene, or any combination thereof, but is not limited thereto. The inorganic film may include, for example, oxides, nitrides and/or oxynitrides, for example silicon oxide, silicon nitride, silicon oxynitride, aluminum oxide, aluminum nitride, aluminum oxynitride, zirconium oxide, zirconium nitride, zirconium oxynitride, titanium oxide, titanium nitride, titanium oxynitride, hafnium oxide, hafnium nitride, hafnium oxynitride, tantalum oxide, tantalum nitride, tantalum oxynitride, lithium fluoride, or any combination thereof, but is not limited thereto. The organic-inorganic film may include, for example, polyorganosiloxane, but is not limited thereto. The encapsulation layer 50 may have one or two or more layers.

As described above, the sensor-embedded display panel 1000 according to some example embodiments includes the first, second, and third light emitting elements 210, 220, and 230 for displaying colors by emitting light of a particular (or, alternatively, predetermined) wavelength spectrum, and the light absorption sensor 300 configured to absorb the light generated by reflection of the light by the light recognition target 40 and convert the absorbed light into an electrical signal in the same plane on the substrate 110, and thereby the display function and the recognition function (e.g., biometric recognition function) may be performed together. Accordingly, high performance slim-type sensor-embedded display panel 1000 may be implemented without increasing the thickness, unlike the conventional display panel in which a sensor is manufactured as a separate module and then is attached to the outside of the display panel or formed under the display panel.

In addition, since the light absorption sensor 300 uses the light emitted from the first, second, and third light emitting elements 210, 220, and 230, a recognition function (e.g., a biometric recognition function) may be performed without a separate light source. Therefore, since there is no need to provide a separate light source outside the display panel, it is possible to reduce or prevent a decrease of the aperture ratio of the display panel due to the area occupied by the separate light source, and at the same time to save the power consumed by the separate light source, improving power consumption of the sensor-embedded display panel 1000.

In addition, as described above, the first, second, and third light emitting elements 210, 220, and 230 and the light absorption sensor 300 share the common electrode 320 (e.g., include separate portions of a common electrode 320 that is a single piece of material), the first common auxiliary layer 340 (e.g., include separate portions of a first common auxiliary layer 340 that is a single piece of material), and the second common auxiliary layer 350 (e.g., include separate portions of a second common auxiliary layer 350 that is a single piece of material), and thereby the structure and process may be simplified compared with the case of forming the first, second, and third light emitting elements 210, 220, and 230 and the light absorption sensor 300 through separate processes.

In addition, as described above, the light absorption sensor 300 may be an organic photoelectric diode including an organic light absorbing layer. Accordingly, the light absorption sensor 300 may have a light absorption that is twice or more higher than that of an inorganic diode such as a silicon photodiode and thus may have a high-sensitivity sensing function.

In addition, as described above, the light absorbing layer 330 of the light absorption sensor 300 includes the second organic material having good electrical matching with the first common auxiliary layer 340 and the third organic material configured to absorb light of at least a portion of the visible light wavelength spectrum, and thereby, electrical characteristics and light absorption characteristics of the light absorption sensor 300 may be simultaneously improved. In addition, by selecting a transparent n-type semiconductor as the second organic material and a light absorbing material having wavelength selectivity as the third organic material, the sensitivity to light in the red wavelength spectrum, green wavelength spectrum, or blue wavelength spectrum may be selectively increased and color separation characteristics may be improved without mixing absorption spectra. Accordingly, the sensor-embedded display panel 1000 may additionally implement an anti-spoofing effect in addition to the aforementioned effect, and thus the color separation characteristics of the light reflected by the recognition target 40 may be improved, thereby further increasing the detail of the shape of the recognition target 40 and the color of the reflected light (e.g., skin color) may be selectively recognized, thereby further enhancing the accuracy of the biometric recognition function.

In addition, as described above, the organic material included in the light absorbing layer 330 of the light absorption sensor 300 has a sublimation temperature difference within a particular (or, alternatively, predetermined) range with the organic materials of the light emitting layers 212, 222, and 232 of the first, second and third light emitting elements 210, 220, and 230, and thus deposition may be performed in the same process, thereby simplifying the process and increasing process stability.

Also, as described above, since the light absorption sensor 300 may be disposed anywhere in the non-display area NDA (e.g., anywhere in a portion of the sensor-embedded display panel 1000 that does not vertically overlap (e.g., in the z direction) within any light emitting elements and thus is not configured to emit light and/or display color), a desired number (e.g., quantity) of light absorption sensors 300 in the sensor-embedded display panel 1000 may be disposed at a desired location in the sensor-embedded display panel 1000. Therefore, for example, by randomly or regularly disposing/distributing a plurality of light absorption sensors 300 over the entire area of sensor-embedded display panel 1000, the biometric recognition function may be performed on any part of the screen of the electronic device such as a mobile device, and the biometric recognition function may be selectively performed at a specific location alone where the biometric recognition function is required according to the user's selection.

In some example embodiments, the light absorption sensor 300 may be provided separately from (e.g., independently of) a sensor-embedded display panel 1000 and/or from any light emitting elements, for example as a separate component of an electronic device. For example, an electronic device, such as the electronic device 2000 shown in FIG. 5, may include a plurality of light absorption sensors 300, as a separate at least one additional device 1340, to serve as a camera or biometric sensor for the electronic device separately from any light emitting elements and/or display panels of the electronic device 2000.

Hereinafter, another example of the sensor-embedded display panel 1000 according to some example embodiments is described.

Figure 3:
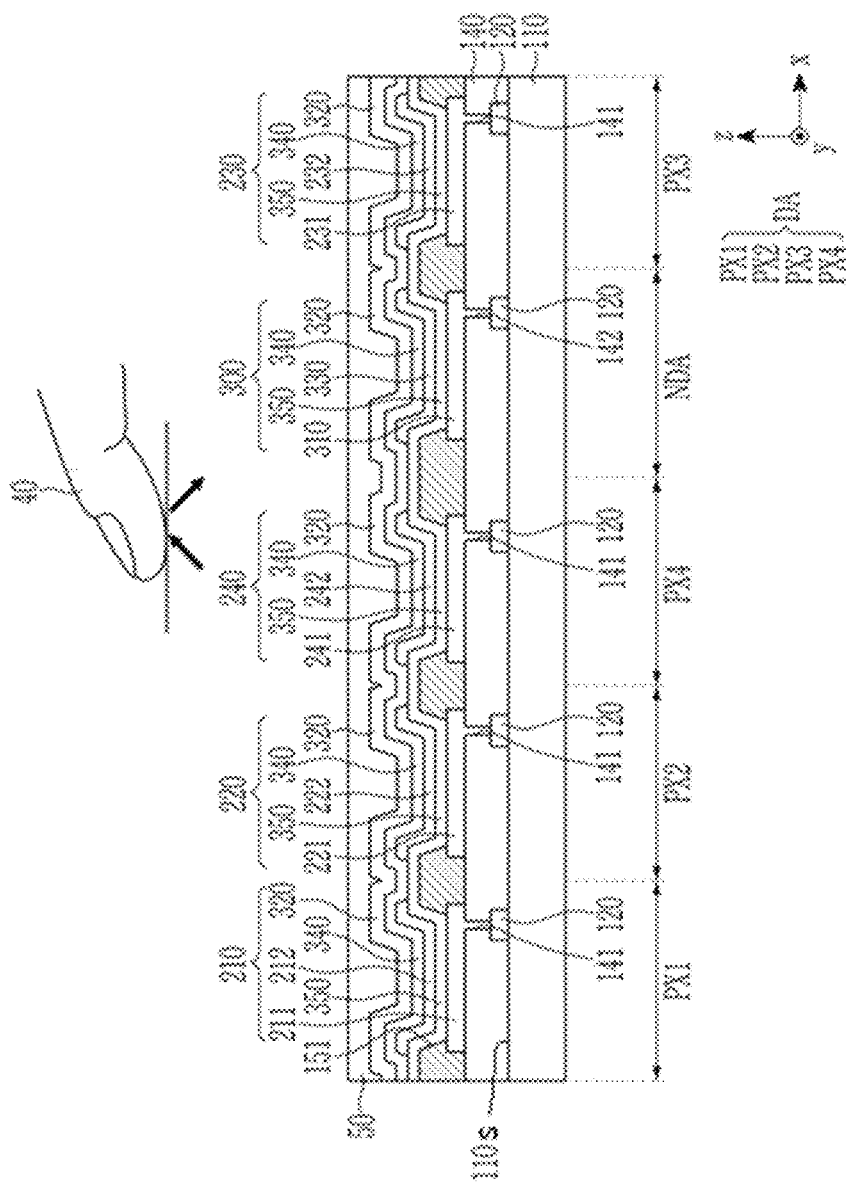
FIG. 3 is a cross-sectional view illustrating another example of a sensor-embedded display panel according to some example embodiments.

FIG. 3 is a cross-sectional view illustrating another example of a sensor-embedded display panel according to some example embodiments.

Referring to FIG. 3, a sensor-embedded display panel 1000 according to some example embodiments includes a plurality of subpixels PX configured to display different colors, that is, a first subpixel PX1, a second subpixel PX2, and a third subpixel PX3 displaying a first color, a second color, and a third color selected from red, green, and blue, and the first subpixel PX1, the second subpixel PX2, and the third subpixel PX3 include a first light emitting element 210, a second light emitting element 220, and a third light emitting element 230, respectively, like some example embodiments, including the example embodiments shown in FIGS. 1 and 2.

However, unlike the some example embodiments, including the example embodiments shown in FIGS. 1 and 2, the sensor-embedded display panel 1000 according to some example embodiments, including the example embodiments shown in FIG. 3, may include the fourth light emitting element 240 configured to emit light in an infrared wavelength spectrum. For example, the fourth light emitting element 240 may be included in the fourth subpixel PX4 adjacent to the first subpixel PX1, the second subpixel PX2, and/or the third subpixel PX3, or may be included in a non-display area, NDA. The fourth subpixel PX4 may form one unit pixel UP together with the first subpixel PX1, the second subpixel PX2, and the third subpixel PX3, and the unit pixel UP may be arranged repeatedly along rows and/or columns.

Descriptions of the first subpixel PX1, the second subpixel PX2, the third subpixel PX3, the first light emitting element 210, the second light emitting element 220, and the third light emitting element 230 are the same as described above.

The fourth light emitting element 240 is disposed on the substrate 110 and may be disposed on the same plane as the first, second, and third light emitting elements 210, 220, and 230 and the light absorption sensor 300. The fourth light emitting element 240 may be electrically connected to a separate thin film transistor 120 and driven independently. The fourth light emitting element 240 may have a structure in which the pixel electrode 241, the second common auxiliary layer 350, the light emitting layer 242, the first common auxiliary layer 340, and the common electrode 320 are sequentially stacked. Among them, the common electrode 320, the first common auxiliary layer 340, and the second common auxiliary layer 350 may be shared with the first, second, and third light emitting elements 210, 220, and 230, and the light absorption sensor 300. The light emitting layer 242 may be configured to emit light of an infrared wavelength spectrum, which may have for example a maximum emission wavelength in a range of greater than or equal to about 750 nm, about 750 nm to about 20 μm, about 780 nm to about 20 μm, about 800 nm to about 20 μm, about 750 nm to about 15 μm, about 780 nm to about 15 μm, about 800 nm to about 15 μm, about 750 nm to about 10 μm, about 780 nm to about 10 μm, about 800 nm to about 10 μm, about 750 nm to about 5 μm, about 780 nm to about 5 μm, about 800 nm to about 5 μm, about 750 nm to about 3 μm, about 780 nm to about 3 μm, about 800 nm to about 3 μm, about 750 nm to about 2 μm, about 780 nm to about 2 μm, about 800 nm to about 2 μm, about 750 nm to about 1.5 μm, about 780 nm to about 1.5 μm, or about 800 nm to about 1.5 μm.

The light absorption sensor 300 may be configured to absorb light generated by reflection of light emitted from at least one of the first, second, third, or fourth light emitting elements 210, 220, 230, and 240, from a recognition target 40 such as a living body or a tool, and then convert the absorbed light into an electrical signal. For example, the light absorption sensor 300 may be configured to absorb light generated by reflection of light emitted from the fourth light emitting element 240 in an infrared wavelength spectrum, by the recognition target 40, and then convert it into an electrical signal. In this case, the light absorbing layer 330 of the light absorption sensor 300 may include an organic material, an inorganic material, an organic-inorganic material, or any combination thereof configured to selectively absorb light in the infrared wavelength spectrum. For example, the light absorbing layer 330 may include a quantum dot, a quinoid metal complex compound, a polymethine compound, a cyanine compound, a phthalocyanine compound, a merocyanine compound, a naphthalocyanine compound, an immonium compound, a diimmonium compound, a triarylmethane compound, a dipyrromethene compound, an anthraquinone compound, a naphthoquinone, a diquinone compound, a naphthoquinone compound, an anthraquinone compound, a squarylium compound, a rylene compound, a perylene compound, a pyrylium compound, a squaraine compound, a thiopyrylium compound, a diketopyrrolopyrrole compound, a boron dipyrromethene compound, a nickel-dithiol complex compound, a croconium compound, a derivative thereof, or any combination thereof, but is not limited thereto. For example, a material configured to selectively absorb light in the infrared wavelength spectrum may be included as a p-type semiconductor, and the aforementioned second organic material may be included as an n-type semiconductor.

The sensor-embedded display panel 1000 according to some example embodiments, including the example embodiments shown in FIG. 3, includes the fourth light emitting element 240 configured to emit light in the infrared wavelength spectrum and the light absorption sensor 300 configured to absorb light in the infrared wavelength spectrum. Therefore, in addition to the recognition function (biometric recognition function), the sensitivity of the light absorption sensor 300 may be improved even in a low-illumination environment, and the detection capability of a 3D image may be further increased by widening a dynamic range for detailed division of black and white contrast. Accordingly, the sensing capability of the sensor-embedded display panel 1000 may be further improved. In particular, since light in the infrared wavelength spectrum may have a deeper penetration depth due to its long wavelength characteristics and information located at different distances may be effectively obtained, images or changes in blood vessels such as veins, iris and/or face, etc., in addition to fingerprints may be effectively detected, and the scope of application nay be further expanded.

The aforementioned sensor-embedded display panel 1000 may be applied to electronic devices such as various display devices. Electronic devices such as display devices may be applied to, for example, mobile phones, video phones, smart phones, mobile phones, smart pads, smart watches, digital cameras, tablet PCs, laptop PCs, notebook computers, computer monitors, wearable computers, televisions, digital broadcasting terminals, e-books, personal digital assistants (PDAs), portable multimedia player (PMP), enterprise digital assistant (EDA), head mounted display (HMD), vehicle navigation, Internet of Things (IoT), Internet of all things (IoE), drones, door locks, safes, automatic teller machines (ATM), security devices, medical devices, or automotive electronic components, but are not limited thereto.

Figure 4:
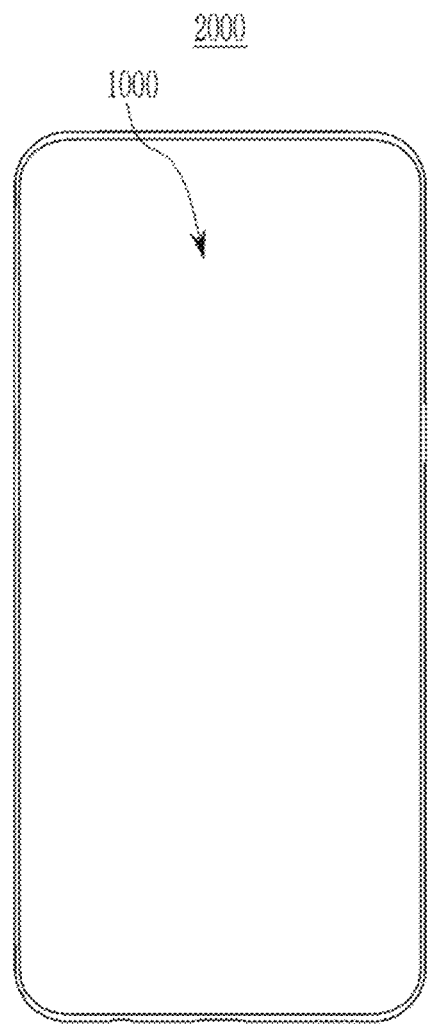
FIG. 4 is a schematic view illustrating an example of a smart phone as an electronic device according to some example embodiments.

FIG. 4 is a schematic view illustrating an example of a smart phone as an electronic device according to some example embodiments.

Referring to FIG. 4, the electronic device 2000 may include the aforementioned sensor-embedded display panel 1000, and the light absorption sensor 300 disposed in the whole or a part of the sensor-embedded display panel 1000, and thus a biometric recognition function may be performed on any part of the screen, and according to the user's selection, the biometric recognition function may be selectively performed at a specific location alone where the biometric recognition function is required.

An example of a method of recognizing the recognition target 40 in an electronic device 2000 such as a display device may include, for example, driving the first, second, and third light emitting elements 210, 220, and 230 of the sensor-embedded display panel 1000 (or the first, second, third, and fourth light emitting elements 210, 220, 230, and 240) and the light absorption sensor 300 to detect the light reflected by the recognition target 40 among the light emitted from the first, second, and third light emitting elements 210, 220, and 230 (or the first, second, third and fourth light emitting elements 210, 220, 230, and 240), in the light absorption sensor 300; comparing the image of the recognition target 40 stored in advance with the image of the recognition target 40 detected by the light absorption sensor 300; and judging the consistency of the compared images and if they match according to the determination that recognition of the recognition target 40 is complete, turning off the light absorption sensor 300, permitting user's access to the display device, and driving the sensor-embedded display panel 1000 to display an image.

Figure 5:
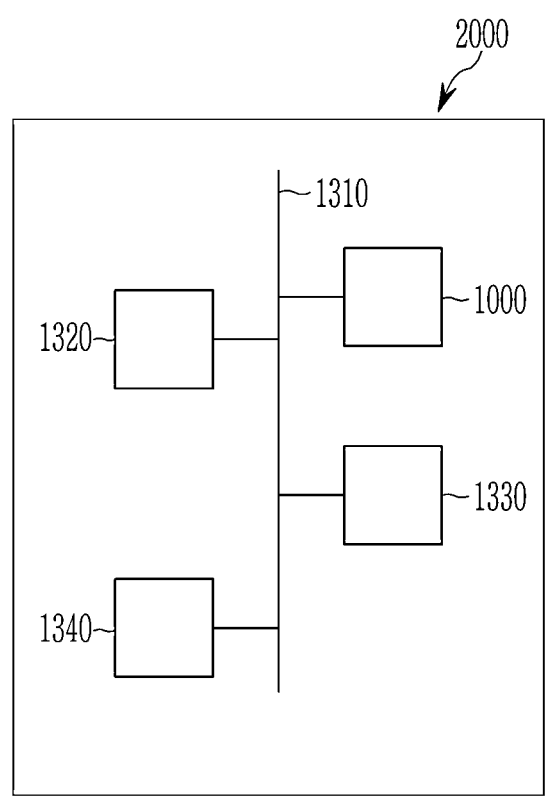
FIG. 5 is a schematic view illustrating an example of a configuration diagram of an electronic device according to some example embodiments.

FIG. 5 is a schematic view illustrating an example of a configuration diagram of an electronic device according to some example embodiments.

Referring to FIG. 5, in addition to the aforementioned constituent elements (e.g., the sensor-embedded display panel 1000), the electronic device 2000 may further include a bus 1310, a processor 1320, a memory 1330, and at least one additional device 1340. Information of the aforementioned sensor-embedded display panel 1000, processor 1320, memory 1330, and at least one additional device 1340 may be transmitted to each other through the bus 1310. In some example embodiments, the at least one additional device 1340 may be omitted. In some example embodiments, the sensor-embedded display panel 1000 may be replaced by a display device including, for example, exclusively light emitting elements and no light absorption sensors, while the at least one additional device 1340 may include one or a plurality (e.g., an array) of light absorption sensors according to any of the example embodiments which may serve as a biometric sensor, a camera, or the like.

The processor 1320 may include one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. As an example, the processing circuitry may include a non-transitory computer readable storage device. The processor 1320 may control, for example, a display operation of the sensor-embedded display panel 1000 or a sensor operation of the light absorption sensor 300.

The memory 1330 may be a non-transitory computer readable storage medium, such as, for example, as solid state drive (SSD) and may store an instruction program (e.g., program of instructions), and the processor 1320 may perform a function related to the sensor-embedded display panel 1000 by executing the stored instruction program.

The at least one additional device 1340 may include one or more communication interfaces (e.g., wireless communication interfaces, wired interfaces), user interfaces (e.g., keyboard, mouse, buttons, etc.), power supply and/or power supply interfaces, or any combination thereof.

The units and/or modules described herein may be implemented using hardware constituent elements and software constituent elements. The units and/or modules described herein may include, may be included in, and/or may be implemented by one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. For example, the hardware constituent elements may include microphones, amplifiers, band pass filters, audio-to-digital converters, and processing devices. The processing device may be implemented using one or more hardware devices configured to perform and/or execute program code by performing arithmetic, logic, and input/output operations. The processing device may include a processor, a controller and an arithmetic logic unit, a digital signal processor, a microcomputer, a field programmable array, a programmable logic unit, a microprocessor, or any other device capable of responding to and executing instructions. The processing device may access, store, operate, process, and generate data in response to execution of an operating system (OS) and one or more software running on the operating system.

The software may include a computer program, a code, an instruction, or any combination thereof, and may transform a processing device for a special purpose by instructing and/or configuring the processing device independently or collectively to operate as desired. The software and data may be implemented permanently or temporarily as signal waves capable of providing or interpreting instructions or data to machines, parts, physical or virtual equipment, computer storage media or devices, or processing devices. The software may also be distributed over networked computer systems so that the software may be stored and executed in a distributed manner. The software and data may be stored by one or more non-transitory computer readable storage devices.

The method according to any of the example embodiments may be recorded in a non-transitory computer readable storage device including program instructions for implementing various operations of the aforementioned example embodiments. The storage device may also include program instructions, data files, data structures, and the like alone or in combination. The program instructions recorded in the storage device may be specially designed for some example embodiments or may be known to those skilled in computer software and available for use. Examples of non-transitory computer-readable storage devices may include magnetic media such as hard disks, floppy disks, and magnetic tapes; optical media such as CD-ROM discs, DVDs and/or blue-ray discs; magneto-optical media such as optical disks; and a hardware device configured to store and execute program instructions such as ROM, RAM, flash memory, and the like. The aforementioned device may be configured to operate as one or more software modules to perform the operations of any of the example embodiments.

Hereinafter, some example embodiments are illustrated in more detail with reference to examples. However, the scope of the inventive concepts are not limited to these examples.

SYNTHESIS EXAMPLES

Synthesis Example 1

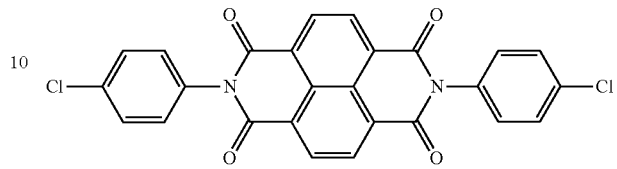

[Compound 1a]

A mixture of 1,4,5,8-naphthalenetetracarboxylic dianhydride (1 eq.) and 4-chloroaniline (2.2 eq.) is dissolved in a dimethyl formamide (DMF) solvent and then, stirred at 180° C. for 24 hours in a two-necked round-bottomed flask. Subsequently, after decreasing the temperature down to room temperature, methanol is added thereto to precipitate a product, and the product is filtered, obtaining a powder type material. Then, the material is several times washed with methanol and then, purified through recrystallization by using ethyl acetate and dimethylsulfoxide (DMSO). Subsequently, the obtained product is put in an oven and dried at 80° C. in a vacuum for 24 hours, obtaining Compound 1a. A yield thereof is 50% or more.

1H NMR (300 MHz, $CDCl_3$ with Hexafluoroisopropanol): 0=8.85 (s, 4H), 7.63 (s, 4H), 7.60 (s, 4H).

Synthesis Example 2

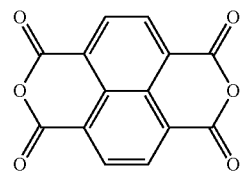

[Compound 1b]

Compound 1b (Tokyo Chemical Industry Co., Ltd.) is prepared by sublimation purification.

Reference Synthesis Example

Fullerene (C60, nanom purple ST, Frontier Carbon Corp.) is prepared.

Synthesis Example 3

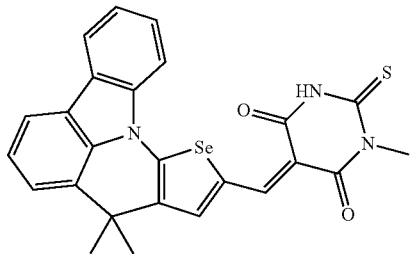

[Compound 2a]

[Reaction Scheme 1]

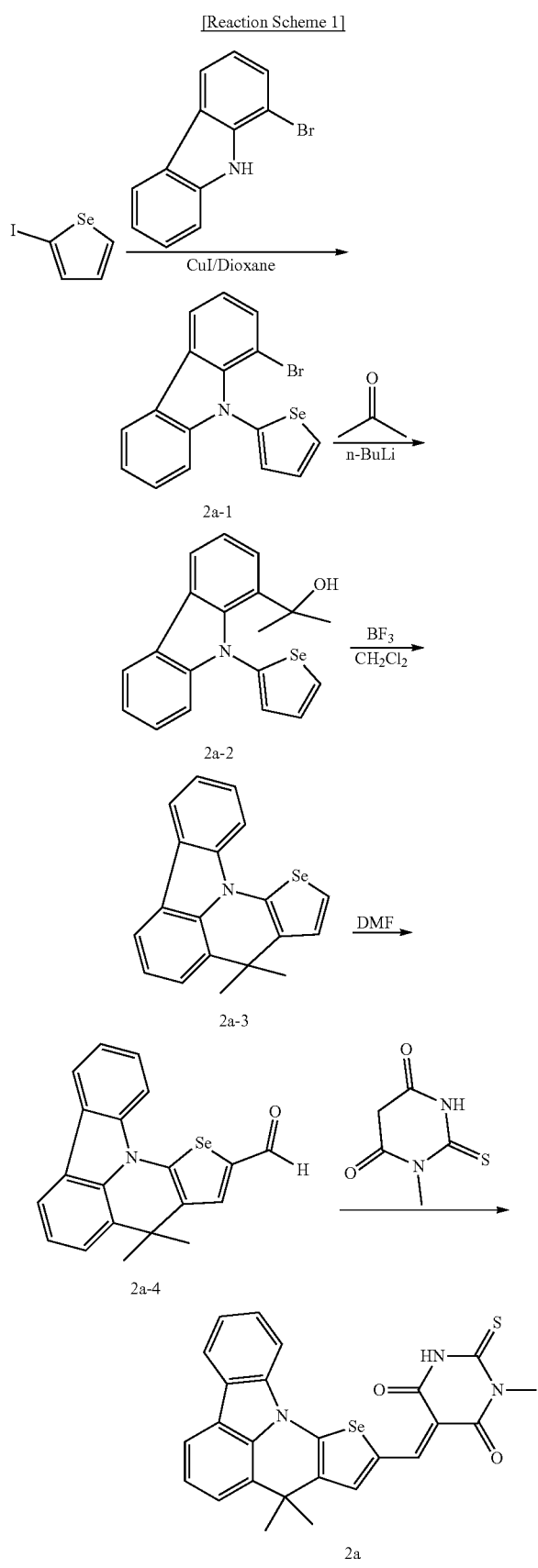

(i) Synthesis of Compound 2a-1

9.4 g (36.5 mmol) of 2-Iodoselenophene and 7.5 g (30.5 mmol) of 1-bromo-9H-carbazole are dissolved in 30 ml of dioxane. 0.29 g (1.52 mmol) of copper (I) Iodide, 0.70 g (6.09 mmol) of trans-1,2-cyclohexanediamine, and 12.9 g (61.0 mmol) of tripotassium phosphate are added thereto and then, heated and refluxed for 30 hours. A product obtained therefrom is separated and purified through silica gel column chromatography (in a volume ratio of hexane: ethyl acetate=5:1) to obtain 8.18 g (Yield: 72%) of Compound 2a-1.

(ii) Synthesis of Compound 2a-2

12.0 g (32.0 mmol) of Compound 2a-1 is dissolved in 300 ml of dehydrated diethyl ether. 12 ml (32.0 mmol) of a 2.76 M n-BuLi hexane solution is added thereto in a dropwise fashion at −50° C. and then, stirred for 1 hour at room temperature. 2.0 g (35.2 mmol) of dehydrated acetone (dimethylketone, $CH_3COCH_3$) is added thereto at −50° C. and then, stirred at room temperature for 2 hours. An organic layer extracted in diethyl ether is washed with a sodium chloride aqueous solution and then, dried by adding anhydrous magnesium sulfate thereto. Herein, a product obtained therefrom is separated and purified through silica gel column chromatography (in a volume ratio between hexane:dichloromethane=100:0 to 50:50 to obtain 6.3 g (Yield: 56%) of Compound 2a-2.

(iii) Synthesis of Compound 2a-3

6.23 g (17.6 mmol) of Compound 2a-2 is dissolved in 180 ml of dichloromethane. 4.98 g (35.5 mmol) of a boron trifluoride-ethyl ether complex is added thereto in a dropwise fashion at 0° C. and then, stirred for 2 hours. An organic layer extracted in dichloromethane is washed with a sodium chloride aqueous solution and then, dried by adding anhydrous magnesium sulfate thereto. Herein, a product obtained therefrom is separated and purified through silica gel column chromatography (in a volume ratio between hexane:dichloromethane=50:50) to obtain 5.12 g (Yield: 87%) of Compound 2a-3.

(iv) Synthesis of Compound 2a-4

1.9 ml (20.2 mmol) of phosphoryl chloride is added in a dropwise fashion to 6.0 ml (77.5 mmol) of N,N-dimethyl formamide (DMF) at −15° C. and then, stirred at room temperature for 2 hours. This solution is slowly dripped to 150 ml of a dichloromethane solution of 5.23 g (15.5 mmol) of Compound 2a-3 at −15° C. and then, concentrated under a low pressure, while stirred at room temperature for 30 hours. Subsequently, water is added thereto, and a sodium hydroxide aqueous solution is added thereto until pH becomes 1 quadrivalent, and the obtained mixture is stirred at room temperature for 2 hours. An organic layer extracted with dichloromethane is washed with a sodium chloride aqueous solution and then, dried with anhydrous magnesium sulfate. A product obtained therefrom is separated and purified through silica gel column chromatography (in a volume ratio of hexane:dichloromethane=50:50) to obtain 3.34 g (Yield: 65%) of Compound 2a-4.

(v) Synthesis of Compound 2a 2.00 g (5.55 mmol) of 4,4-dimethyl-4H-selenopheno[3', 2': 5,6]pyrido[3,2,1-jk]carbazole-2-carbaldehyde (Compound 2a-4) is suspended in ethanol, and 1.05 g (6.66 mmol) of 1-methyl-2-thioxodihydropyrimidine-4,6(1H, 5H)-dione is added thereto and then, reacted at 50° C. for 24 hours, obtaining 2.4 g of Compound 2a. A yield thereof is 86%. The obtained compound is purified by sublimation up to purity of 99.9%.

1H-NMR (500 MHZ, Methylene Chloride-d2): δ 8.95 (s, 0.5H), 8.77 (s, 0.5H), 8.65 (s, 1H), 8.18 (s, 1H) 8.06 (d, 1H), 7.92 (d, 1H), 7.83 (d, 1H), 7.62 (d, 1H), 7.44 (t, 1H), 7.36 (m, 2H), 3.76 (s, 1.5H), 3.71 (s, 1.5H), 1.68 (s, 6H).

Synthesis Example 4

[Compound 2b]

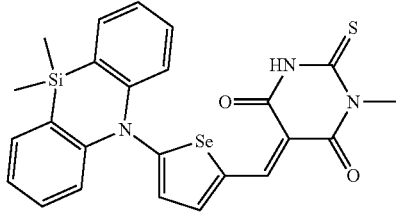

[Reaction Scheme 2]

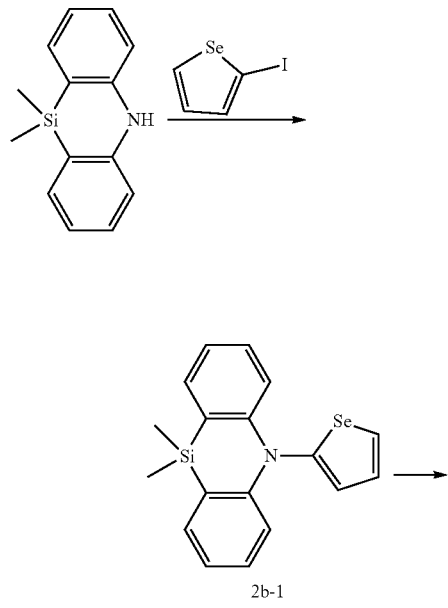

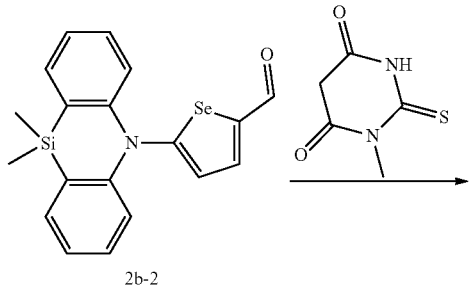

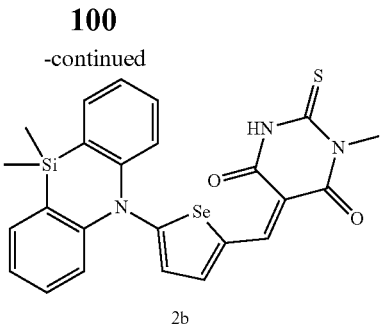

2b (i) Synthesis of Compound 2b-1

Under the presence of 5 mol % of tris(dibenzylideneacetone) dipalladium (0) (Pd(dba)2), 5 mol % of tri-t-butylphosphine (P(t-Bu)3), and 7.15 g (74.4 mmol) of sodium t-butoxide (NaOtBu), 7.01 g (27.3 mmol) of 2-iodoselenophene and 5.59 g (24.8 mmol) of 10,10-dimethyl-5,10-dihydrodibenzo[b,e][1,4]azasiline are heated under reflux in 150 ml of anhydrous toluene for 2 hours. A product obtained therefrom is separated and purified through silica gel column chromatography (in a volume ratio of toluene:hexane=1:4), obtaining 8.0 g of Compound 2b-1 (10,10-dimethyl-5-(selenophen-2-yl)-5,10-dihydrodibenzo[b,e][1,4]azasiline). A yield thereof is 80%.

(ii) Synthesis of Compound 2b-2

1.11 ml of phosphoryl chloride is added dropwise to 3.19 ml of N,N-dimethylformamide at −15° C. and then, stirred at room temperature (24° C.) for 2 hours. Subsequently, the resulting material is slowly added dropwise to a mixed solution of 200 ml of dichloromethane and 3.19 g of Compound 2b-1 at −15° C. and then, stirred at room temperature (24° C.) for 30 minutes and concentrated under a reduced pressure. Then, 100 ml of water is added thereto, and subsequently, an aqueous sodium hydroxide solution is added thereto until pH becomes 14 and then, stirred at room temperature (24° C.) for 2 hours. Then, the resulting material is treated with dichloromethane to extract an organic layer, and the organic layer is washed with an aqueous sodium chloride solution and dried with anhydrous magnesium sulfate. A product obtained therefrom is separated and purified through silica gel column chromatography (in a volume ratio of hexane:ethylacetate=4:1), obtaining 2.20 g of Compound 2b-2 (5-(10,10-dimethyldibenzo[b,e][1,4]azasilin-5 (10H)-yl)selenoophene-2-carbaldehyde). A yield thereof is 64%.

(iii) Synthesis of Compound 2b 1.77 g (4.64 mmol) of Compound 2b-2 is suspended in ethanol, and 0.89 g (5.57 mmol) of 1-methyl-2-thioxodihydropyrimidine-4,6(1H,5H)-dione is added thereto and then, reacted at 50° C. for 2 hours, obtaining 2.0 g of Compound 2b. A yield thereof is 83%. The obtained compound is purified by sublimation up to purity of 99.9%.

1H-NMR (500 MHZ, DMSO-d6): δ12.1 (d, 1H), 8.29 (d, 1H), 8.22 (dd, 1H), 7.89 (dd, 2H) 7.76 (d, 2H), 7.61 (q, 2H), 7.48 (q, 2H), 6.59 (t, 1H), 3.48 (d, 3H), 0.41 (s, 6H).

Evaluation I

The organic materials obtained in the Synthesis Examples are evaluated with respect to a sublimation temperature.

The sublimation temperature is evaluated by using a thermogravimetric analysis (TGA) to measure a temperature that a weight of a sample is reduced by 10% relative to the initial weight, while the temperature is increased under a high vacuum of 10 Pa or less.

The results are shown in Tables 1 and 2.

TABLE 1

|  | $T_{s\,(10)}$ (° C.) |
|---|---|
| Synthesis Example 1 | 270 |
| Synthesis Example 2 | 204 |
| Reference Synthesis Example | 450 |

TABLE 2

|  | $T_{s\,(10)}$ (° C.) |
|---|---|
| Synthesis Example 3 | 270 |
| Synthesis Example 4 | 241 |

* $T_{s\,(10)}$ (° C.): A temperature that a weight of a sample is reduced by 10% from the initial weight Evaluation II The organic materials according to Synthesis Examples are respectively deposited on a glass substrate, and the deposited thin films are measured with respect to energy levels.

A HOMO energy level is obtained by irradiating UV light into the thin films with and measuring an amount of photoelectrons emitted according to the energy AC-2 (Hitachi) or AC-3 (Riken Keiki Co., Ltd.). An energy bandgap is obtained by using a UV-Vis spectrometer (Shimadzu Corp.) and then, a LUMO energy level is calculated by using the energy bandgap and the HOMO energy level.

The results are shown in Tables 3 and 4.

TABLE 3

|  | HOMO (eV) | LUMO (eV) | Energy bandgap (eV) |
|---|---|---|---|
| Synthesis Example 1 | 6.19 | 3.20 | 2.99 |
| Synthesis Example 2 | 6.31 | 3.27 | 3.04 |
| Reference Synthesis Example | 6.40 | 4.23 | 2.17 |

TABLE 4

|  | HOMO (eV) | LUMO (eV) | Energy bandgap (eV) |
|---|---|---|---|
| Synthesis Example 3 | 5.66 | 3.70 | 1.96 |
| Synthesis Example 4 | 5.40 | 3.23 | 2.17 |

* HOMO, LUMO: absolute value

EXAMPLE

Example 1

Al (10 nm), ITO (100 nm), and Al (8 nm) are sequentially deposited on a glass substrate to form a lower electrode having an Al/ITO/Al structure. Subsequently, N,N'-bis(3-methylphenyl)-N,N'-diphenyl-[1,1-biphenyl]-4,4'-diamine is formed on the lower electrode to form a hole auxiliary layer (HOMO: 5.3 eV to 5.6 eV, LUMO: 2.0 eV to 2.3 eV). On hole auxiliary layer, the third organic material (i.e., Compound 2a, p-type semiconductor, HOMO: 5.66 eV, LUMO: 3.70 eV) according to Synthesis Example 3 is deposited to be 15 nm thick, and subsequently, the second organic material (i.e., Compound 1a, n-type semiconductor, HOMO: 6.19 eV, LUMO: 3.20 eV) according to Synthesis Example 1 is deposited to be 35 nm thick, forming a bi-layered light absorbing layer ($\lambda_{max}$=556 nm). On the light absorbing layer, 4,7-diphenyl-1,10-phenanthroline is deposited to form an electron auxiliary layer (HOMO: 6.1 eV to 6.4 eV, LUMO: 2.9 eV to 3.2 eV). Then, magnesium and silver are deposited on the electron auxiliary layer to form a Mg:Ag upper electrode to manufacture a light absorption sensor.

Example 2

A light absorption sensor is manufactured according to the same method as Example 1 except that the second organic material (i.e., Compound 1b) of Synthesis Example 2 instead of the second organic material of Synthesis Example 1 is used as the n-type semiconductor.

Reference Example 1

A light absorption sensor is manufactured according to the same method as Example 1 except that the fullerene (C60) of Reference Synthesis Example instead of the second organic material of Synthesis Example 1 is used as the n-type semiconductor.

Example 3

A light absorption sensor is manufactured according to the same method as Example 1 except that the third organic material of Synthesis Example 4 instead of the second organic material (i.e., Compound 2b) of Synthesis Example 3 is used as the p-type semiconductor.

Reference Example 2

A light absorption sensor is manufactured according to the same method as Example 3 except that the fullerene (C60) of Reference Synthesis Example instead of the second organic material of Synthesis Example 1 is used as the n-type semiconductor.

Evaluation III

Photoelectric conversion efficiency of the light absorption sensors according to Examples and Reference Examples are evaluated.

The photoelectric conversion efficiency is evaluated from external quantum efficiency (EQE), which is measured by allowing the light absorption sensors according to Examples and Reference Examples to stand at 85° C. for 1 hour. The external quantum efficiency (EQE) is evaluated by using incident photon to current conversion efficiency (IPCE) at a wavelength of 450 nm (blue, B), 530 nm (green, G), and 630 nm (red, R) at a voltage of 3V.

The results are shown in Tables 5 and 6.

TABLE 5

|  | EQE (3V, %) | | | Wavelength selectivity | |
|---|---|---|---|---|---|
|  | EQE(B) | EQE(G) | EQE(R) | EQE(G)/ EQE(B) | EQE(G)/ EQE(R) |
| Example 1 | 0.9 | 75.0 | 4.2 | 83.3 | 17.9 |
| Reference Example 1 | 1.9 | 32.2 | 4.7 | 16.9 | 6.85 |

TABLE 6

| | EQE (3V, %) | | | Wavelength selectivity | |
| --- | --- | --- | --- | --- | --- |
| | EQE(B) | EQE(G) | EQE(R) | EQE(G)/EQE(B) | EQE(G)/EQE(R) |
| Example 3 | 1.2 | 60.7 | 0.1 | 50.6 | 607 |
| Reference Example 2 | 5.4 | 39.2 | 0.2 | 7.3 | 196 |

Referring to Tables 5 and 6, light absorption sensors according to Examples exhibit improved photoelectric conversion efficiency at a green wavelength spectrum and in addition, higher photoelectric conversion efficiency at a green wavelength relative to photoelectric conversion efficiency at a blue wavelength or a red wavelength and thus high wavelength selectivity, compared with the light absorption sensors according to Reference Examples.

Evaluation IV

The light absorption sensors according to Examples and Reference Examples are evaluated with respect to a dark current under a reverse bias voltage.

The dark current is evaluated with dark current density, which is obtained by using a current-voltage evaluating equipment (Keithley K4200 parameter analyzer) and dividing it by a unit pixel area (0.04 cm$^2$), and the dark current density is evaluated from a current flowing when a reverse bias of −3 V is applied thereto.

The results are shown in Tables 7 and 8.

TABLE 7

| | Dark current (mA/cm$^2$) |
| --- | --- |
| Example 1 | $2.0 \times 10^{-5}$ |
| Example 2 | $3.5 \times 10^{-5}$ |
| Reference Example 1 | $7.9 \times 10^{-5}$ |

TABLE 8

| | Dark current (mA/cm$^2$) |
| --- | --- |
| Example 3 | $2.0 \times 10^{-5}$ |
| Reference Example 2 | $7.3 \times 10^{-5}$ |

Referring to Tables 7 and 8, the light absorption sensors according to Examples exhibit a lower dark current than the light absorption sensors according to Reference Examples when the reverse bias is applied thereto.

While the inventive concepts have been described in connection with what is presently considered to be practical example embodiments, it is to be understood that the inventive concepts are not limited to such example embodiments, but, on the contrary, are intended to cover various modifications and equivalent arrangements included within the spirit and scope of the appended claims.

What is claimed is:

1. A sensor-embedded display panel, comprising:
   a substrate;
   a light emitting element on the substrate, the light emitting element including a light emitting layer; and
   a light absorption sensor on the substrate, the light absorption sensor including a light absorbing layer arranged in parallel with the light emitting layer along an in-plane direction of the substrate such that the light absorbing layer and the light emitting layer at least partially overlap in the in-plane direction,
   wherein the light absorbing layer is configured to absorb light of a red wavelength spectrum, a green wavelength spectrum, a blue wavelength spectrum, an infrared wavelength spectrum, or any combination thereof,
   wherein the light emitting layer includes a first organic material,
   wherein the light absorbing layer includes a second organic material, and
   wherein a difference between a sublimation temperature of the first organic material and a sublimation temperature of the second organic material is less than or equal to about 150° C., wherein each sublimation temperature of each given organic material is a temperature at which a weight reduction of 10% relative to an initial weight of the given organic material occurs during thermogravimetric analysis under an ambient pressure of about 10 Pa or less.

2. The sensor-embedded display panel of claim 1, wherein
   the light emitting element comprises first, second, and third light emitting elements configured to emit light of different wavelength spectra from each other, and
   the light absorption sensor is configured to absorb light that is emitted from at least one of the first, second, or third light emitting elements and is reflected by a recognition target and to convert the reflected light into an electrical signal.

3. The sensor-embedded display panel of claim 1, wherein the sublimation temperature of the second organic material is less about 0° C. to about 390° C.

4. The sensor-embedded display panel of claim 3, wherein the sublimation temperature of the second organic material is about 100° C. to about 390° C.

5. The sensor-embedded display panel of claim 1, wherein an energy bandgap of the second organic material is greater than or equal to about 2.5 eV.

6. The sensor-embedded display panel of claim 1, wherein the second organic material is a transparent n-type semiconductor.

7. The sensor-embedded display panel of claim 1, wherein
   the light emitting element and the light absorption sensor each comprise a separate portion of a common electrode configured to apply a common voltage to both the light emitting element and the light absorption sensor, and
   the sensor-embedded display panel further comprises a first common auxiliary layer continuously formed as a single piece of material that extends between the light emitting layer and the common electrode and between the light absorbing layer and the common electrode.

8. The sensor-embedded display panel of claim 7, wherein a difference between a lowest unoccupied molecular orbital (LUMO) energy level of the first common auxiliary layer and a LUMO energy level of the second organic material is about 0 eV to about 1.2 eV.

9. The sensor-embedded display panel of claim 7, further comprising a second common auxiliary layer continuously formed as a single piece of material that extends between the light emitting layer and the substrate and between the light absorbing layer and the substrate.

10. The sensor-embedded display panel of claim 1, wherein the second organic material is represented by Chemical Formula 1:

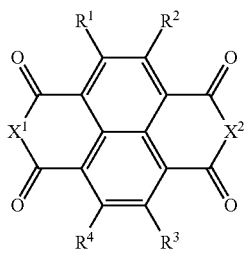

[Chemical Formula 1]

wherein, in Chemical Formula 1,
$X^1$ and $X^2$ are each independently O or $NR^a$, and
$R^1$ to $R^4$ and $R^a$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

11. The sensor-embedded display panel of claim 10, wherein the second organic material is represented by Chemical Formula 1A or 1B:

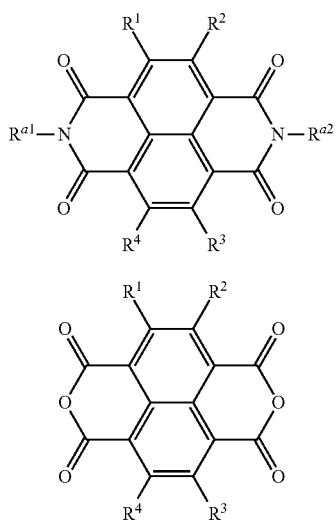

[Chemical Formula 1A]

[Chemical Formula 1B]

wherein, in Chemical Formulas 1A and 1B,
$R^1$ to $R^4$, $R^{a1}$, and $R^{a2}$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof.

12. The sensor-embedded display panel of claim 11, wherein at least one of $R^{a1}$ or $R^{a2}$ comprises an electron withdrawing group.

13. The sensor-embedded display panel of claim 12, wherein at least one of $R^{a1}$ or $R^{a2}$ is a halogen; a cyano group; a halogen-substituted C1 to C30 alkyl group; a halogen-substituted C6 to C30 aryl group; a halogen-substituted C3 to C30 heterocyclic group; a cyano-substituted C1 to C30 alkyl group; a cyano-substituted C6 to C30 aryl group; a cyano-substituted C3 to C30 heterocyclic group; a substituted or unsubstituted pyridinyl group; a substituted or unsubstituted pyrimidinyl group; a substituted or unsubstituted triazinyl group; a substituted or unsubstituted pyrazinyl group; a substituted or unsubstituted quinolinyl group; a substituted or unsubstituted isoquinolinyl group; a substituted or unsubstituted quinazolinyl group; a C1 to C30 alkyl group substituted with a substituted or unsubstituted pyridinyl group; a C6 to C30 aryl group substituted with a substituted or unsubstituted pyridinyl group; a C1 to C30 alkyl group substituted with a substituted or unsubstituted pyrimidinyl group; a C6 to C30 aryl group substituted with a substituted or unsubstituted pyrimidinyl group; a C1 to C30 alkyl group substituted with a substituted or unsubstituted triazinyl group; a C6 to C30 aryl group substituted with a substituted or unsubstituted triazinyl group; a C1 to C30 alkyl group substituted with a substituted or unsubstituted pyrazinyl group; a C6 to C30 aryl group substituted with a substituted or unsubstituted pyrazinyl group; a C1 to C30 alkyl group substituted with a substituted or unsubstituted quinolinyl group; a C6 to C30 aryl group substituted with a substituted or unsubstituted quinolinyl group; a C1 to C30 alkyl group substituted with a substituted or unsubstituted isoquinolinyl group; a C6 to C30 aryl group substituted with a substituted or unsubstituted isoquinolinyl group; a C1 to C30 alkyl group substituted with a substituted or unsubstituted quinazolinyl group; a C6 to C30 aryl group substituted with a substituted or unsubstituted quinazolinyl group; or any combination thereof.

14. The sensor-embedded display panel of claim 1, wherein
the light absorbing layer further comprises a third organic material forming a pn junction with the second organic material, and
a difference between respective sublimation temperatures of two materials of the first organic material, the second organic material, or the third organic material is about 0° C. to about 150° C.

15. The sensor-embedded display panel of claim 14, wherein the third organic material is a light absorbing material configured to selectively absorb light of any one of the red wavelength spectrum, the green wavelength spectrum, the blue wavelength spectrum, or the infrared wavelength spectrum.

16. The sensor-embedded display panel of claim 14, wherein the third organic material is represented by Chemical Formula 2:

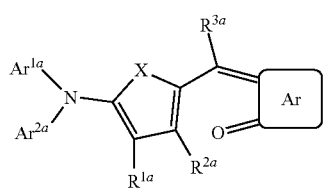

[Chemical Formula 2]

wherein, in Chemical Formula 2,
X is O, S, Se, Te, SO, $SO_2$, $CR^bR^c$, or $SiR^dR^e$,
Ar is a substituted or unsubstituted C6 to C30 arylene group, a substituted or unsubstituted C3 to C30 heterocyclic group, or a fused ring of two or more thereof,
$Ar^{1a}$ and $Ar^{2a}$ are each independently a substituted or unsubstituted C6 to C30 aryl(ene) group or a substituted or unsubstituted C3 to C30 heteroaryl(ene) group, $R^{1a}$ to $R^{3a}$ and $R^b$ to $R^e$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, and $Ar^{1a}$, $Ar^{2a}$, $R^{1a}$ and $R^{2a}$ are each independently present, or two adjacent ones of $Ar^{1a}$, $Ar^{2a}$, $R^{1a}$ or $R^{2a}$ are bonded to each other to form a ring.

17. The sensor-embedded display panel of claim 16, wherein the third organic material is represented by Chemical Formula 2A or 2B:

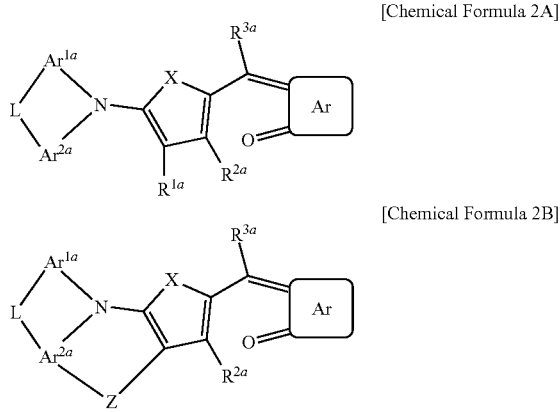

[Chemical Formula 2A]

[Chemical Formula 2B]

wherein, in Chemical Formulas 2A and 2B,

X is O, S, Se, Te, SO, $SO_2$, $CR^bR^c$, or $SiR^dR^e$,

Ar is a substituted or unsubstituted C6 to C30 arylene group, a substituted or unsubstituted C3 to C30 heterocyclic group, or a fused ring of two or more thereof, $Ar^{1a}$ and $Ar^{2a}$ are each independently a substituted or unsubstituted C6 to C30 arylene group or a substituted or unsubstituted C3 to C30 heteroarylene group, L and Z are each independently a single bond, O, S, Se, Te, SO, $SO_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and $R^{1a}$, $R^{2a}$, $R^{3a}$, and $R^b$ to $R^l$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof.

18. The sensor-embedded display panel of claim 1, wherein the light emitting element comprises first, second, and third light emitting elements that are each configured to emit light of any one of the red wavelength spectrum, the green wavelength spectrum, the blue wavelength spectrum, or the infrared wavelength spectrum, and the light absorbing layer is configured to absorb light of a same wavelength spectrum as light emitted from at least one of the first, second, or third light emitting elements.

19. The sensor-embedded display panel of claim 1, wherein the sensor-embedded display panel comprises a display area configured to display a color and a non-display area excluding the display area, and the light absorption sensor is in the non-display area.

20. The sensor-embedded display panel of claim 19, wherein the light emitting element comprises first, second, and third light emitting elements configured to emit light of different wavelength spectra from each other, and the display area comprises
a plurality of first subpixels configured to display red and comprising the first light emitting element,
a plurality of second subpixels configured to display green and comprising the second light emitting element, and
a plurality of third subpixels configured to display blue and comprising the third light emitting element, and the light absorption sensor is between at least two of a first subpixel of the plurality of first subpixels, a second subpixel of the plurality of second subpixels, or a third subpixel of the plurality of third subpixels in the in-plane direction.

21. An electronic device comprising the sensor-embedded display panel of claim 1.

22. A sensor-embedded display panel, comprising:
a display area configured to display a color and a non-display area excluding the display area and configured to not display any color,
wherein the display area includes
a first subpixel configured to display a first color and including a first light emitting element,
a second subpixel configured to display a second color and including a second light emitting element, and
a third subpixel configured to display a third color and including a third light emitting element,
wherein the non-display area includes a light absorption sensor that is between at least two of the first subpixel, the second subpixel, or the third subpixel,
wherein the first, second, and third light emitting elements include respective first, second, and third light emitting layers configured to emit light of an emission spectrum corresponding to the first, second, and third colors, respectively,
wherein the light absorption sensor comprises a light absorbing layer comprising a p-type semiconductor and an n-type semiconductor forming a pn junction, and configured to absorb light reflected by a recognition target and convert the reflected light into an electrical signal,
wherein respective sublimation temperatures of organic materials included in the first, second, and third light emitting layers and the n-type semiconductor are each less than or equal to about 390° C., respectively, wherein each sublimation temperature of each given organic material and the n-type semiconductor is a temperature at which a weight reduction of 10% relative to an initial weight of the given organic material and the n-type semiconductor occurs during thermogravimetric analysis under an ambient pressure of about 10 Pa or less, and
wherein a difference in respective sublimation temperatures between the organic materials included in the first, second, and third light emitting layers and the n-type semiconductor is about 0° C. to about 150° C.

23. The sensor-embedded display panel of claim 22, wherein
the first, second, and third light emitting elements and the light absorption sensor each include
a separate portion of a common electrode configured to apply a common voltage to the first, second, and third light emitting elements and the light absorption sensor, and
a separate portion of a first common auxiliary layer between the first, second, and third light emitting layers and the common electrode and between the light absorbing layer and the common electrode,
a lowest unoccupied molecular orbital (LUMO) energy level of the first common auxiliary layer is between a LUMO energy level of each separate light emitting layer of the first, second, and third light emitting layers and a work function of the common electrode, and
a difference between the LUMO energy level of the first common auxiliary layer and a LUMO energy level of the n-type semiconductor is about 0 eV to about 1.2 eV.

24. The sensor-embedded display panel of claim 22, wherein
the n-type semiconductor is represented by Chemical Formula 1, and
the p-type semiconductor is represented by Chemical Formula 2:

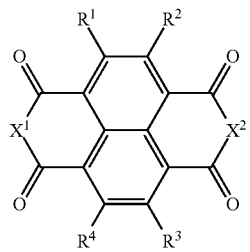

[Chemical Formula 1]

wherein, in Chemical Formula 1,
$X^1$ and $X^2$ are each independently O or $NR^a$, and
$R^1$ to $R^4$ and $R^a$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof,

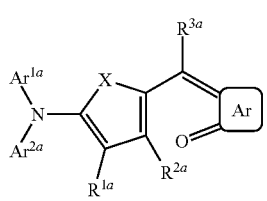

[Chemical Formula 2]

wherein, in Chemical Formula 2,
X is O, S, Se, Te, SO, $SO_2$, $CR^bR^c$, or $SiR^dR^e$,
Ar is a substituted or unsubstituted C6 to C30 arylene group, a substituted or unsubstituted C3 to C30 heterocyclic group, or a fused ring of two or more thereof,
$Ar^{1a}$ and $Ar^{2a}$ are each independently a substituted or unsubstituted C6 to C30 aryl(ene) group or a substituted or unsubstituted C3 to C30 heteroaryl(ene) group, $R^{1a}$ to $R^{3a}$ and $R^b$ to $R^e$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof, and
$Ar^{1a}$, $Ar^{2a}$, $R^{1a}$ and $R^{2a}$ are each independently present, or two adjacent ones of $Ar^{1a}$, $Ar^{2a}$, $R^{1a}$ or $R^{2a}$ are bonded to each other to form a ring.

25. The sensor-embedded display panel of claim 24, wherein the n-type semiconductor is represented by Chemical Formula 1A or 1B:

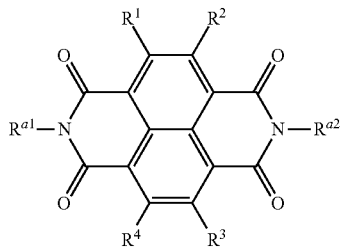

[Chemical Formula 1A]

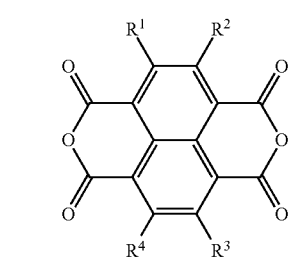

[Chemical Formula 1B]

wherein, in Chemical Formulas 1A and 1B,
$R^1$ to $R^4$, $R^{a1}$, and $R^{a2}$ are each independently hydrogen, a substituted or unsubstituted C1 to C30 alkyl group, a substituted or unsubstituted C6 to C30 aryl group, a substituted or unsubstituted C3 to C30 heterocyclic group, a halogen, a cyano group, or any combination thereof, and
at least one of $R^{a1}$ or $R^{a2}$ is a halogen; a halogen-substituted C1 to C30 alkyl group; a halogen-substituted C6 to C30 aryl group; a halogen-substituted C3 to C30 heterocyclic group; a cyano group; a cyano-substituted C1 to C30 alkyl group; a cyano-substituted C6 to C30 aryl group; a cyano-substituted C3 to C30 heterocyclic group; a substituted or unsubstituted pyridinyl group; a substituted or unsubstituted pyrimidinyl group; a substituted or unsubstituted triazinyl group; a substituted or unsubstituted pyrazinyl group; a substituted or unsubstituted quinolinyl group; a substituted or unsubstituted isoquinolinyl group; a substituted or unsubstituted quinazolinyl group; a C1 to C30 alkyl group substituted with a substituted or unsubstituted pyridinyl group; a C6 to C30 aryl group substituted with a substituted or unsubstituted pyridinyl group; a C1 to C30 alkyl group substituted with a substituted or unsubstituted pyrimidinyl group; a C6 to C30 aryl group substituted with a substituted or unsubstituted pyrimidinyl group; a C1 to C30 alkyl group substituted with a substituted or unsubstituted triazinyl group; a C6 to C30 aryl group substituted with a substituted or unsubstituted triazinyl group; a C1 to C30 alkyl group substituted with a substituted or unsubstituted pyrazinyl group; a C6 to C30 aryl group substituted with a substituted or unsubstituted pyrazinyl group; a C1 to C30 alkyl group substituted with a substituted or unsubstituted quinolinyl group; a C6 to C30 aryl group substituted with a substituted or unsubstituted quinolinyl group; a C1 to C30 alkyl group substituted with a substituted or unsubstituted isoquinolinyl group; a C6 to C30 aryl group substituted with a substituted or unsubstituted isoquinolinyl group; a C1 to C30 alkyl group substituted with a substituted or unsubstituted quinazolinyl group; a C6 to C30 aryl group substituted with a substituted or unsubstituted quinazolinyl group; or any combination thereof.

26. The sensor-embedded display panel of claim 24, wherein the p-type semiconductor is represented by Chemical Formula 2A or 2B:

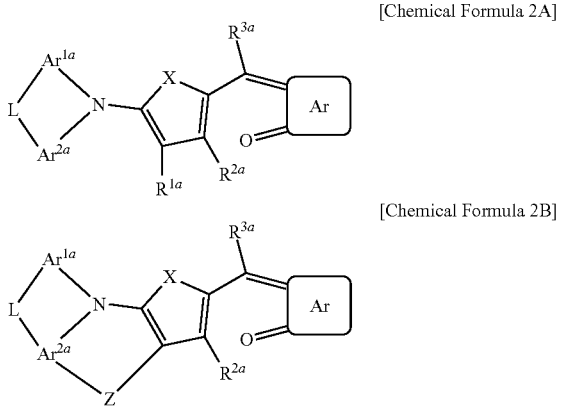

[Chemical Formula 2A]

[Chemical Formula 2B]

wherein, in Chemical Formulas 2A and 2B,

X is O, S, Se, Te, SO, $SO_2$, $CR^bR^c$, or $SiR^dR^e$,

Ar is a substituted or unsubstituted C6 to C30 arylene group, a substituted or unsubstituted C3 to C30 heterocyclic group, or a fused ring of two or more thereof, $Ar^{1a}$ and $Ar^{2a}$ are each independently a substituted or unsubstituted C6 to C30 arylene group or a substituted or unsubstituted C3 to C30 heteroarylene group, L and Z are each independently a single bond, O, S, Se, Te, SO, $SO_2$, $CR^fR^g$, $SiR^hR^i$, $GeR^jR^k$, $NR^l$, a substituted or unsubstituted C1 to C30 alkylene group, a substituted or unsubstituted C3 to C30 cycloalkylene group, a substituted or unsubstituted C6 to C30 arylene group, or any combination thereof, and $R^{1a}$, $R^{2a}$, $R^{3a}$, and $R^b$ to $R^l$ are each independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, or any combination thereof.

27. An electronic device comprising the sensor-embedded display panel of claim 22.

28. A sensor-embedded display panel, comprising:
a substrate;
a light emitting element on the substrate, the light emitting element including a light emitting layer; and
a light absorption sensor on the substrate, the light absorption sensor including
a pair of electrodes, and
a light absorbing layer between the pair of electrodes,
wherein the light absorbing layer of the light absorption sensor includes a first organic material and a second organic material that forms a pn junction with the first organic material,
wherein the light absorbing layer of the light absorption sensor is arranged in parallel with the light emitting layer along an in-plane direction of the substrate such that the light absorbing layer and the light emitting layer at least partially overlap in the in-plane direction,
wherein the light absorbing layer is configured to absorb light of a red wavelength spectrum, a green wavelength spectrum, a blue wavelength spectrum, or any combination thereof,
wherein the light emitting layer includes a third organic material, and
wherein a difference between respective sublimation temperatures of two materials of the first organic material, the second organic material, or the third organic material is about 0° C. to about 150° C., wherein each sublimation temperature of each given organic material is a temperature at which a weight reduction of 10% relative to an initial weight of the given organic material occurs during thermogravimetric analysis under an ambient pressure of about 10 Pa or less.

29. An electronic device comprising the light absorption sensor of claim 28.

* * * * *